US011293040B2

(12) United States Patent
Schalk et al.

(10) Patent No.: US 11,293,040 B2
(45) Date of Patent: Apr. 5, 2022

(54) METHODS OF PRODUCING SESQUITERPENE COMPOUNDS

(71) Applicant: Firmenich SA, Geneva (CH)

(72) Inventors: Michel Schalk, Geneva (CH); Letizia Rocci, Geneva (CH)

(73) Assignee: FIRMENICH SA, Satigny (CH)

( * ) Notice: Subject to any disclaimer, the term of this patent is extended or adjusted under 35 U.S.C. 154(b) by 326 days.

(21) Appl. No.: 16/308,890

(22) PCT Filed: Jul. 19, 2017

(86) PCT No.: PCT/EP2017/068268
§ 371 (c)(1),
(2) Date: Dec. 11, 2018

(87) PCT Pub. No.: WO2018/015453
PCT Pub. Date: Jan. 25, 2018

(65) Prior Publication Data
US 2020/0308612 A1 Oct. 1, 2020

(30) Foreign Application Priority Data

Jul. 20, 2016 (GB) .................................... 1612609
Mar. 3, 2017 (EP) .................................... 17159264

(51) Int. Cl.
| | | |
|---|---|---|
| C12P 7/62 | (2006.01) | |
| C12P 5/00 | (2006.01) | |
| C12P 7/22 | (2006.01) | |
| C12P 7/26 | (2006.01) | |
| C12N 9/02 | (2006.01) | |
| C12N 9/88 | (2006.01) | |
| C12N 15/70 | (2006.01) | |

(52) U.S. Cl.
CPC .............. *C12P 7/62* (2013.01); *C12N 9/0042* (2013.01); *C12N 9/88* (2013.01); *C12N 15/70* (2013.01); *C12P 5/007* (2013.01); *C12P 7/22* (2013.01); *C12P 7/26* (2013.01); *C12Y 106/02004* (2013.01); *C12Y 402/03113* (2015.07)

(58) Field of Classification Search
CPC .... C12P 7/62; C12P 5/007; C12P 7/22; C12P 7/26; C12Y 402/03113; C12Y 106/02004; C12Y 402/03073; C12N 9/0042; C12N 9/88; C12N 15/70
See application file for complete search history.

(56) References Cited

FOREIGN PATENT DOCUMENTS

| | | |
|---|---|---|
| WO | 2006134523 A2 | 12/2006 |
| WO | 2016029153 A1 | 2/2016 |

OTHER PUBLICATIONS

Cankar et al., FEBS Letters 585:178-182, 2011.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Gavira et al., Metabolic Engineering 18:25-35, 2013.*
International Search Report and Written Opinion for international application No. PCT/EP2017/068268, dated Feb. 7, 2018.
XP002773649, "Full=Uncharacterized protein {ECO:0000313|EMBL:JAF95976.1}", retrieved from EBI accession No. Uniprot: A0A0A9VHA2, Jul. 6, 2016.
XP002777497, "SubName: Full=Putative uncharacterized protein Sb05g027640 {ECO:0000313|EMBL:ESS10305.I}", retrieved from EBI accession No. UNIPROT: C5Y8K3, Mar. 16, 2016.
XP002773650, "*Zea mays* growth related protein (GRP)-encoding DNA, SEQ :143", retrieved from EBI accession No. GSN: BA059272, Jul. 18, 2013.
European Search Report for EP patent application 17159264.5, dated Sep. 20, 2017.

* cited by examiner

*Primary Examiner* — Delia M Ramirez
(74) *Attorney, Agent, or Firm* — Armstrong Teasdale LLP

(57) ABSTRACT

Provided is a method of producing one or more sesquiterpene compounds comprising: contacting an acyclic FPP precursor with a polypeptide having terpene synthase activity, wherein the polypeptide comprises an amino acid sequence that has at least 55% sequence identity to SEQ ID NO: 1, to produce one or more terpenes selected from the group consisting of isovalencene, spirovetiva-1(10),7(11)-diene and valencene or derivatives thereof, or mixture of sesquiterpenes comprising one or more of isovalencene, spirovetiva-1(10),7(11)-diene and/or valencene; and optionally isolating the one or more terpenes or the mixture. Also described is a nucleic acid derived from *Vetiveria zizanoides* encoding a polypeptide having sesquiterpene synthase activity, a polypeptide that can be used to produce one or more sesquiterpenes or a mixture of sesquiterpenes comprising one or more of isovalencene, spirovetiva-1(10),7(11)-diene and/or valencene, and a non-human organism or cell comprising the nucleic acid or comprising an expression vector comprising the nucleic acid.

16 Claims, 12 Drawing Sheets
Specification includes a Sequence Listing.

- Figure 1A -

Compound 1

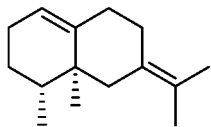

CAS Registry Number 16641-26-2
Isovalencene
(4S,5R)-4a,5-dimethyl-3-(propan-2-ylidene)-1,2,3,4,4a,5,6,7-octahydronaphthalene
4β,5α-eremophila-1(10),7(11)-diene

Compound 2

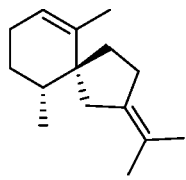

CAS Registry Number 39850-96-9
spirovetiva-1(10),7(11)-diene
(5RS,6RS)-2-ISOPROPYLIDENE-6,10-DIMETHYL-SPIRO[4.5]DEC-6-ENE
(5R,10R)-6,10-dimethyl-2-(propan-2-ylidene)spiro[4.5]dec-6-ene

Compound 3

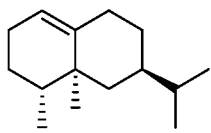

CAS Registry Number 4630-07-3
(+)-Valencene
4βH,5α-Eremophila-1(10),11-diene
(3R,4aS,5R)-3-isopropyl-4a,5-dimethyl-1,2,3,4,4a,5,6,7-octahydronaphthalene

- Figure 1B -
Isovalencenyl acetate.
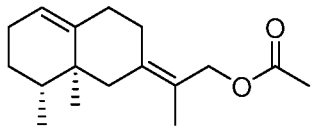
CAS Registry Number 352461-71-3
(E)-Eremophila-1(10),7(11)-dien-12-yl acetate
Isovalencenol
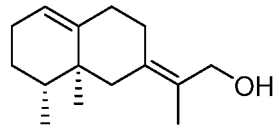
CAS Registry Number 22387-74-2
4βH,5α-Eremophila-1(10),7(11)-dien-12-ol
nootkatol
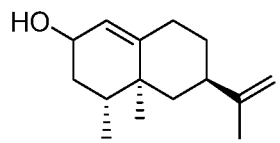
β-vetivol
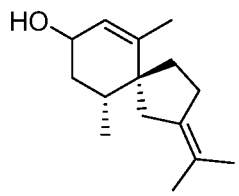
isonootkatol
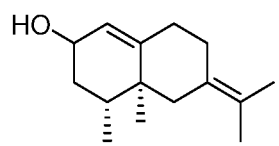

- Figure 1C –
nootkatol
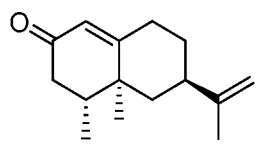
β-vetivone
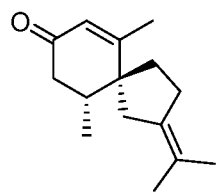
nootkatone
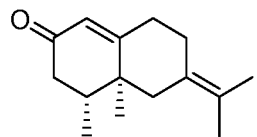

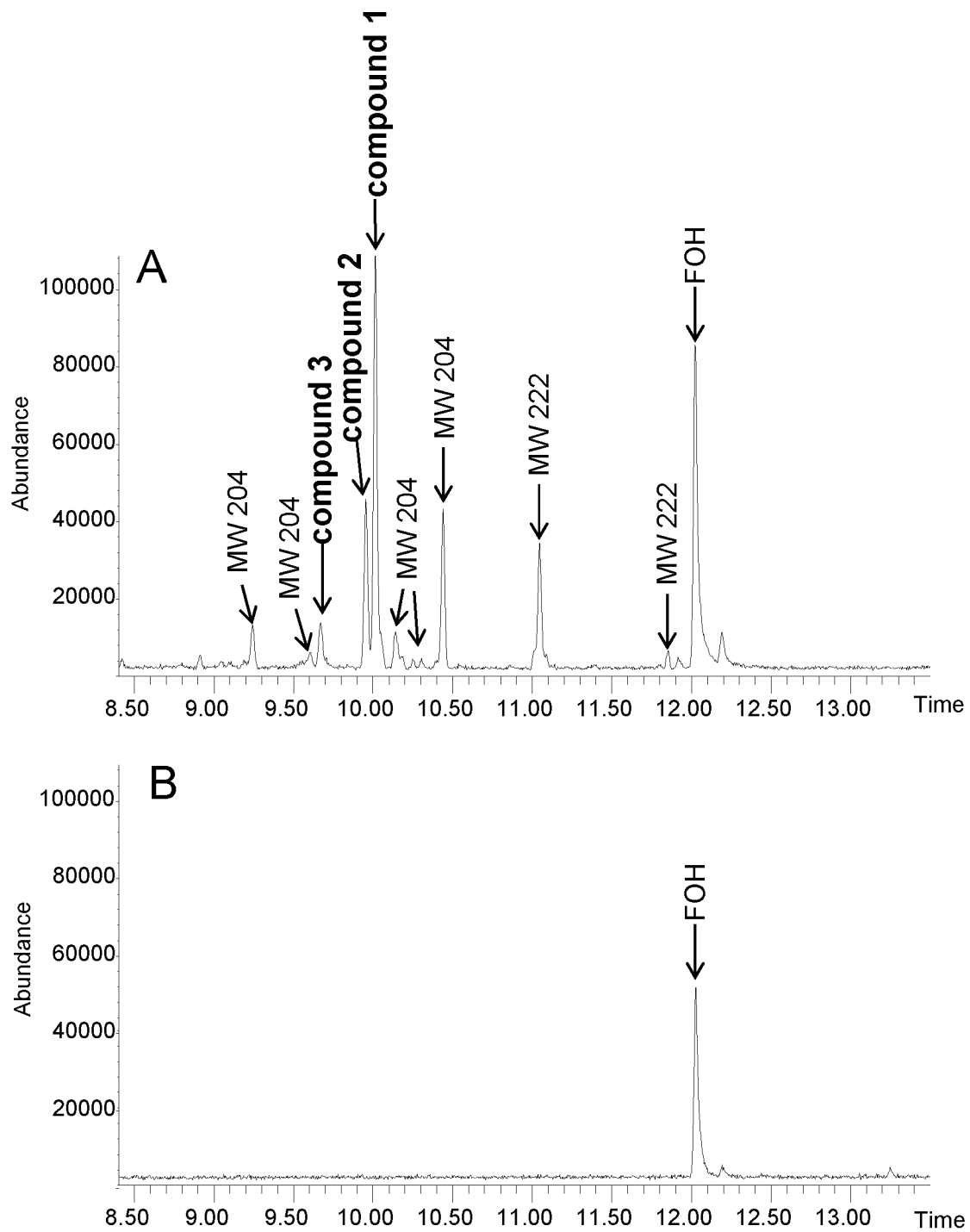
- Figure 2 -

- Figure 3 -
Mass spectrum of compound 1
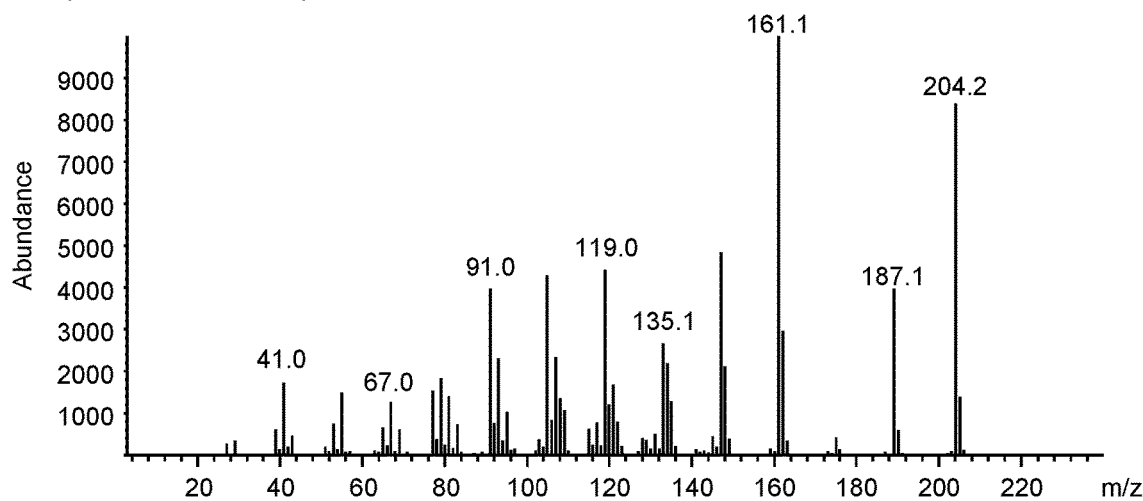
Mass spectrum of isovalencene standard
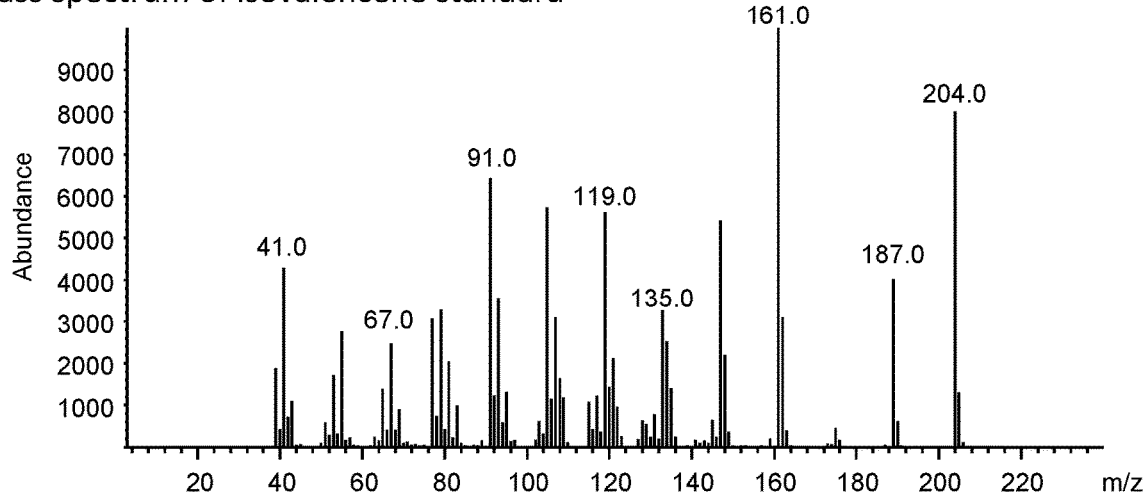

- Figure 4 -
Mass spectrum of compound 2
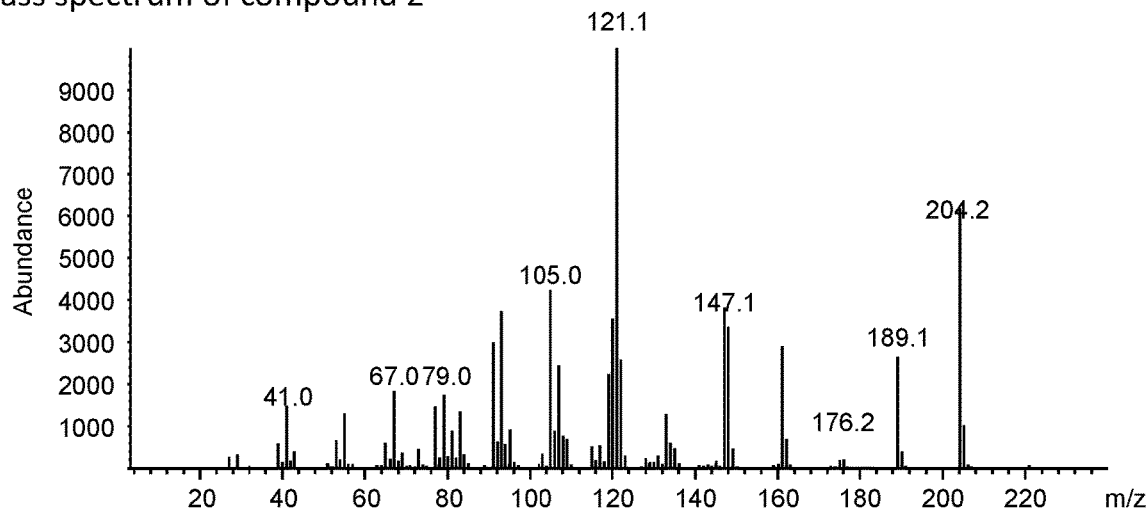
Mass spectrum of spirovetiva-1(10),7(11)-diene standard
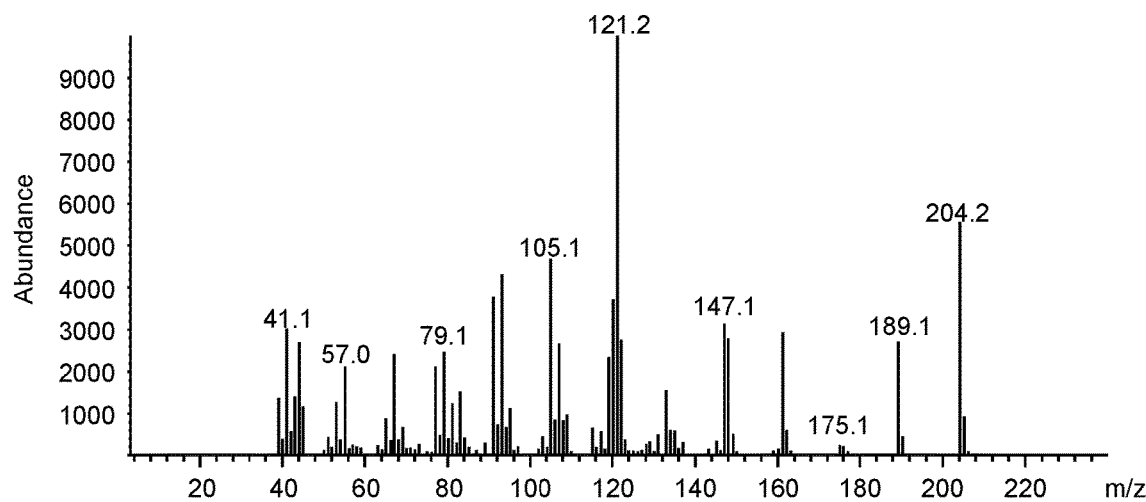

- Figure 5 -
Mass spectrum of compound 3
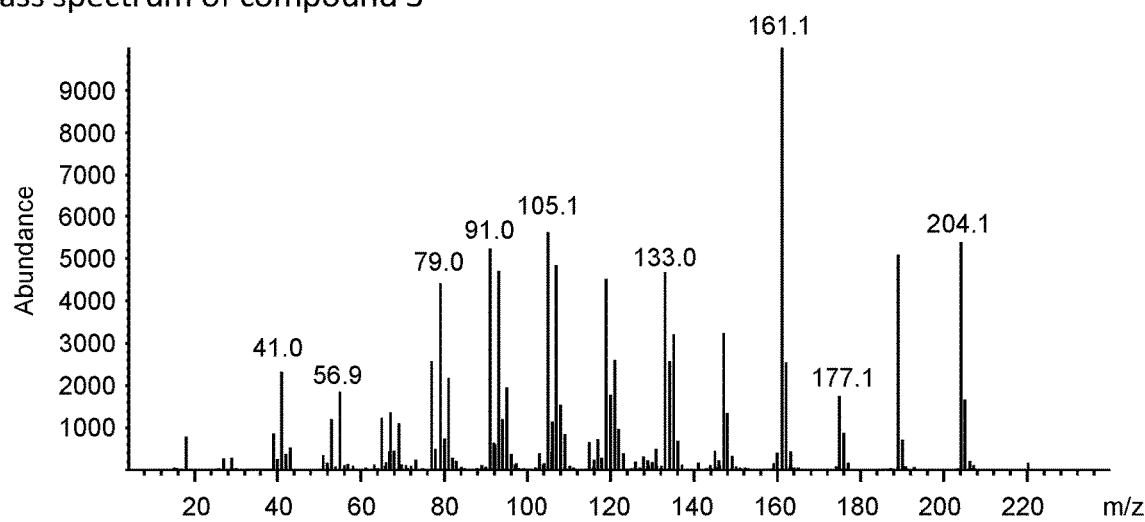
Mass spectrum of (+)-valencene standard
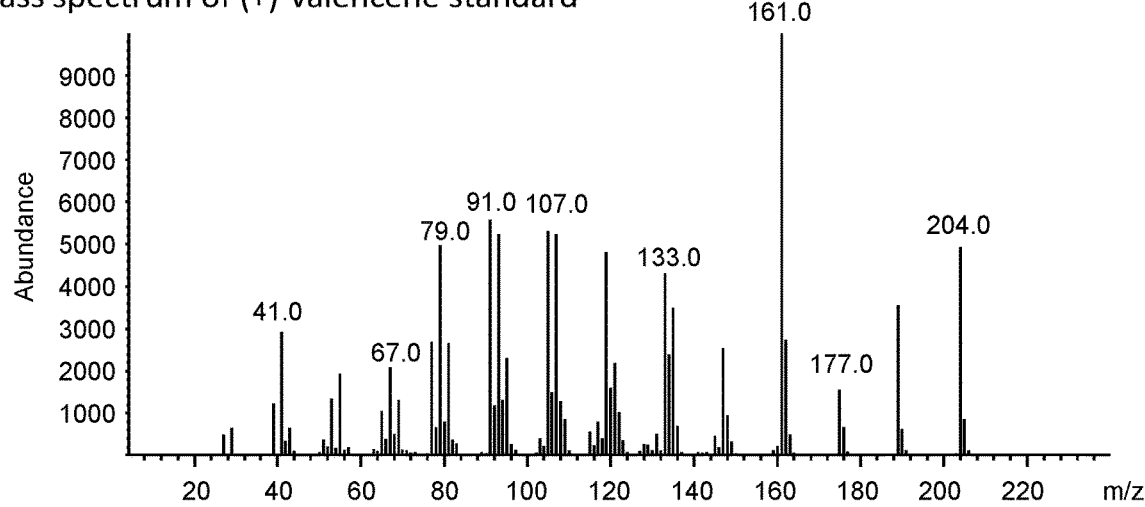

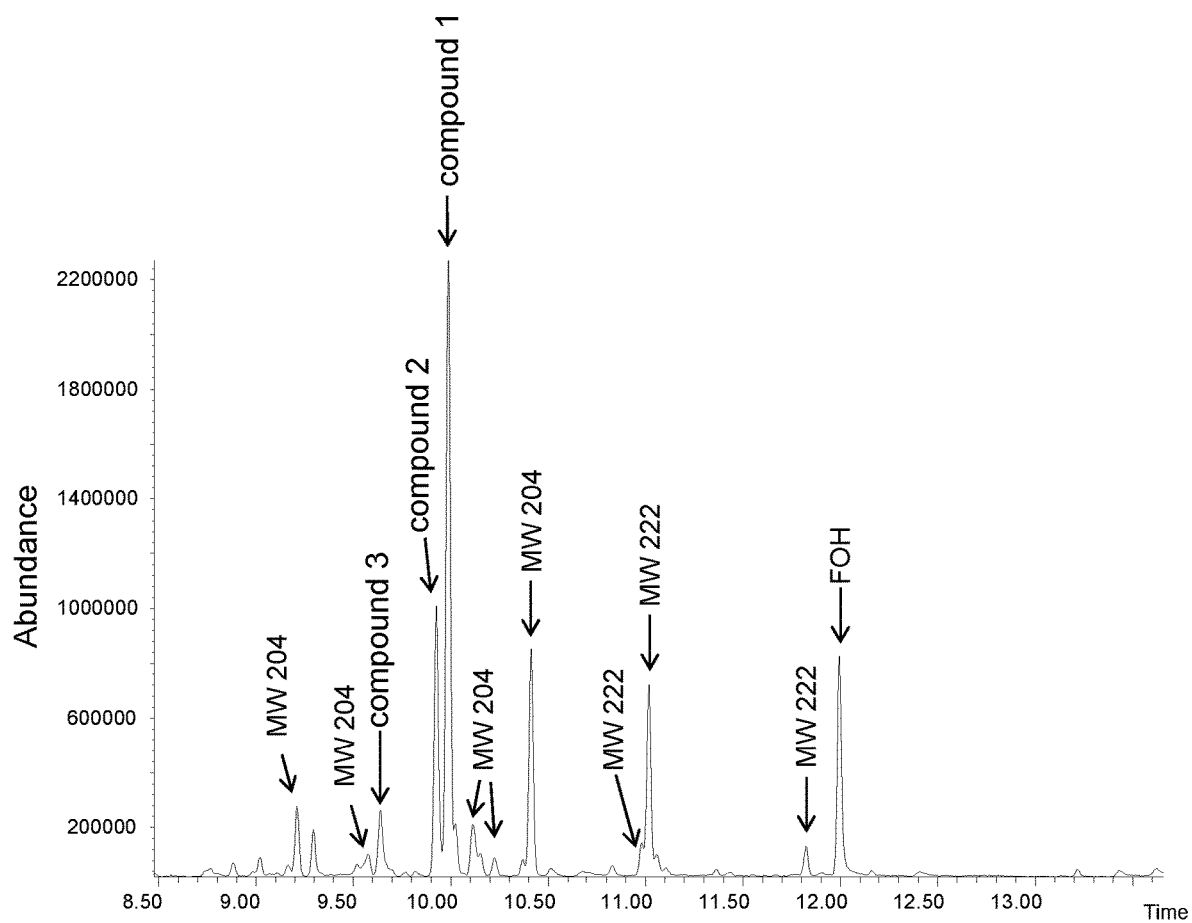
- Figure 6 -

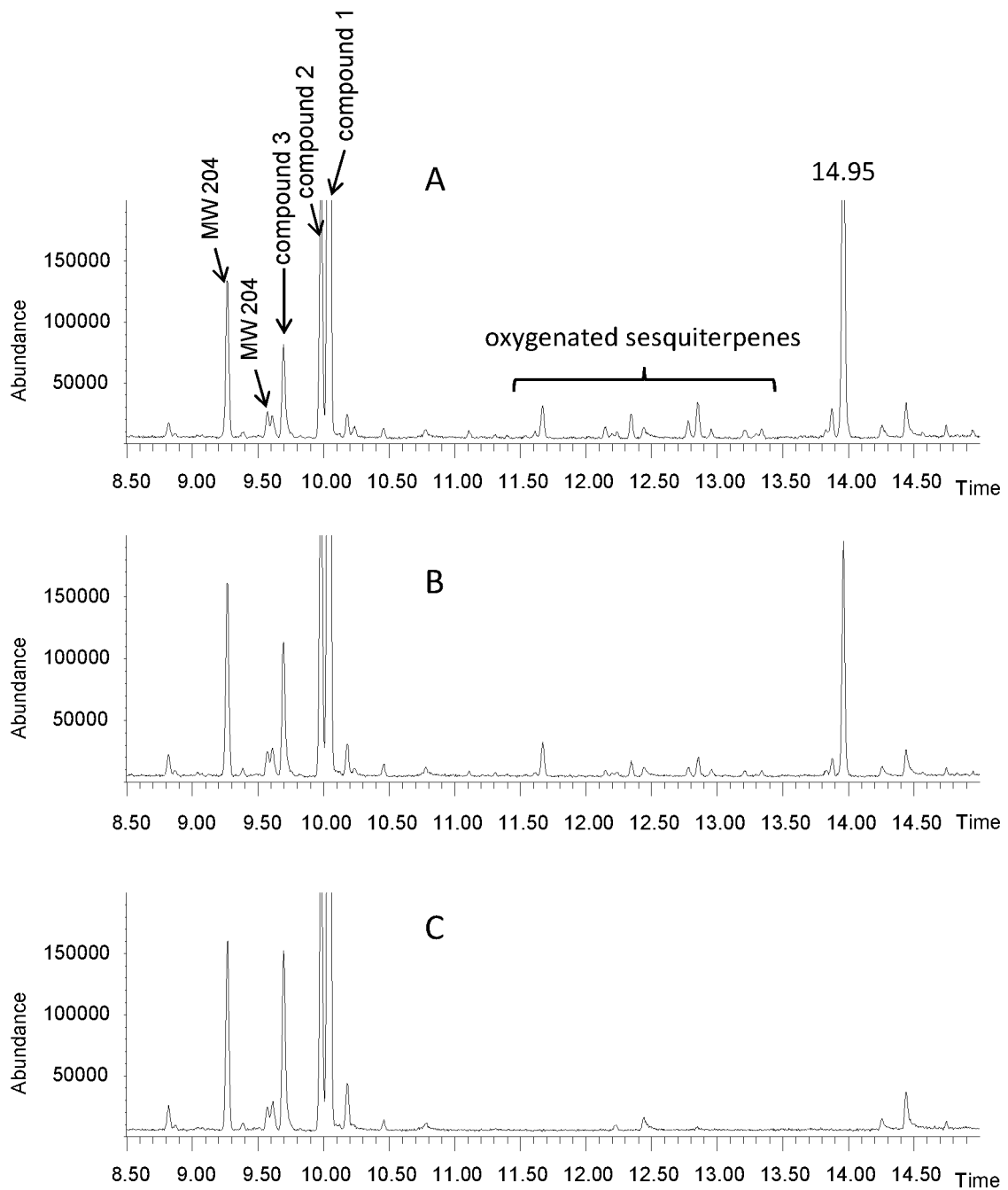
- Figure 7 -

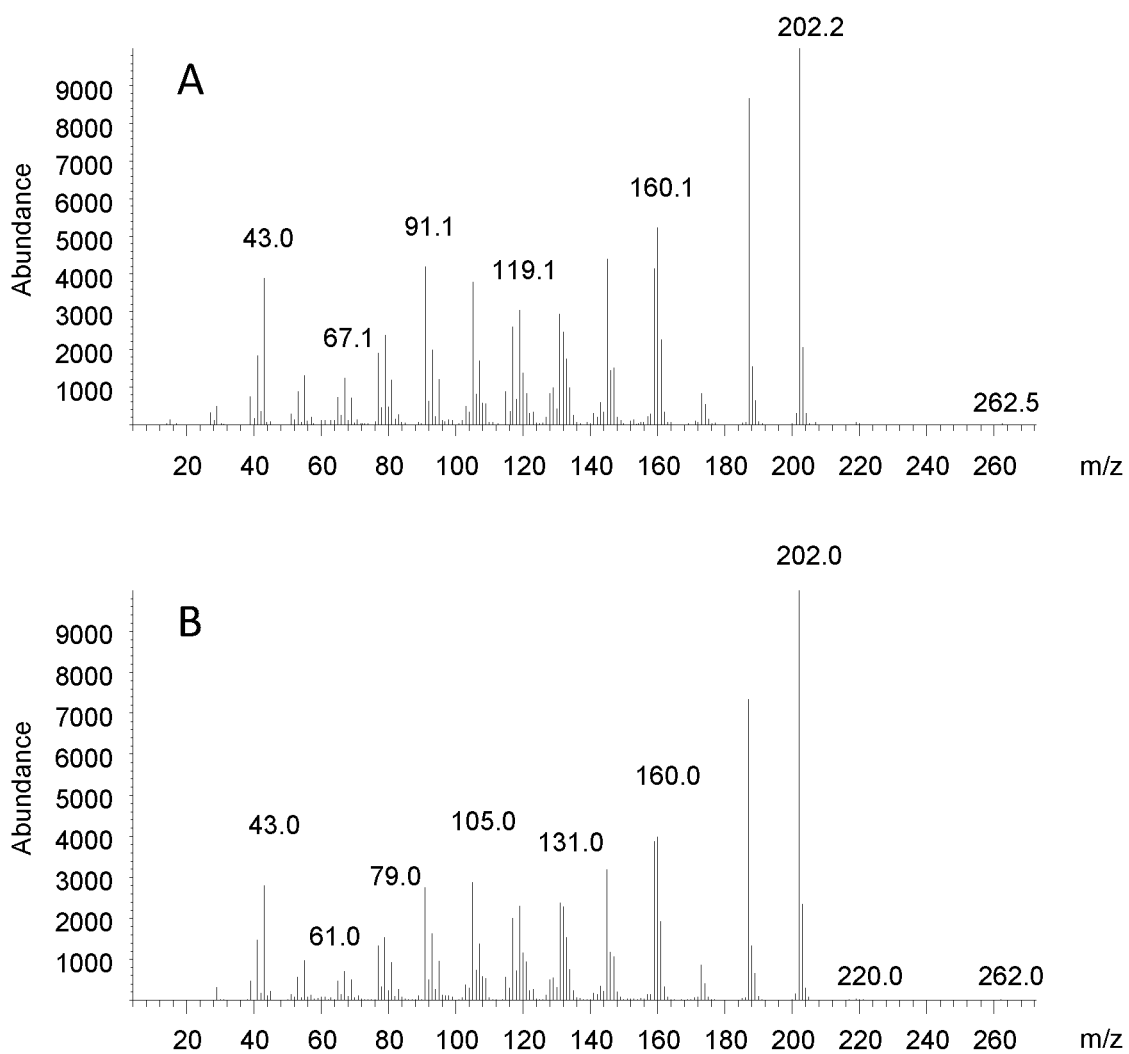
- Figure 8-

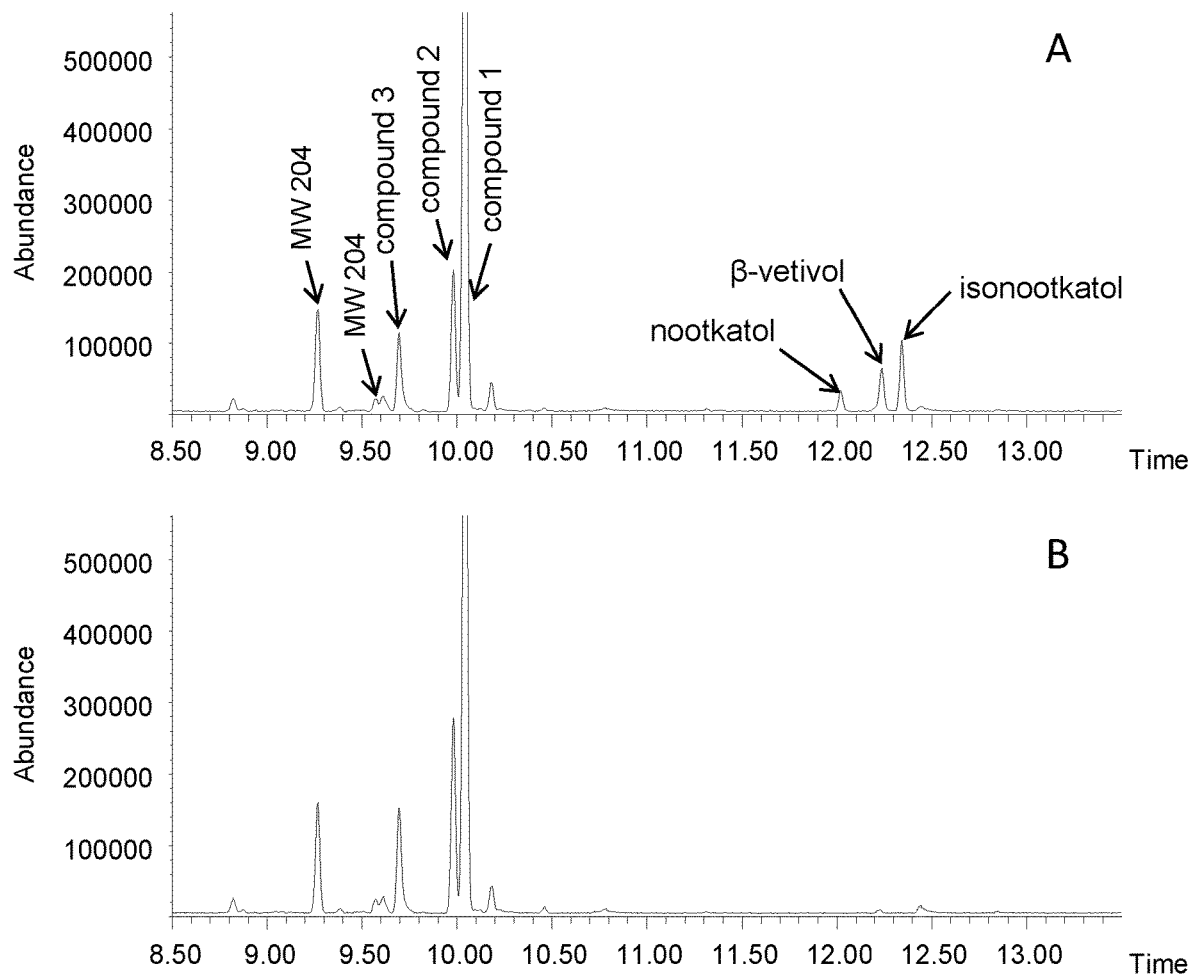
- Figure 9 -

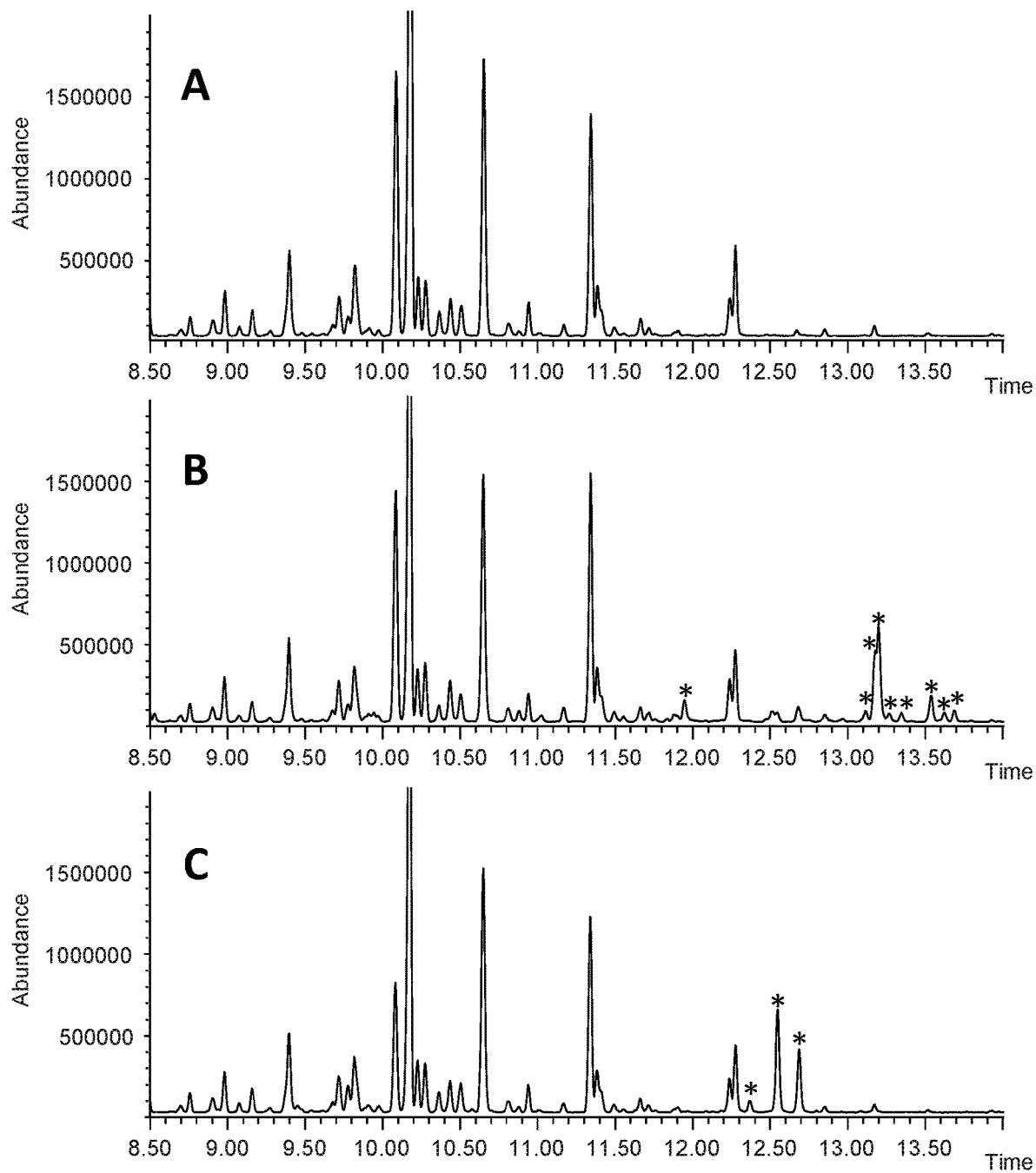
- Figure 10 -

METHODS OF PRODUCING SESQUITERPENE COMPOUNDS

RELATED APPLICATIONS

This application is a national stage application under 35 U.S.C. § 371 of International Patent Application PCT/EP2017/068268, filed 19 Jul. 2017, which claims the benefit of GB patent application 1612609.6, filed 20 Jul. 2016 and EP patent application 17159264.5, filed 3 Mar. 2017.

Submission of Sequence Listing

The Sequence Listing associated with this application is filed in electronic format via EFS-Web and hereby incorporated by reference into the specification in its entirety. The name of the text file containing the Sequence Listing is 9800US_SequenceListing. The size of the text file is 53 KB, and the text file was created on Dec. 5, 2018.

TECHNICAL FIELD

Provided herein are biochemical methods of producing sesquiterpenes, vetiver and related compounds and derivatives.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

SUMMARY

Provided herein is a method of producing one or more sesquiterpene compounds comprising contacting an acyclic farnesyl diphosphate (FPP) precursor with a polypeptide having sesquiterpene synthase activity, wherein the polypeptide comprises an amino acid sequence having at least 55%, 60%, 65%, 70%, 75%, 80%, 85%, 90%, 95%, 98%, 99% or 100% sequence identity to SEQ ID NO: 1, to produce one or more terpenes or a mixture of terpenes. The one or more terpenes can be selected from the group consisting of isovalencene, spirovetiva-1(10),7(11)-diene and valencene; or a mixture of terpenes comprising one or more of isovalencene, spirovetiva-1(10),7(11)-diene and/or valencene. The sesquiterpene synthase activity may comprise one or more of an isovalencene synthase activity, a spirovetiva-1(10),7(11)-diene synthase activity, and/or a valencene synthase activity. The method can further optionally comprise isolating a mixture of terpenes comprising one or more of isovalencene, spirovetiva-1(10),7(11)-diene and/or valencene.

Further provided is a method of producing a sesquiterpene compound or a mixture of terpenes comprising:
a. contacting an acyclic farnesyl diphosphate (FPP) precursor with a polypeptide having terpene synthase activity, wherein the polypeptide comprises a sequence of amino acids that is at least about 55%, 60%, 65%, 70%, 75%, 80%, 85%, 90%, 95%, 98%, 99% or 100% identical to SEQ ID NO: 1, to produce one or more terpenes selected from the group consisting of isovalencene, spirovetiva-1(10),7(11)-diene and valencene, or a mixture of terpenes comprising one or more of of isovalencene, spirovetiva-1(10),7(11)-diene and/or valencene; and
b. optionally isolating one or more terpenes selected from the group consisting of isovalencene, spirovetiva-1(10),7(11)-diene and Valencene, or a mixture of terpenes comprising one or more of of isovalencene, spirovetiva-1(10),7(11)-diene and/or valencene.

Further provided herein is an isolated polypeptide from *Vetiveria zizanoides* (syn. *Chrysopogon zizanioides*) comprising a polypeptide having synthase activity comprising an isovalencene synthase, a spirovetiva-1(10),7(11)-diene synthase and/or a valencene synthase.

Also provided herein is an isolated nucleic acid molecule from *Vetiveria zizanoides* encoding a sesquiterpene synthase having synthase activity comprising isovalencene synthase activity, a spirovetiva-1(10),7(11)-diene synthase activity and/or a valencene synthase activity.

Also provided herein is a nucleic acid isolated or derived from *Vetiveria zizanoides* encoding a polypeptide having sesquiterpene synthase activity.

Also provided is a polypeptide isolated or derived from *Vetiveria zizanoides* having sesquiterpene synthase activity that can be used to produce one or more sesquiterpenes selected from the group consisting of isovalencene, spirovetiva-1(10),7(11)-diene and valencene; or a mixture of sesquiterpenes comprising one or more of isovalencene, spirovetiva-1(10),7(11)-diene and/or valencene.

Also provided herein is a polypeptide wherein the polypeptide comprises a sequence of amino acids that has at least 55%, 60%, 65%, 70%, 75%, 80%, 85%, 90%, 95%, 98%, 99% or 100% sequence identity to SEQ ID NO: 1.

Further provided is the use of a polypeptide as described herein for producing one or more sesquiterpenes selected from the group consisting of isovalencene, spirovetiva-1(10),7(11)-diene and valencene; or a mixture of terpenes comprising one or more of isovalencene, spirovetiva-1(10),7(11)-diene and/or valencene. Also provided is the mixture of terpenes comprising at least two of isovalencene, spirovetiva-1(10),7(11)-diene and/or valencene; or a mixture comprising isovalencene, spirovetiva-1(10),7(11)-diene and valencene.

Further provided herein is a nucleic acid encoding the polypeptides described above.

Further yet provided herein is a nucleic acid of comprising a nucleotide sequence having at least 55%, 60%, 65%70%, 75%, 80%, 85%, 90%, 95%, 98%, 99%, or 100% sequence identity to a sequence selected from the group consisting SEQ ID NO:3 and SEQ ID NO:4.

Provided herein is an isolated cytochrome P450 polypeptide sequence comprising an amino acid sequence having at least 70%, 75%, 80%, 85%, 90%, 95%, 98%, 99%, or 100% sequence identity to SEQ ID NO: 7, SEQ ID NO: 10, SEQ ID NO: 12, or SEQ ID NO: 14. Also provided is an isolated nucleic acid molecule comprising
a) a nucleotide sequence encoding the P450 polypeptide; or
b) a nucleic acid molecule comprising the nucleotide sequence of SEQ ID NO: 6, SEQ ID NO: 8, SEQ ID NO: 9, SEQ ID NO: 11, or SEQ ID NO: 13

Additionally provided is an expression vector comprising one or more of the above nucleic acids, or a nucleic acid encoding the sesquiterpene synthase and a cytochrome P450 enzyme and optionally accompanied by a nucleic acid encoding a cytochrome P450 reductase (CPR) enzyme.

Also provided is a CPR enzyme comprising an amino acid sequence having at least 70%, 75%, 80%, 85%, 90%, 95%, 98%, 99% or 100% sequence identity to SEQ ID NO: 15 that can accompany the P450 polypeptide used in the above methods to produce sesquiterpene derivatives, for example, oxygenated sesquiterpenes.

Also provided is a non-human host organism or cell comprising (1) one or more of the nucleic acid molecule described above, or (2) an expression vector comprising said nucleic acid molecule.

Further provided is the use of an above described sesquiterpene synthase and a cytochrome P450 enzyme for producing an oxygenated sesquiterpene, optionally accompanied by the use of a CPR enzyme.

Also provided is the use of an above described cytochrome P450 enzyme and a sesquiterpene synthase for producing an oxygenated sesquiterpene or a mixture of oxygenated sesquiterpene compounds, optionally accompanied by a heterologously expressed a CPR enzyme.

BRIEF DESCRIPTION OF THE DRAWINGS

FIG. 1A-C. Shows the structures and names of the major products of VzTps1718 and derivatives.

FIG. 2. Shows the GCMS analysis of the sesquiterpenes produced by the recombinant VzTps1718 in an in-vitro assays. A. Total ion chromatogram of the sesquiterpene profile of an incubation of the recombinant VzTps1718 protein with FPP. B. Negative control performed in the same conditions with E. coli cells transformed with an empty plasmid. The peaks corresponding to identified products are indicated: isovalencene (compound 1), spirovetiva-1(10),7(11)-diene (compound 2) and valencene (compound 3). The peaks labeled as MW 204 and MW 222 correspond to sesquiterpene hydrocarbons and sesquiterpene alcohols, respectively for which the structures where not determined. FOH: farnesol produced by hydrolysis of FPP by E. coli endogenous enzymatic activity.

FIG. 3. Shows the mass spectrum of compound 1 in the VzTps1718 product mixture (FIG. 2) and mass spectrum of an isovalencene authentic standard.

FIG. 4. Shows the mass spectrum of compound 2 in the VzTps1718 product mixture (FIG. 2) and mass spectrum of a spirovetiva-1(10),7(11)-diene authentic standard.

FIG. 5. Shows the mass spectrum of compound 3 in the VzTps1718 product mixture (FIG. 2) and mass spectrum of a (+)-valencene authentic standard.

FIG. 6. Shows the GCMS analysis of the sesquiterpenes produced in-vivo by the recombinant VzTps1718 enzyme in engineered bacteria cells. The peaks corresponding to identified products are indicated: isovalencene (compound 1), spirovetiva-1(10),7(11)-diene (compound 2) and valencene (compound 3). The peaks labeled as MW 204 and MW 222 correspond to sesquiterpene hydrocarbons and sesquiterpene alcohols, respectively for which the structures where not determined. FOH: farnesol produced by hydrolysis of FPP by E. coli endogenous enzymatic activity.

FIG. 7. Shows the GCMS analysis of the bioconversion of the sesquiterpene products of VzTps1718 using the *Vetiveria zizanoides* VzCP8201 cytochrome P450 monooxygenase. A, Bioconversion with VzCP8201Bov. B, Bioconversion with VzCP8201-12. C, Negative control using E. coli cells without recombinant P450 enzymes.

FIG. 8. Shows the mass spectrum of the pic at 14.95 minutes in FIGS. 7A and 7B (A) and mass spectrum of an authentic isovalencenyl acetate (B).

FIG. 9. Shows the GCMS analysis of the bioconversion of the sequiterpene products of VzTps1718 using the CYP71D4 cytochrome P450 monooxygenase. A, Bioconversion with CYP71D4opt. B, Negative control using E. coli cells without recombinant P450 enzymes.

FIG. 10. Shows the GCMS analysis of the sesquiterpene compounds produced by E. coli cells engineered to produce the recombinant VzTps1718 sesquiterpene synthase alone (A) or together with a functional VzCP8201 cytochrome P450 enzyme (B) or a functional CYP71D4 cytochrome P450 enzyme (C). The peaks marked with asterisks correspond to the oxygenated compounds produced by the cytochrome P450 enzymes. All other peaks are sesquiterpene compounds produced by the VzTps1718 sesquiterpene synthase.

ABBREVIATIONS USED bp base pair
kb kilo base
DNA deoxyribonucleic acid
cDNA complementary DNA
DTT dithiothreitol
FPP farnesyl-diphosphate
GC gaseous chromatograph
IPTG isopropyl-D-thiogalacto-pyranoside
LB lysogeny broth
MS mass spectrometer
MVA mevalonic acid
PCR polymerase chain reaction
RNA ribonucleic acid
mRNA messenger RNA
miRNA micro RNA
siRNA small interfering RNA
rRNA ribosomal RNA
tRNA transfer RNA Definitions The term "polypeptide" means an amino acid sequence of consecutively polymerized amino acid residues, for instance, at least 15 residues, at least 30 residues, at least 50 residues. In some embodiments provided herein, a polypeptide comprises an amino acid sequence that is an enzyme, or a fragment, or a variant thereof.

The term "isolated" polypeptide refers to an amino acid sequence that is removed from its natural environment by any method or combination of methods known in the art and includes recombinant, biochemical and synthetic methods.

The term "protein" refers to an amino acid sequence of any length wherein amino acids are linked by covalent peptide bonds, and includes oligopeptide, peptide, polypeptide and full length protein whether naturally occurring or synthetic.

The terms "biological function," "function," "biological activity" or "activity" refer to the ability of the sesquiterpene synthase to catalyze the formation of one or more sesquiterpene compounds or a mixture comprising one or more sesquiterpenes.

The terms "mixture of terpenes" or "mixture of sesquiterpenes" refer to a mixture of terpenes or sesquiterpenes that comprises one or more of isovalencene, spirovetiva-1(10), 7(11)-diene and/or valencene, and wherein the mixture may also comprise additional terpenes or sesquiterpenes.

The terms "nucleic acid sequence," "nucleic acid," and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U).

An "isolated nucleic acid" or "isolated nucleic acid sequence" is defined as a nucleic acid or nucleic acid sequence that is in an environment different from that in which the nucleic acid or nucleic acid sequence naturally occurs. The term "naturally-occurring" as used herein as applied to a nucleic acid refers to a nucleic acid that is found in a cell in nature. For example, a nucleic acid sequence that is present in an organism, for instance in the cells of an organism, that can be isolated from a source in nature and which it has not been intentionally modified by a human in the laboratory is naturally occurring.

"Recombinant nucleic acid sequence" are nucleic acid sequences that result from the use of laboratory methods (molecular cloning) to bring together genetic material from more than on source, creating a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002 Cold Spring Harbor Lab Press; and Sambrook et al., 1989 Cold Spring Harbor, N.Y.: Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

A "chimeric gene" refers to any gene, which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises for example a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein. "Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site. The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of a sesquiterpene synthase in the organism.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule. The host cell is particularly a bacterial cell, a fungal cell or a plant cell. The host cell may contain a recombinant gene which has been integrated into the nuclear or organelle genomes of the host cell. Alternatively, the host may contain the recombinant gene extrachromosomally. Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The term "organism" refers to any non-human multicellular or unicellular organisms such as a plant, or a micro-organism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

For the descriptions herein and the appended claims, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

DETAILED DESCRIPTION

In one embodiment, provided herein is a method of producing a sesquiterpene compound comprising:
 a. contacting an acyclic farnesyl diphosphate (FPP) precursor with a polypeptide having a terpene synthase activity from the group consisting of an isovalencene synthase activity, a spirovetiva-1(10),7(11)-diene synthase activity and a valencene synthase activity,
  wherein the polypeptide comprises
   a sequence of amino acids that has at least a sequence that is at least about 55%, 60%, 65%, 70%, 75%, 80%, 85%, 90%, 95%, 98%, 99% or 100% identical to SEQ. ID. NO: 1, to produce a terpene selected from the group consisting of isovalencene, spirovetiva-1(10),7(11)-diene and valencene; and
 b. optionally isolating the terpene selected from the group consisting of isovalencene, spirovetiva-1(10),7(11)-diene and Valencene.

In one embodiment, provided herein is a method of producing one or more sesquiterpene compounds comprising contacting an acyclic farnesyl diphosphate (FPP) precursor with a polypeptide having sesquiterpene terpene synthase activity, wherein the polypeptide comprises an amino acid sequence having at least 55%, 60%, 65%, 70%, 75%, 80%, 85%, 90%, 95%, 98%, 99% or 100% sequence identity to SEQ ID NO: 1, to produce one or more terpenes selected from the group consisting of isovalencene, spirovetiva-1(10),7(11)-diene and valencene; or a mixture of sesquiterpenes comprising one or more of isovalencene, spirovetiva-1(10),7(11)-diene and/or valencene; and optionally, isolating the one or more sesquiterpenes selected from the group consisting of isovalencene, spirovetiva-1(10),7 (11)-diene and valencene; or the mixture of sesquiterpenes comprising one or more of isovalencene, spirovetiva-1(10),7(11)-diene and/or valencene.

In one embodiment, a method provided herein comprises the steps of transforming a host cell or non-human host organism with a nucleic acid encoding a polypeptide having a sesquiterpene synthase activity, wherein the polypeptide comprises an amino acid sequence having at least 55%, 60%, 65%, 70%, 75%, 80%, 85%, 90%, 95%, 98%, 99% or 100% sequence identity to SEQ ID NO: 1.

In one embodiment, a method provided herein comprises the steps of transforming a host cell or non-human organism with a nucleic acid encoding a polypeptide having a terpene synthase activity from the group consisting of an isovalencene synthase activity, a spirovetiva-1(10),7(11)-diene synthase activity and a valencene synthase activity wherein the polypeptide comprises a sequence of amino acids that has at least 55%, 60%, 65%, 70%, 75%, 80%, 85%, 90%, 95%, 98%, 99% or 100% sequence identity to a polypeptide selected from the group consisting of SEQ ID NO:1.

In one embodiment, a method provided herein comprises cultivating a non-human host organism or cell capable of producing FPP and transformed to express a polypeptide wherein the polypeptide comprises a sequence of amino acids that has at least 55%, 60%, 65%, 70%, 75%, 80%, 85%, 90%, 95%, 98%, 99% or 100% sequence identity to SEQ ID NO: 1.

In a further embodiment, the human host organism or cell comprises a prokaryotic cell and more particularly a bacterial cell and even more particularly *E. coli*.

In one embodiment, the non-human host organism or cell is a eukaryotic cell. In another embodiment, the non-human host organism or cell is a yeast cell. In a further embodiment, the non-human host organism or cell is *Saccharomyces cerevisiae*.

In a further embodiment, the non-human organism or cell is a plant cell.

In a another embodiment, a method provided herein comprises contacting a sesquiterpene from the group consisting of isovalencene, spirovetiva-1(10),7(11)-diene and valencene with at least one enzyme to produce a sesquiterpene derivative.

In one embodiment, a method is provided comprising oxidizing a sesquiterpene to a derivative using a chemical or biochemical synthesis or a combination of both. In a particular method, the oxidation is performed with a cytochrome P450 enzyme. In one embodiment the P450 enzyme is selected from a P450 isolated or derived from *Vetiveria zizanoides*. In a further embodiment, the P450 enzyme is selected from the CYP71D family of enzymes. In a yet further embodiment, a compound generated from use of the synthases provided herein are oxidized using a wild type enzyme selected from a prokaryotic or a eukaryotic cell.

In one embodiment, the nucleic acid encoding the P450 enzyme used for oxidation of a sesquiterpene can be found in the same plasmid or in a separate plasmid or expression vector in the same cell that includes the nucleic acid encoding the sesquiterpene synthase.

In another embodiment, the P450 can be in one cell and the sesquiterpene synthase in another cell but together in a culture or co-cultured for oxidation of the one or more terpenes or mixture of terpenes. In yet a further embodiment, the sesquiterpenes can first be produced then a cell comprising the P450 or a P450 produced by a cell can be provided for oxidation of the sesquiterpene.

To reconstitute the activity of the P450 enzyme, a cytochrome P450-reductase (CPR) is involved in the transfer of electrons from the cofactor NADPH (reduced Nicotinamide adenine dinucleotide phosphate) to the P450 enzyme active site. Therefore, in a further embodiment, the method is performed using a cytochrome P450 enzyme in combination with a CPR enzyme. In a further embodiment, the CPR is isolated or is derived from *Mentha piperita*.

In a further embodiment, the enzymes provided herein are heterologously expressed in a cell.

In one embodiment, the P450 enzymes and the terpene synthases provided herein are expressed or overexpressed in the same cell. In a further embodiment, the P450 enzymes and the terpene synthases and the CPR enzymes provided herein are expressed or overexpressed in the same cell.

In one embodiment, provided is the use of an above described sesquiterpene synthase and a cytochrome P450 enzyme for producing an oxygenated sesquiterpene, optionally accompanied by the use of a CPR enzyme.

In a further embodiment, provided herein is the use of a sesquiterpene synthase and an above described cytochrome P450 enzyme for producing an oxygenated sesquiterpene or a mixture of oxygenated sesquiterpene compounds, optionally accompanied by a heterologously expressed a CPR enzyme.

In one aspect, provided herein is a method of producing an oxygenated sesquiterpene comprising oxidizing a sesquiterpene to an oxygenated sesquiterpene using a chemical or biochemical synthesis or a combination of both with a cytochrome P450 polypeptide described herein and accompanied by a CPR enzyme.

In one embodiment, provided herein is a mixture of terpenes comprising isovalencene, spirovetiva-1(10),7(11)-diene and valencene.

In one embodiment, provided herein is a mixture of terpenes comprising isovalencene, spirovetiva-1(10),7(11)-diene and valencene wherein the proportions relative to each other, by weight, are about 66 to 68% of isovalencene, about 25 to 26% of spirovetiva-1(10),7(11)-diene and about 6 to 9% of valencene. Also provided herein is a mixture of terpenes comprising isovalencene derivatives, spirovetiva-1(10),7(11)-diene derivatives and valencene derivatives wherein the proportions relative to each other, by relative weight, are about 66 to 68% of isovalencene derivatives, about 25 to 26% of spirovetiva-1(10),7(11)-diene derivatives and about 6 to 9% of valencene derivatives In one embodiment, provided herein is an expression vector comprising a nucleic acid that codes for the polypeptides (synthase) described herein.

In one embodiment, provided herein is a non-human host organism or cell transformed to harbor at least one nucleic acid described herein so that it heterologously expresses or over-expresses at least one polypeptide (synthase) provided herein.

In one embodiment, provided herein is a non-human host organism or host cell comprising (1) a nucleic acid molecule encoding a polypeptide having sesquiterpene synthase activity as described herein, or (2) an expression vector comprising said nucleic acid molecule.

In one embodiment the non-human host organism or host cell is a eukaryotic cell. In another embodiment, the non-human organism or cell is a fungus. In a further embodiment, the non-human organism or cell is a plant cell. In still yet another embodiment, the non-human host organism or cell is a microorganism. In another embodiment the non-human host organism or cell is a bacteria. In a further embodiment, the non-human host organism or cell is *E. coli*. In one embodiment, the non-human organism or cell is a yeast. In a further embodiment, the non-human host organism or cell is *Saccharomyces cerevisiae*.

In one embodiment, provided herein is a nucleic acid isolated or derived from *Vetiveria zizanoides* encoding a polypeptide having sesquiterpene synthase activity.

Another embodiment is a polypeptide isolated or derived from *Vetiveria zizanoides* having sesquiterpene synthase activity.

In a further embodiment, provided herein is the use of a polypeptide having sesquiterpene synthase activity to produce one or more sesquiterpenes selected from the group consisting of isovalencene, spirovetiva-1(10),7(11)-diene and valencene; or a mixture of sesquiterpenes comprising one or more of isovalencene, spirovetiva-1(10),7(11)-diene and/or valencene.

In yet another embodiment, provided herein is the use of the polypeptide having a sesquitepene synthase activity for producing a mixture of sesquiterpene compounds comprising one or more of isovalencene, spirovetiva-1(10),7(11)-diene and/or valencene.

In one embodiment a polypeptide having a sesquiterpene synthase activity comprises an amino acid sequence having at least 55%, 60%, 65%, 70%, 75%, 80%, 85%, 90%, 95%, 98%, 99% or 100% sequence identity to SEQ ID NO: 1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 55%, 60%, 65%, 70%, 75%, 80%, 85%, 90%, 95%, 98%, 99% or 100% identical to SEQ ID NO: 1.

In one embodiment, a polypeptide having a terpene synthase activity comprising an isovalencene synthase activity, a spirovetiva-1(10),7(11)-diene synthase activity and/or a valencene synthase activity comprises a sequence of amino acids that has at least a sequence that is at least about 60%, 65%, 70%, 75%, 80%, 85%, 90%, 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 65%, 70%, 75%, 80%, 85%, 90%, 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 70%, 75%, 80%, 85%, 90%, 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 75%, 80%, 85%, 90%, 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 80%, 85%, 90%, 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 85%, 90%, 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 90%, 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 95%, 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 98%, 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is at least about 99% or 100% identical to SEQ ID NO:1.

In one embodiment a polypeptide having a terpene synthase activity from the group consisting of an isovalencene synthase activity, a spirovetiva-1(10),7(11)-diene synthase activity and a valencene synthase activity comprises a sequence of amino acids that has at least a sequence that is identical to SEQ ID NO: 1.

In one embodiment a nucleic acid comprises a nucleotide sequence having at least 55%, 60%, 65%70%, 75%, 80%, 85%, 90%, 95%, 98%, 99%, or 100% sequence identity to a sequence selected from the group consisting SEQ ID NO: 3 and SEQ ID NO: 4.

In one embodiment a nucleic acid comprises a nucleotide sequence having at least 60%, 65%, 70%, 75%, 80%, 85%, 90%, 95%, 98%, 99%, or 100% sequence identity to a sequence selected from the group consisting SEQ ID NO: 3 and SEQ ID NO: 4.

In one embodiment a nucleic acid comprises a nucleotide sequence having at least 65%, 70%, 75%, 80%, 85%, 90%, 95%, 98%, 99%, or 100% sequence identity to a sequence selected from the group consisting SEQ ID NO:3 and SEQ ID NO: 4.

In one embodiment a nucleic acid comprises a nucleotide sequence having at least 70%, 75%, 80%, 85%, 90%, 95%, 98%, 99%, or 100% sequence identity to a sequence selected from the group consisting SEQ ID NO: 3 and SEQ ID. NO: 4.

In one embodiment a nucleic acid comprises a nucleotide sequence having at least 75%, 80%, 85%, 90%, 95%, 98%, 99%, or 100% sequence identity to a sequence selected from the group consisting SEQ ID NO: 3 and SEQ ID. NO: 4.

In one embodiment a nucleic acid comprises a nucleotide sequence having at least 80%, 85%, 90%, 95%, 98%, 99%, or 100% sequence identity to a sequence selected from the group consisting SEQ ID NO: 3 and SEQ ID NO: 4.

In one embodiment a nucleic acid comprises a nucleotide sequence having at least 85%, 90%, 95%, 98%, 99%, or 100% sequence identity to a sequence selected from the group consisting SEQ ID NO: 3 and SEQ ID NO: 4.

In one embodiment a nucleic acid comprises a nucleotide sequence having at least 90%, 95%, 98%, 99%, or 100% sequence identity to a sequence selected from the group consisting SEQ ID NO: 3 and SEQ ID NO: 4.

In one embodiment a nucleic acid comprises a nucleotide sequence having at least 95%, 98%, 99%, or 100% sequence identity to a sequence selected from the group consisting SEQ ID NO: 3 and SEQ ID. NO: 4.

In one embodiment a nucleic acid comprises a nucleotide sequence having at least 98%, 99%, or 100% sequence identity to a sequence selected from the group consisting SEQ ID NO: 3 and SEQ ID NO: 4.

In one embodiment a nucleic acid comprises a nucleotide sequence having at least 99%, or 100% sequence identity to a sequence selected from the group consisting SEQ ID NO: 3 and SEQ ID NO: 4.

In one embodiment a nucleic acid comprises a nucleotide sequence having a sequence that is identical to a sequence selected from the group consisting SEQ ID NO: 3 and SEQ ID NO: 4.

In one embodiment, the nucleic acid comprises SEQ ID NO: 3. In a further embodiment, the nucleic acid comprises SEQ ID NO: 4.

In one embodiment, a compound made from a terpene synthase provided herein is oxidized with a P450 enzyme having a sequence that is 70%, 75%, 80%, 85%, 90%, 95%, 98%, 99% or 100% identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme having a sequence that is 75%, 80%, 85%, 90%, 95%, 98%, 99% or 100% identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme having a sequence that is 80%, 85%, 90%, 95%, 98%, 99% or 100% identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme having a sequence that is 85%, 90%, 95%, 98%, 99% or 100% identical to a P450 enzyme (e.g., but not limited to, an enzyme having a P450 activity) selected from the group consisting of SEQ ID NO.: 7, SEQ ID NO: 10, SEQ ID NO: 12 and SEQ ID NO: 14.

In one embodiment, a compound made from a terpene synthase provided herein is oxidized with a P450 enzyme having a sequence that is 90%, 95%, 98%, 99% or 100% identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme having a sequence that is 95%, 98%, 99% or 100% identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme having a sequence that is 98%, 99% or 100% identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme having a sequence that is 99% or 100% identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme having a sequence that is identical to a P450 enzyme (e.g., but not limited to, an enzyme having a P450 activity) selected from the group consisting of SEQ ID NO: 7, SEQ ID NO: 10, SEQ ID NO: 12 and SEQ ID NO: 14.

In one embodiment, a compound made from a terpene synthase provided herein is oxidized with a P450 enzyme comprising SEQ ID NO: 7.

In one embodiment, a compound made from a terpene synthase provided herein is oxidized with a P450 enzyme comprising SEQ ID NO: 10.

In one embodiment, a compound made from a terpene synthase provided herein is oxidized with a P450 enzyme comprising SEQ ID NO: 12.

In one embodiment, a compound made from a terpene synthase provided herein is oxidized with a P450 enzyme comprising SEQ ID NO: 14.

In one embodiment, the P450 enzyme is accompanied by a cytochrome P450 reductase (CPR) enzyme. The CPR enzyme may be derived from the same plant source as the P450 enzyme or from a different plant source to the P450 enzyme. In one embodiment, a CPR derived from a different plant source is used to complement the activity of the P450 enzyme as described in Jensen and Moller (2010) *Phytochemsitry* 71, 132-141. In one embodiment, the CPR is isolated or is derived from *Mentha piperita*.

In a further embodiment, the CPR enzyme has a sequence that is 70%, 75%, 80%, 85%, 90%, 95%, 98%, 99% or 100% identical to a CPR enzyme (e.g., but not limited to, an enzyme having a CPR activity) selected from the group consisting of SEQ ID NO: 15. In a further embodiment, the CPR enzyme has a sequence that is identical to a CPR enzyme (e.g., but not limited to, an enzyme having a CPR activity) selected from the group consisting of SEQ ID NO: 15. In a further embodiment, the CPR enzyme comprises SEQ ID NO: 15.

The ability of a polypeptide to catalyze the synthesis of sesquiterpenes or of a particular sesquiterpene can be confirmed by performing the enzyme assay as detailed in the Examples provided herein.

Polypeptides are also meant to include truncated polypeptides provided that they keep their sesquiterpene synthase activity. A nucleotide sequence obtained by modifying the sequences described herein may be performed using any method known in the art, for example by introducing any type of mutations such as deletion, insertion or substitution mutations. Examples of such methods are cited in the part of the description relative to the variant polypeptides and the methods to prepare them.

The percentage of identity between two peptide or nucleotide sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web. Preferably, the BLAST program (Tatiana et al, *FEMS Microbiol Lett.*, 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic and sequences and to calculate the percentage of sequence identity.

The polypeptide to be contacted with FPP in vitro can be derived from or obtained by extraction from any organism expressing it, using standard protein or enzyme extraction technologies. If the host organism is a unicellular organism or cell releasing the polypeptide of an embodiment herein into the culture medium, the polypeptide may simply be obtained directly from the culture medium, or collected by centrifugation, optionally followed by washing steps and re-suspension in suitable buffer solutions. If the organism or cell accumulates the polypeptide within its cells, the polypeptide may be obtained by disruption or lysis of the cells and optionally through further extraction of the polypeptide from the cell lysate.

According to another particularly embodiment, the method of any of the above-described embodiments is carried out in vivo. These embodiments provided herein are particularly advantageous since it is possible to carry out the method in vivo without previously isolating the polypeptide. The reaction occurs directly within the organism or cell transformed to express said polypeptide.

The organism or cell is meant to "express" a polypeptide, provided that the organism or cell is transformed to harbor a nucleic acid encoding said polypeptide, this nucleic acid is transcribed to mRNA and the polypeptide is found in the host organism or cell. The term "express" encompasses "heterologously express" and "over-express", the latter referring to levels of mRNA, polypeptide and/or enzyme activity over and above what is measured in a non-transformed organism or cell. A more detailed description of suitable methods to transform a non-human host organism or cell will be described later on in the part of the specification that is dedicated to such transformed non-human host organisms or cells.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP". Methods to transform organisms, for example microorganisms, so that they produce FPP are already known in the art.

Non-human host organisms suitable to carry out the method of an embodiment herein in vivo may be any non-human multicellular or unicellular organisms. In a particular embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In a more particular embodiment the non-human host organism used to carry out the method of an embodiment herein in vivo is a microorganism. Any microorganism can be used but according to an even more particular embodiment said microorganism is a bacteria or yeast. In further embodiments, said bacteria is *E. coli* and said yeast is *Saccharomyces cerevisiae*.

Some of these organisms do not produce FPP naturally or only in small amounts. To be suitable to carry out the method of an embodiment herein, these organisms can be transformed to produce said precursor or to produce said precursor in larger amounts. They can be so transformed before the modification with the nucleic acid described according to any of the above embodiments. They can also be transformed simultaneously, as explained above.

Isolated higher eukaryotic cells can also be used, instead of complete organisms, as hosts to carry out the method of an embodiment herein in vivo. Suitable eukaryotic cells may include any non-human cell, plant or fungal cells.

According to another particular embodiment, the polypeptides having a sesquiterpene synthase activity used in any of the embodiments described herein or encoded by the nucleic acids described herein may be variants obtained by genetic engineering, provided that said variant keeps its sesquiterpene synthase activity.

As used herein, the polypeptide is intended as a polypeptide or peptide fragment that encompasses the amino acid sequences identified herein, as well as truncated or variant polypeptides, provided that they keep their sesquiterpene synthase activity.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Accordingly, encompassed herein are methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously be used in the methods of an embodiment herein.

As mentioned above, the nucleic acid encoding the polypeptide of an embodiment herein is a useful tool to modify non-human host organisms or cells intended to be used when the method is carried out in vivo.

A nucleic acid encoding a polypeptide according to any of the above-described embodiments is therefore also provided herein.

The nucleic acid of an embodiment herein can be defined as including deoxyribonucleotide or ribonucleotide polymers in either single- or double-stranded form (DNA and/or RNA). The terms "nucleotide sequence" should also be understood as comprising a polynucleotide molecule or an oligonucleotide molecule in the form of a separate fragment or as a component of a larger nucleic acid. Nucleic acids of an embodiment herein also encompass certain isolated nucleotide sequences including those that are substantially free from contaminating endogenous material. The nucleic acid of an embodiment herein may be truncated, provided that it encodes a polypeptide encompassed herein, as described above.

In one embodiment, the nucleic acid of an embodiment herein that encodes a synthase can be present naturally in a plant such as *Vetiveria zizanoides* or other species, derived from *Vetiveria zizanoides* or other species or obtained by modifying SEQ ID NO: 3 or SEQ ID NO: 4.

Mutations may be any kind of mutations of these nucleic acids, such as point mutations, deletion mutations, insertion mutations and/or frame shift mutations. A variant nucleic acid may also be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the terpene synthase may be optimized for increased expression in the host cell. For example, nucleotides of an embodiment herein may be synthesized using codons particular to a host for improved expression.

A variant may also differ from the polypeptide of an embodiment herein by attachment of modifying groups which are covalently or non-covalently linked to the polypeptide backbone.

The variant also includes a polypeptide which differs from the polypeptide described herein by introduced N-linked or O-linked glycosylation sites, and/or an addition of cysteine residues. The skilled artisan will recognize how to modify an amino acid sequence and preserve biological activity.

In addition to the gene sequences shown in the sequences disclosed herein, it will be apparent for the person skilled in the art that DNA sequence polymorphisms may exist within a given population, which may lead to changes in the amino acid sequence of the polypeptides disclosed herein. Such genetic polymorphisms may exist in cells from different populations or within a population due to natural allelic variation. Allelic variants may also include functional equivalents.

Further embodiments also relate to the molecules derived by such sequence polymorphisms from the concretely disclosed nucleic acids. These natural variations usually bring about a variance of about 1 to 5% in the nucleotide sequence of a gene or in the amino acid sequence of the polypeptides disclosed herein. As mentioned above, the nucleic acid encoding the polypeptide of an embodiment herein is a useful tool to modify non-human host organisms or cells and to modify non-human host organisms or cells intended to be used in the methods described herein.

Embodiments provided herein include, but are not limited to cDNA, genomic DNA and RNA sequences.

Genes, including the polynucleotides of an embodiment herein, can be cloned on basis of the available nucleotide sequence information, such as found in the attached sequence listing and by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermostable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli*.

Provided herein are nucleic acid sequences obtained by mutations of SEQ ID NO: 3 and SEQ ID NO: 4; such mutations can be routinely made. It is clear to the skilled artisan that mutations, deletions, insertions, and/or substitutions of one or more nucleotides can be introduced into these DNA sequence The nucleic acid sequences of an embodiment herein encoding an isovalencene synthase, a spirovetiva-1(10),7 (11)-diene synthase and a valencene synthase proteins can be inserted in expression vectors and/or be contained in chimeric genes inserted in expression vectors, to produce an isovalencene synthase, a spirovetiva-1(10),7(11)-diene synthase and a valencene synthase in a host cell or host organism. The vectors for inserting transgenes into the genome of host cells are well known in the art and include plasmids, viruses, cosmids and artificial chromosomes. Binary or co-integration vectors into which a chimeric gene is inserted are also used for transforming host cells.

Another important tool for transforming host organisms or cells suitable to carry out the method of an embodiment herein in vivo is an expression vector comprising a nucleic acid according to any embodiment of an embodiment herein. Such a vector is therefore also provided herein.

Recombinant non-human host organisms and cells transformed to harbor at least one nucleic acid of an embodiment herein so that it heterologously expresses or over-expresses at least one polypeptide of an embodiment herein are also very useful tools to carry out the method of an embodiment herein. Such non-human host organisms and cells are therefore also provided herein.

A nucleic acid according to any of the above-described embodiments can be used to transform the non-human host organisms and cells and the expressed polypeptide can be any of the above-described polypeptides.

Non-human host organisms of an embodiment herein may be any non-human multicellular or unicellular organisms. In a particular embodiment, the non-human host organism is a plant, a prokaryote or a fungus. Any plant, prokaryote or fungus is suitable to be transformed according to the methods provided herein. Particularly useful plants are those that naturally produce high amounts of terpenes.

In a more particular embodiment the non-human host organism is a microorganism. Any microorganism is suitable to be used herein, but according to an even more particular embodiment said microorganism is a bacteria or yeast. Most particularly, said bacteria is *E. coli* and said yeast is *Saccharomyces cerevisiae*.

Isolated higher eukaryotic cells can also be transformed, instead of complete organisms. As higher eukaryotic cells, we mean here any non-human eukaryotic cell except yeast cells. Particular higher eukaryotic cells are plant cells or fungal cells.

Any of the embodiments described hereinabove may be combined with any appropriate statement of the invention in any workable combination. Embodiments are not intended to be restricted to any particular statement of invention, except where stated.

The invention will now be further described with reference to the following Examples and accompanying Figures.

EXAMPLES

Example 1

Plant Material and Total RNA Extraction

Vetiver (*Vetiveria zizanoides*) plants were obtained from a plant nursery (The Austral Plants Company, Les Avirons, The Reunion Island, France). The plants were cultivated in pots in a greenhouse (Lullier Agronomy research Station, Geneva, Switzerland) and were propagated vegetatively by dividing six months to one-year-old clumps. For harvesting of the roots, the plants were removed from the pots and rinsed with tap water.

For extraction of RNA, roots from several plants were combined, including young plants (4 to 6 months after propagation), old plants with a well-developed dense root system (1 to 2 years after propagation) and young plants dried at room temperature for 24 to 36 hours after being removed from the pots. The roots were cut off from the aerial part of the plants and frozen in liquid nitrogen. The roots were first roughly chopped in liquid nitrogen using a Waring Blendor (Waring Laboratory, Torrington, USA) and then ground to a fine powder using a mortar and pestle. Total RNA was extracted following the procedure described in Kolosova et al (Kolosova N, Miller B, Ralph S, Ellis B E, Douglas C, Ritland K, and Bohlmann J, Isolation of high-quality RNA from gymnosperm and angiosperm trees. *J. Biotechniques*, 36(5), 821-4, 2004) with the following modifications. A volume of 20 ml of extraction buffer was used for 2 grams of ground tissue and the extraction buffer was supplemented with 2% (w/v) of PVP (polyvinylpyrrolidone, Sigma-Aldrich). For the CTAB (cethyltrimethylammonium bromide, Sigma-Aldrich) extraction step, the nucleic acid pellet was resuspended in 2 ml TE buffer (10 mM Tris-HCl, pH 8, 1 mM EDTA) and the extraction was performed with 2 ml of 5M NaCl and 1 ml 10% CTAB. For the isopropanol precipitation, the nucleic acid pellet was dissolved in 500 µl TE. The final RNA pellet was resuspended in 50 µl water.

Example 2

Transcriptome Sequencing

The Vetiver roots transcriptome was sequenced using the Illumina technology. All sequencing steps were performed by Fasteris SA (Plan-les-Ouates, CH-1228, Switzerland). The mRNA library was prepared using the TruSeq Stranded mRNA Library Preparation Kit (Illumina Inc.). The fragmentation and size selection were adapted to select and purify DNA fragments between 500 and 550 bp of length. The DNA sequencing was performed on a MiSeq sequencer using the MiSeq Reagent Kit V3 (Illumina Inc.). One full flow cell was used for the sequencing of the library and 2×300 sequencing cycles were performed. This sequencing provided 17'453'393 of 2×300 overlapping paired reads (10.5 mega bases in total).

The paired reads were first preprocessed using FastqJoin to join paired-end reads on the overlapping ends. In this step 58.3% of the paired-end reads could be joined and 8.5 millions of joined-reads with an average size of 430 bases were obtained. These new reads as well as the non-joined paired-end reads were then assembled using the CLC bio de novo assembly tool of the CLC Genombic Workbench 7 (CLC bio). Finally, the assembled vetiver roots transcriptome contained 333'633 unique contig sequences with an average length of 577 bases, a maximum length of 15'800 bases and an N50 of 546 bases.

Example 3

Identification of a New Sesquiterpene Encoding Sequences

The transcriptome data were searched using the tBlastn algorithm (Altschul et al, J. Mol. Biol. 215, 403-410, 1990) and using as query the amino acid sequences of known sesquiterpene synthases isolated from the same plants and described previously (WO2010134004 and WO2006134523). Using this approach a new sesquiterpene encoding sequence was obtained. This cDNA (VzTps1718) (SEQ ID NO: 3) was 1835 base-pairs long and contained an open reading frame encoding for a 567 amino acid length protein (SEQ ID NO: 1).

The VzTp1718 deduced amino acid sequence was compared to publicly available sequences. The closest amino acid sequence in public databases was the sequence with the NCBI Accession Number XP_0049797111 This sequence is annotated as a (S)-beta-bisabolene synthase-like and was isolated from the plant Setaria italica. However the functional annotation of XP_004979711.1 was made by automated annotation and experimental data are not disclosed to confirm the enzymatic activity of this enzyme. This amino acid sequence XP_004979711.1 shares only 54% identity with the VzTps1718 amino acid sequence.

Comparison with the sesquiterpene synthases previously characterized from vetiver roots (WO2010134004 and WO2006134523) shows less than 35% sequence identity of the amino acid sequences.

Example 4

Heterologous Expression and Functional Characterization of VzTps1718

The DNA sequence of VzTps1718 was first codon-optimized (SEQ ID NO: 4), synthesized in-vitro and cloned in the pJ401 expression plasmid (DNA2.0, Menlo Park, Calif., USA). Heterologous expression of the VzTps1718 synthases (SEQ ID NO: 1) was performed in KRX *E. coli* cells (Promega). Single colonies of cells transformed with the pJ401-VzTps1718 expression plasmid were used to inoculate 5 ml LB medium. After 5 to 6 hours incubation at 37° C., the cultures were transferred to a 25° C. incubator and left 1 hour for equilibration. Expression of the protein was then induced by the addition of 1 mM IPTG and 0.2% rhamnose and the culture was incubated over-night at 25° C. The next day, the cells were collected by centrifugation, resuspended in 0.1 volume of 50 mM MOPSO pH 7, 10% glycerol and lyzed by sonication. The extracts were cleared by centrifugation (30 min at 20,000 g) and the supernatants containing the soluble proteins were used for further experiments.

This crude *E. coli* protein extracts containing the recombinant protein were used for the characterization of the enzymatic activities. The assays were performed in 2 mL of 50 mM MOPSO pH 7, 10% glycerol, 1 mM DTT, 15 mM MgCl2 in the presence of 80 µM of farnesyl-diphosphate (FPP, Sigma) and 0.1 to 0.5 mg of crude protein. The tubes were incubated 12 to 24 hours at 25° C. and extracted twice with one volume of pentane. After concentration under a nitrogen flux, the extracts were analysed by GC-MS and compared to extracts from assays with control proteins. The GC-MS analysis were performed using an Agilent 6890 Series GC system connected to an Agilent 5975 mass detector. The GC was equipped with 0.25 mm inner diameter by 30 m DB-1MS capillary column (Agilent). The carrier gas was He at a constant flow of 1 mL/min. The inlet temperature was set at 250° C. The initial oven temperature was 80° C. followed by a gradient of 10° C./min to 220° C. and a second gradient of 30° C./min to 280° C. The identification of the products was based on the comparison of the mass spectra and retention indices with authentic standards and internal mass spectra databases.

In this in-vitro conditions, the VzTps1718 enzyme (SEQ ID NO: 1) showed sesquiterpene synthase activity and converted FPP to several terpene products including sesquiterpene hydrocarbons and oxygenated sesquiterpenes. The major products were sesquiterpenes with the eremophilane, vetispirane and eudesmane skeleton. Amongst the products, some compounds could be identified based on the coincidence of the retention index and mass spectrum: isovalencene (compound 1), spirovetiva-1(10),7(11)-diene (compound 2) and valencene (compound 3) (FIG. 1). The relative composition of the product mixture obtained in-vitro with VzTps1718 is detailed in table 1. For the identified sesquiterpene products, the relative abundance in the product mixture was 15.6% for spirovetiva-1(10),7(11)-diene, 41.6% for isovalencene and 3.7% for valencene.

mevalonate (MVA) pathway were expressed in the same cells. The construction of the expression plasmid containing an FPP synthase gene and the gene for a complete MVA pathway was described in patent WO2013064411 or in Schalk et al (2013) J. Am. Chem. Soc. 134, 18900-18903. Briefly, an expression plasmid was prepared containing two operons composed of the genes encoding the enzymes for a complete mevalonate pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in-vitro (DNA2.0, Menlo Park, Calif., USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC-29258-4506. This plasmid thus contains the genes encoding all enzymes of the biosynthetic pathway leading from acetyl-coenzyme A to FPP.

KRX *E. coli* cells (Promega) were co-transformed with the plasmid pACYC-29258-4506 and the plasmid pJ401-

TABLE 1

Composition of the product mixture obtained in-vitro with the recombinant VzTps1718 sesquiterpene synthase.

| | Relative composition in product mixture | Ret Time [min] | Measured Linear retention Index (LRI) | Reference LRI |
| --- | --- | --- | --- | --- |
| sesquiterpene hydrocarbon | 1.27% | 8.91 | 1435 | |
| sesquiterpene hydrocarbon | 4.11% | 9.24 | 1462 | |
| sesquiterpene hydrocarbon | 1.62% | 9.60 | 1492 | |
| valencene | 3.65% | 9.67 | 1497 | 1494 |
| spirovetiva-1(10),7(11)-diene | 15.60% | 9.95 | 1521 | 1523 |
| isovalencene | 41.63% | 10.02 | 1527 | 1527 |
| sesquiterpene hydrocarbon | 4.01% | 10.14 | 1538 | |
| sesquiterpene hydrocarbon | 13.31% | 10.44 | 1563 | |
| oxygenated sesquiterpene | 13.40% | 11.05 | 1616 | |
| oxygenated sesquiterpene | 1.42% | 11.86 | 1689 | |

Sequiterpene synthases producing this mixture of products or synthases producing compound 1 or compound 2 were not known before. Oxygenated derivatives of the product of VzTps1718, especially alcohol, ketones, aldehydes and carboxylic acids are known constituents of vetiver oil and some of these derivatives contribute to the typical complex vetiver odour.

Example 5

In Vivo Production of Sesquiterpenes Using VzTps1718

For in-vivo production of the VzTps1718 sesquiterpene products, *E. coli* cells were transformed with the pJ401-VzTps1718 expression plasmid and the production of sesquiterpenes from the endogenous FPP pool was evaluated. To increase the productivity of the cells, a heterologous FPP synthase and the enzymes from a complete heterologous VzTps1718. Transformed cells were selected on kanamycin (50 μg/ml) and chloramphenicol (34 μg/ml) LB-agarose plates. Single colonies were used to inoculate 5 mL liquid LB medium supplemented with the same antibiotics. The culture was incubated overnight at 37° C. The next day 2 mL of TB medium supplemented with the same antibiotics were inoculated with 0.2 mL of the overnight culture. After 6 hours incubation at 37° C., the culture was cooled down to 20° C. and 0.1 mM IPTG and 0.02% rhamnose were added to each tube. The cultures were incubated for 48 hours at 20° C. The cultures were then extracted twice with 2 volumes of MTBE, the organic phase were concentrated to 500 μL and analysed by GC-MS as described above in Example 4.

In these in-vivo conditions, the VzTps1817 recombinant enzyme produced a mixture of sesquiterpenes with a very similar composition as in the in-vitro assay (FIG. 3—table 2). The relative abundance of spirovetiva-1(10),7(11)-diene, isovalencene and valencene in the product mixture were 14.7%, 39.0% and 5.1%, respectively.

TABLE 2

Composition of the product mixture obtained in-vivo with
the recombinant VzTps1718 sesquiterpene synthase.

| | Relative composition in product mixture | Ret Time [min] | Measured Linear retention Index (LRI) | Reference LRI |
|---|---|---|---|---|
| sesquiterpene hydrocarbon | 1.0% | 8.43 | 1392 | |
| sesquiterpene hydrocarbon | 0.9% | 8.92 | 1432 | |
| sesquiterpene hydrocarbon | 1.4% | 9.06 | 1444 | |
| sesquiterpene hydrocarbon | 4.5% | 9.25 | 1460 | |
| sesquiterpene hydrocarbon | 2.0% | 9.62 | 1490 | |
| valencene | 5.1% | 9.68 | 1495 | 1494 |
| spirovetiva-1(10),7(11)-diene | 14.7% | 9.97 | 1519 | 1523 |
| isovalencene | 39.0% | 10.03 | 1524 | 1527 |
| sesquiterpene hydrocarbon | 3.5% | 10.15 | 1535 | |
| sesquiterpene hydrocarbon | 1.4% | 10.20 | 1545 | |
| sesquiterpene hydrocarbon | 1.5% | 10.26 | 1565 | |
| sesquiterpene hydrocarbon | 12.7% | 10.452 | 1561 | |
| oxygenated sesquiterpene | 0.9% | 11.023 | 1610 | |
| oxygenated sesquiterpene | 9.3% | 11.06 | 1614 | |
| oxygenated sesquiterpene | 2.0% | 11.86 | 1686 | |

Example 6

Enzymatic Oxidation of the Sesquiterpenes Produced by VzTps1718 Using Vetiver Cytochrome P450 Enzymes The different sesquiterpene hydrocarbons used as substrates in the bioconversion assays were prepared using the *E. coli* cells described in Example 5 and expressing a heterologous MVA pathway and VzTP1718. A flash chromatography on a silica column was used to purify the sesquiterpene hydrocarbons from the extract of 1 L of culture. The resulting mixture of sesquiterpene hydrocarbons, containing spirovetiva-1(10),7(11)-diene, isovalencene and valencene, was used for the experiments of biochemical oxidation.

The vetiver roots transcriptome data were searched for cytochrome P450 encoding sequences using the tBlastn algorithm (Altschul et al, J. Mol. Biol. 215, 403-410, 1990) and using as query the amino acid sequences of known cytochrome P450s with terpene hydroxylase activity such as the SEQ ID NO:1 and 2 of WO2013064411. Several cytochrome P450-encoding transcripts were isolated. The transcript VzTrspt-9_Locus 8201-12 (SEQ ID NO: 5) encoded for a 506 amino acid protein, VzCP8201-12 (SEQ ID NO: 7), and showed homology with cytochrome P450 amino acid sequences. The closest publicly available sequences are putative cytochrome P450 proteins from *Sorghum bicolor* or *Zea mays* (such as the sequence with the NCBI accession number XP_002466860.1 or DAA50205.1) with less than 84% sequence identity compared to VzCP8201-12.

A cDNA (SEQ ID NO: 8) sequence encoding for the full-length VzCP8201-12 (SEQ ID NO: 7) protein was designed with a codon usage for optimal expression in bacteria. A second cDNA (SEQ ID NO: 9) encoding for an N-terminal modified variant of VzCP8201-12 (SEQ ID NO: 10) was also designed, this modification include deletion of the 20 first amino acids and replacement by the MALL-LAVFLGLSCLLLLSLW peptide (SEQ ID NO: 17). The two cDNAs were synthesized and sub-cloned in the pCWori expression plasmid (Barnes, H. J. Method Enzymol. 272, 3-14; (1996)) providing the pCWori-VzCP8201-12 and pCWori-VzCP8201Bov plasmids, respectively.

For functional characterization of the VzCP8201-12 enzyme (SEQ ID NO: 7), the protein was heterologously expressed in *E. coli* cells. To reconstitute the activity of plant P450s, the presence of a second membrane protein is helpful. This protein, the P450-reductase (CPR), is involved in the transfer of electrons from the cofactor NADPH (reduced Nicotinamide adenine dinucleotide phosphate) to the P450 active site. It has been shown that a CPR from one plant can complement the activity of P450 enzyme from another plant (Jensen and Moller (2010) *Phytochemsitry* 71, 132-141). Several CPR-encoding DNA sequences have been reported from different plant sources. We selected a CPR previously isolated from *Mentha piperita* (CPRm, unpublished data, SEQ ID NO: 15) optimized the codon usage of the full-length cDNA (SEQ ID NO: 6) and cloned it into the NcoI and HindIII restriction sites of the pACYCDuet-1 expression plasmid (Novagen) providing the plasmid pACYC-CPRm.

*E. coli* cells (BL21 Star™(DE3), Invitrogen) were co-transformed with the plasmids pCWori-VzCP8201-12 or pCWori-VzCP8201Bov and with the pACYC-CPRm plasmid. The transformed cells were selected on carbenicillin (50 µg/ml) and chloramphenicol (34 µg/ml) LB-agarose plates. Single colonies were used to inoculate 5 mL liquid LB medium supplemented with the same antibiotics. The culture was incubated overnight at 37° C. The next day, 20 mL of TB medium supplemented with the same antibiotics were inoculated with the overnight culture and starting with a OD of 0.15. After 2 hours incubation at 37° C., the culture was cooled down to 25° C. and 1 mM IPTG and 75 mg/L δ-aminolevulinic acid were added. After 24 hours, the cells were harvested, centrifuged and resuspended in 4 ml of potassium phosphate buffer 50 mM pH 7.0 supplemented with 5% glycerol. The mixture of sesquiterpene prepared as described above was diluted in ethanol at 10 mg/ml and added to the cell suspension to a final concentration of 0.1 mg/ml. The conversion was allowed to proceed for 24 hours at 25° C. with moderate shaking. The media were extracted with 2 volumes of MTBE (Methyl tert-buthyl ether, Sigma) and the extracts were analysed by GCMS as described in Example 4.

Several oxygenated sesquiterpene compounds were formed during this bioconversion (FIGS. 7 and 8). The major product was isovalencenyl acetate (FIG. 1) which is formed by oxidation of isovalencene by VzCP8201 producing isovalencenol (FIG. 1), followed by acetylation of isovalencenol by background *E. coli* enzymatic activity.

Example 7

Enzymatic Oxidation of the Sesquiterpenes Produced by VzTps1718 Using CYP71D4

CYP71D4 (SEQ ID NO: 12) from *Solanum tuberosum* (NCBI accession No CAC24711.1) was also evaluated for the oxidation of the sesquiterpene hydrocarbons produced by VzTps1718. A codon optimized cDNA (SEQ ID NO: 13) encoding for an N-terminal variant of CYP71D4 was designed and synthesized (DNA2.0). In this N-terminal variant, CYP71D4opt (SEQ ID NO: 14), the 19 first amino acids are replaced by the MALLLAVFWSALIILVLS peptide (SEQ ID NO: 18). The optimized cDNA (SEQ ID NO: 13) was ligated into the NdeI and HindIII restriction sites of the pCWori expression plasmid (Barnes, H. J. Method Enzymol. 272, 3-14; (1996)) providing the pCWori-CYP71D4opt plasmid. Bioconversions were performed as described in Example 6 using BL21Star™(DE3) *E. coli* cells and co-expressing the CYP71D4opt with the CPRm.

Thus with CYP71D4, several of the sesquiterpene hydrocarbon produced by VzTps1718 could be converted to a sesquiterpene alcohol. Three products were identified: nootkatol, β-vetivol and isonootkatol (FIGS. 9 and 1). These oxygenated sesquiterpenes can be easily oxidized to the corresponding ketones, for example biochemically or chemically (Oxidation of Alcohols to Aldehydes and Ketones, G. Tojo and M. Fernadez, in Basic Reactions in Organic Synthesis (2007)) to produce the major vetiver oil constituents nootkatone, α-vetivone and β-vetivone.

Example 8

In Vivo Production of Oxygenated Sesquiterpene Compounds Using VzTps1718 and Cytochrome P450 Enzymes The oxygenated sesquiterpene compounds produced using the method described in Examples 6 and 7 can also be obtained in vivo in bacteria cells engineered to co-express a sesquiterpene synthase (VzTps1718) and a cytochrome P450 VzCP8201.

A new plasmid was constructed comprising the pCWori+ plasmid (Barnes H. J (1996) Method Enzymol. 272, 3-14) containing a synthetic operon composed of a P450, a CPR and the terpene synthase encoding cDNA. The constructs were designed to insert upstream of each cDNA a ribosome binding site (RBS). The pCWori-VzCP8201Bov plasmid described in Example 6 contains the VzCP8201Bov-encoding cDNA (SEQ ID NO: 9) that was designed to include the NdeI recognition sequence upstream of the VzCP8201Bov-encoding cDNA and a polylinker DNA sequence (GTCGACAATTAACCATGGTTAATTAAGCT-TATATATG GTACCATATATGAATTCATTAATCTCGAG (SEQ ID NO: 19)) downstream of the VzCP8201Bov-encoding cDNA and containing the SalI, NcoI, HindIII, KpnI, EcoRI and XhoI recognition sequences. The optimized CPRm cDNA was modified to add at the 5'-end, before the start codon, a 26 bp extension containing a spacer sequence, the SalI recognition sequence and the RBS sequence (GTCGACAATTAGGTAAAAAATAAACC (SEQ ID NO: 20)) and to add a HindIII recognition sequence at the 3'-end. The optimized CPRm cDNA was sub-cloned between the SalI and HindIII sites of the pCWori-VzCP8201Bov plasmid providing the pCWori-VzCP8201Bov-CPRm plasmid. The optimized cDNA sequence of VzTps1718 cloned in the pJ401 plasmid (DNA2.0, Menlo Park, Calif., USA) contains a 5' non coding sequence composed of a HindIII recognition sequence and a RBS sequence (AAGCT-TAAGGAGGTAAAAA SEQ ID NO: 21)) and a 3' non coding sequence composed of the KpnI, EcoRI and XhoI recognition sites (GGTAC-CATATATGAATTCATTAATCTCGAG (SEQ ID NO: 22)). The insert form the VzTps1718-pJ401 plasmid was digested using the HindIII and XhoI restriction enzymes and sub-cloned between the same restriction enzyme recognition sites of the pCWori-VzCP8201Bov-CRPm plasmid. The resulting plasmid pCWori:VzCP8201Bov:CPRm: VzTps1718 contained thus an operon including the VzCP8201Bov-encoding cDNA, the CPRm-encoding cDNA and the VzTps1718-encoding cDNA.

The optimized cDNA (SEQ ID NO: 13) encoding for the N-terminal modified CYP71D4 protein (SEQ ID NO: 14) was transferred from the pCWori-CYP71D4opt plasmid (Example 7) into the pCWori:VzCP8201Bov:CPRm: VzTps1718 by digestion/ligation using the NdeI and HindIII restriction enzymes. The new plasmid, pCWori: CYP71D4opt:CPRm:VzTps1718, thus contained an operon including the CYP71D4opt-encoding cDNA, the CPRm-encoding cDNA and the VzTps1718-encoding cDNA.

The KRX *E. coli* cells (Promega) were co-transformed with one of the two pCWori plasmids described above and with plasmid pACYC-29258-4506 carrying a complete mevalonate pathway (Example 5). Transformed cells were selected on carbenicillin (50 µg/ml) and chloramphenicol (34 µg/ml) LB-agarose plates. Single colonies were used to inoculate 5 mL of LB medium supplemented with appropriate antibiotics. Cultures were incubated overnight at 37° C. and 250 rpm. The next day 2 mL of TB medium in glass culture tubes containing 100 µg/L carbenicilin and 17 µg/L chloramphenicol, were inoculated with 200 µl of the LB pre-culture and incubated at 37° C. and 250 rpm. After 6 hours of cultivation (or when the optical density at 600 nm of the culture reach a value of 3), the cultures were cooled down to 20° C. and the expression of the proteins was induced with 0.1 mM IPTG (Isopropylβ-D-1-thiogalactopyranoside) and 0.02% rhamnose, and 75 µg/L δ-aminolevulinic acid (Sigma) and 2% (v/v) of decane were added. After 48 h incubation with 250 rpm shaking, the whole culture broth was extracted with 1 volume of MTBE and analyzed by GCMS as described in Example 4.

FIG. 10 shows the GCMS of the products formed using *E. coli* cells engineered to produce the recombinant VzTps1718 sesquiterpene synthase either alone or together with the VzCP8201 or the CYP71D4 cytochrome P450 enzymes. These data show that using this approach the oxygenated sesquiterpene compounds described in Examples 6 and 7 can be produced in-vivo in engineered cells.

Sequence listing:

SEQ ID NO: 1
Full length amino acid sequence of VzTps1718:
MAASITVAAAHGPPAAIPETKRSTVDDVPFQSSVWGDYFVNYTPPASQRSEEWMRERVDELRGE

VRRKFKTTMSMAETMVLVDTLERLAIDGHFRKDIDLALSQIHMEGKPAGISSSNKLYIVALGFRL

LRQHGFWVSADVFDKFRDSTGKLSKGLSGDVKGLLSLYNAAHMAVPGEKSLDEAIDFTRRCLES

AKDRLVAPMSVQVSRALSIPLPRYLPRLEAMHYISEYGQEEDHDAKILELARLDYALVQSLYLKE

LRELTLWWKELYHSVNLPNTRDRIVEMYFFAFGMLQTEEYSRARLIDSKIIALVSLMDDIYDEHA

SFEEAQKFNEAIQRWNESAVSDLPEYMRMLYTQILSTFAKFEEVLGPNEKYRVSYAKEAYKLQS

MYYFLENKWCHENHMPSFGEHIHLSSMSAGLQVLIVGAWIGAHHAIAKESLEWAITYPEVFRAA

GDVGRLLNDIASFKKRKNSKDAPNALECYVREHGVTGEEAAAACAAIVELGWRKINRARMEIH

PMLVPAAQMDAKINLTRVCEILYYRGMDGYTFGSDLRDVITSLFIKPAAGGPA

VzTps1718 wild type cDNA sequence including 3' and 5' non coding
regions:

SEQ ID NO: 2
ACTGGAGTTCAGACGTGTGCTCTTCCGATCTATCGGAGTGAAGTTGAGCAGCTAACTTCACG

ACTCGTTTGCAGGCTAGCTCGCAACAGAATAGAGAGTGTTACTGCTGGTATATATATATATA

TATATATGGCTGCGAGCATTACTGTCGCCGCCGCACATGGGCCTCCTGCTGCAATCCCAGAG

ACCAAACGCAGCACTGTAGACGACGTTCCTTTCCAATCCTCTGTGTGGGCGACTACTTTGT

AAACTACACACCTCCTGCATCACAGAGGTCGGAGGAATGGATGAGGGAGAGGGTTGATGAA

CTCAGGGGTGAAGTGCGCCGGAAGTTCAAAACGACGATGAGCATGGCCGAGACGATGGTGC

TGGTGGACACACTGGAGCGCCTCGCCATCGACGGCCATTTCCGCAAGGATATTGACTTGGCG

TTGAGCCAAATCCACATGGAGGGGAAGCCGGCCGGTATTAGCAGCTCCAACAAGCTTTACA

TCGTCGCCCTGGGATTCCGCTTGCTTAGGCAACATGGCTTCTGGGTATCCGCAGACGTGTTTG

ACAAGTTTAGGGATAGCACGGGCAAGCTTAGCAAGGGTCTGAGCGGCGACGTGAAGGGTCT

GCTGAGCCTATACAACGCGGCTCACATGGCGGTTCCCGGCGAGAAAAGCCTGGACGAAGCC

ATCGACTTCACAAGGCGCTGCCTCGAGTCTGCCAAGGACAGGCTCGTGGCGCCGATGTCGGT

GCAGGTGTCGCGCGCCCTCAGCATTCCTCTCCCCCGCTACCTGCCGCGGCTAGAGGCCATGC

ACTACATCTCAGAGTATGGGCAGGAGGAGGACCATGACGCCAAGATCCTGGAGCTTGCGAG

GCTGGACTATGCCCTTGTCCAGTCTCTCTATCTCAAGGAGCTCAGGGAGCTCACCTTGTGGTG

GAAGGAGCTGTATCACAGCGTGAATCTGCCCAACACACGGGACCGCATCGTGGAGATGTAC

TTCTTTGCATTTGGTATGCTGCAGACGGAGGAGTACTCTCGGGCGCGCCTGATTGATAGCAA

GATAATTGCACTGGTCAGCCTGATGGATGACATTTACGACGAACACGCTAGCTTTGAGGAAG

CCCAAAAATTCAATGAAGCCATACAGAGATGGAATGAAAGTGCGGTCTCAGACCTACCAGA

ATACATGCGCATGCTATACACCCAAATACTAAGCACCTTCGCCAAATTTGAGGAAGTTTTGG

GGCCCAACGAAAAGTACCGCGTGTCTTACGCCAAAGAGGCGTACAAATTGCAGTCGATGTA

TTACTTTCTGGAGAACAAATGGTGTCACGAGAACCACATGCCAAGCTTCGGAGAGCACATAC

ATCTTTCTTCCATGTCGGCAGGCTTGCAGGTGTTGATCGTTGGGGCATGGATAGGCGCCCAC

CACGCCATTGCCAAGGAGTCACTAGAGTGGGCAATCACCTACCCTGAAGTCTTCCGGGCAGC

AGGAGATGTTGGCCGTCTCCTCAACGATATCGCTTCATTTAAGAAGAGGAAAAACAGCAAG

GACGCGCCCAACGCGCTGGAGTGCTACGTCAGAGAACATGGCGTCACGGGGGAGGAAGCTG

CGGCCGCGTGTGCAGCCATTGTAGAGCTCGGGTGGAGGAAGATCAACAGGGCCCGTATGGA

GATACATCCTATGCTGGTACCCGCGGCACAAATGGATGCGAAAATCAACCTGACCAGGGTG

TGCGAGATTTTATACTACCGTGGTATGGATGGCTACACCTTTGGAAGCGACCTCCGGGATGT

CATCACTTCTCTCTTCATCAAGCCGGCGGCCGGGGGCCCTGCATAATT

VzTps1718 wild type cDNA open reading frame sequence:

SEQ ID NO: 3

ATGGCTGCGAGCATTACTGTCGCCGCCGCACATGGGCCTCCTGCTGCAATCCCAGAGACCAA

ACGCAGCACTGTAGACGACGTTCCTTTCCAATCCTCTGTGTGGGGCGACTACTTTGTAAACT

ACACACCTCCTGCATCACAGAGGTCGGAGGAATGGATGAGGGAGAGGGTTGATGAACTCAG

GGGTGAAGTGCGCCGGAAGTTCAAAACGACGATGAGCATGGCCGAGACGATGGTGCTGGTG

GACACACTGGAGCGCCTCGCCATCGACGGCATTTCCGCAAGGATATTGACTTGGCGTTGAG

CCAAATCCACATGGAGGGGAAGCCGGCCGGTATTAGCAGCTCCAACAAGCTTTACATCGTC

GCCCTGGGATTCCGCTTGCTTAGGCAACATGGCTTCTGGGTATCCGCAGACGTGTTTGACAA

GTTTAGGGATAGCACGGGCAAGCTTAGCAAGGGTCTGAGCGGCGACGTGAAGGGTCTGCTG

AGCCTATACAACGCGGCTCACATGGCGGTTCCCGGCGAGAAAAGCCTGGACGAAGCCATCG

ACTTCACAAGGCGCTGCCTCGAGTCTGCCAAGGACAGGTCGTGGCGCCGATGTCGGTGCAG

GTGTCGCGCGCCCTCAGCATTCCTCTCCCCGCTACCTGCCGCGGCTAGAGGCCATGCACTA

CATCTCAGAGTATGGGCAGGAGGAGGACCATGACGCCAAGATCCTGGAGCTTGCGAGGCTG

GACTATGCCCTTGTCCAGTCTCTCTATCTCAAGGAGCTCAGGGAGCTCACCTTGTGGTGGAA

GGAGCTGTATCACAGCGTGAATCTGCCCAACACACGGGACCGCATCGTGGAGATGTACTTCT

TTGCATTTGGTATGCTGCAGACGGAGGAGTACTCTCGGGCGCGCCTGATTGATAGCAAGATA

ATTGCACTGGTCAGCCTGATGGATGACATTTACGACGAACACGCTAGCTTTGAGGAAGCCCA

AAAAATTCAATGAAGCCATACAGAGATGGAATGAAAGTGCGGTCTCAGACCTACCAGAATAC

ATGCGCATGCTATACACCCAAATACTAAGCACCTTCGCCAAATTTGAGGAAGTTTTGGGGCC

CAACGAAAAGTACCGCGTGTCTTACGCCAAAGAGGCGTACAAATTGCAGTCGATGTATTACT

TTCTGGAGAACAAATGGTGTCACGAGAACCACATGCCAAGCTTCGGAGAGCACATACATCTT

TCTTCCATGTCGGCAGGCTTGCAGGTGTTGATCGTTGGGGCATGGATAGGCGCCCACCACGC

CATTGCCAAGGAGTCACTAGAGTGGGCAATCACCTACCCTGAAGTCTTCCGGGCAGCAGGA

GATGTTGGCCGTCTCCTCAACGATATCGCTTCATTTAAGAAGAGGAAAAACAGCAAGGACG

CGCCCAACGCGCTGGAGTGCTACGTCAGAGAACATGGCGTCACGGGGGAGGAAGCTGCGGC

CGCGTGTGCAGCCATTGTAGAGCTCGGGTGGAGGAAGATCAACAGGGCCCGTATGGAGATA

CATCCTATGCTGGTACCCGCGGCACAAATGGATGCGAAAATCAACCTGACCAGGGTGTGCG

AGATTTTATACTACCGTGGTATGGATGGCTACACCTTTGGAAGCGACCTCCGGGATGTCATC

ACTTCTCTCTTCATCAAGCCGGCGGCCGGGGGCCCTGCATAA

VzTps1718 codon optimized cDNA sequence

SEQ ID NO: 4

ATGGCAGCAAGCATCACGGTCGCCGCAGCACACGGTCCGCCAGCAGCAATCCCGGAAACCA

AACGCAGCACCGTGGATGACGTTCCATTTCAATCCTCGGTGTGGGGCGACTACTTCGTCAAC

TATACGCCGCCGGCGAGCCAGCGTTCCGAAGAGTGGATGCGTGAACGCGTTGACGAACTGC

GTGGCGAAGTGCGTCGTAAGTTCAAGACTACCATGAGCATGGCTGAAACCATGGTTCTGGTT

GATACCCTGGAGCGCCTTGCAATCGATGGTCATTTTCGTAAAGATATTGACCTGGCACTGAG

CCAGATCCACATGGAGGGTAAACCGGCGGGTATTAGCTCGTCTAACAAGCTGTATATCGTTG

CGCTGGGCTTTCGTTTGTTGCGTCAGCACGGTTTCTGGGTGAGCGCCGATGTTTTCGATAAAT

TTCGTGATAGCACGGGCAAACTGTCCAAGGGCCTGAGCGGCGACGTCAAGGGCCTGCTGTC

ACTGTATAATGCCGCACACATGGCTGTCCCGGGTGAGAAATCTCTGGATGAAGCGATTGACT

-continued

```
TTACGCGTCGCTGCCTGGAAAGCGCCAAAGATCGTTTGGTGGCCCCGATGAGCGTCCAGGTT

AGCCGCGCCCTGAGCATCCCGCTGCCGCGTTATCTGCCGCGCCTGGAAGCGATGCATTACAT

CAGCGAGTATGGTCAAGAGGAAGATCACGACGCTAAGATCCTGGAATTGGCGCGCCTGGAC

TACGCGCTGGTCCAAAGCCTGTACCTGAAAGAACTGCGCGAGCTGACCCTGTGGTGGAAAG

AACTGTACCACTCCGTTAATCTGCCGAACACCCGTGACCGCATCGTCGAGATGTATTTCTTTG

CGTTTGGTATGTTGCAGACCGAAGAGTACTCTCGTGCTCGCCTGATCGATAGCAAGATTATC

GCCCTGGTGAGCCTGATGGATGACATTTATGATGAGCATGCCAGCTTCGAGGAAGCTCAAAA

GTTTAACGAAGCAATCCAACGTTGGAATGAAAGCGCGGTTAGCGACTTGCCGGAGTATATG

CGCATGCTGTACACCCAAATCCTGAGCACCTTCGCGAAGTTTGAAGAGGTTCTGGGTCCGAA

CGAAAAATATCGCGTGAGCTATGCGAAAGAGGCGTACAAGCTGCAATCCATGTACTATTTCC

TGGAGAACAAATGGTGTCATGAGAATCACATGCCGAGCTTCGGTGAGCACATTCACCTGAG

CTCCATGTCCGCGGGTTTGCAAGTGTTGATTGTGGGTGCTTGGATCGGCGCACATCATGCCA

TTGCAAAAGAGAGCCTGGAGTGGGCGATTACCTACCCTGAAGTTTTTCGTGCCGCGGGCGAT

GTGGGTCGTCTGTTGAATGACATTGCAAGCTTCAAAAAGCGTAAGAACTCTAAAGACGCCCC

GAACGCGCTGGAGTGTTATGTCCGTGAACACGGCGTGACTGGCGAAGAAGCGGCAGCTGCC

TGCGCAGCTATTGTTGAGCTGGGTTGGCGTAAGATCAACCGTGCGCGCATGGAAATCCATCC

GATGCTGGTCCCGGCGGCGCAGATGGACGCGAAAATCAATTTGACCCGTGTGTGCGAGATC

CTGTACTACCGTGGCATGGATGGTTACACCTTCGGTAGCGATTTACGCGATGTGATTACGAG

CCTCTTCATTAAGCCTGCGGCTGGCGGCCCGGCGTAA
```

VzTrspt-9_Locus_8201-12, full length transcript containing 5' and 3 non-translated sequences

SEQ ID NO: 5

```
GATCGTTTCACGTGACTGGAGTTCAGACGTGTGCTCTTCCGATCTCAAAAAATGGACTTTCTC

AGAATCCCGTTTCTTGTAGCCTTCGTCTTCCTCGCCGTCCTTCTCAGGCTCATCCGGAGCTAC

ATCACATCCTCAGCTCTTCGCCTGCCACCGGGGCCATGGCAGCTGCCGCTCATCGGCAGCCT

GCACCACCTCCTGCTGTCGCGCTTCAGCGACCTCCCTCACCGGGCTTTGCGCGAGATGTCCG

GCACCTACGGGCCCCTCATGCTGCTCCGCTTCGGCTCCGTGCCCACGCTGGTGGTCTCCTCCG

CCGAGGCTGCCCGGGAGGTGATGAGGACCCACGACCTCGCCTTCTGCGACCGCCACCTCGGC

GTCACTCTCGACATCGTCACCTGCGGCGGCAAGGACATCATCTGCTCCCCCTACAACGCCCA

CTGGCGCGAGCTCCGTAAGCTGTGCATGGTCGAGATCTTGAGCCAGCGGCGCGTGCTCTCGT

TCCGGAGCATCCGGGAAGAGGAGGTGGCGAGCCTCGTCCGCTCCATCTCCGACGAGTGCGG

CGGTGGCCAGCAGCCCGTCAACCTCACTGAAGGGATAAGCCGCATGATAAACGACGTCGCC

GCGCGCACGGTCGTCGGCGACCGGTGCAAGTACCAGGATGAATACATGCATGAGCTGGACG

AAGTGGTGCGGCTGGCCGGCGGGTTCAACCTGGCGGACCTGTACCCGTCCTCGCGGCTGGTA

CGGCGGTTCAGCGCCGCCGCGAGGGACGCGAGGAGGTGCCAGAGGAACATGTACCGTATCA

TCCAGAGCATCATCCAGGAGCGTGAAGCCATGCCGACGCCAGAGCGAGACGAGGAGGACCT

CCTCGGCGTCCTCCTCAGGCTGCAGAGAGAAGGTGGCCTGCAGTTTGCTCTCACCAATGAGA

TAGTCAGCACCGTCATTTACGATATTTTTTCTGCTGGTAGTGAAACATCATCAACTGTTCTAG

TATGGGCAATGTCGGAGCTTGTTAAGAATCCACAAGTCATGCGTAAGGCCCAGTCAGAGGT

GAGGGATACCTTCAAAGGAAACAACAAGATAACTGAAAGTGATTTGATCAAGTTAAGATAT

CTACAACTGGTGATCAAGGAGACTTTACGGTTGCATGCTCCGGTACCACTCTTGCTCCCTCG

AGAATGCCGTGAGTCATGTCAGATTATGGGTTACGATGTGCTAAAGGGAACCAAGGTATTTG
```

-continued

TGAATGCTTGGGCAATAGCAAGGGACACGGGATTATGGTGTGATGGAGAGGAATTTAGGCC

AGAAAGGTTTGAAAGTAGCAATATTGATTTCAGGGGTAATGACTTTGAGTTCACACCGTTTG

GGGCAGGCAGGAGAGTATGCCCTGGCATCACACTTGGACTGGCCAACCTAGAACTAGCGCT

TGCTAGCCTTCTTTATCATTTTGATTGGGATCTGCCCAATGGTGCCAGGTTGGAAGATCTTGA

TATGGCAGAGGCCTTTGGTATAACGTTAAAAAGGAAGTCCATGCTCTGGCTCAAGGCCAAAC

CTTACAATAATTTTATACCAAATTAATCAGGTGATTTGTGATGTGAACTATCCCGGTTGCTAC

TTAGTTTATTATACCCAGAAAGAGTGTGATGGTAATTGTACTATCAATCTTTACTGCAGAAC

AGTAAATATATCCAGAGTTGGTTCTATGCTTCTGTTATAATGTTTCATCACTCTGTATTAAGT

GTGTAGTTATCTGTTTGTTTACTTTTTTTGTAATGATTAAACGATTATCTAATGAGAGTACAA

GAATCAAATGAGACTGGTCTAAAAAAAA

VzCp8201-12 wild type cDNA sequence, open read frame only.
SEQ ID NO: 6

ATGGACTTTCTCAGAATCCCGTTTCTTGTAGCCTTCGTCTTCCTCGCCGTCCTTCTCAGGCTCA

TCCGGAGCTACATCACATCCTCAGCTCTTCGCCTGCCACCGGGGCCATGGCAGCTGCCGCTC

ATCGGCAGCCTGCACCACCTCCTGCTGTCGCGCTTCAGCGACCTCCCTCACCGGGCTTTGCGC

GAGATGTCCGGCACCTACGGGCCCCTCATGCTGCTCCGCTTCGGCTCCGTGCCCACGCTGGT

GGTCTCCTCCGCCGAGGCTGCCCGGGAGGTGATGAGGACCCACGACCTCGCCTTCTGCGACC

GCCACCTCGGCGTCACTCTCGACATCGTCACCTGCGGCGGCAAGGACATCATCTGCTCCCCC

TACAACGCCCACTGGCGCGAGCTCCGTAAGCTGTGCATGGTCGAGATCTTGAGCCAGCGGCG

CGTGCTCTCGTTCCGGAGCATCCGGGAAGAGGAGGTGGCGAGCCTCGTCCGCTCCATCTCCG

ACGAGTGCGGCGGTGGCCAGCAGCCCGTCAACCTCACTGAAGGGATAAGCCGCATGATAAA

CGACGTCGCCGCGCGCACGGTCGTCGGCGACCGGTGCAAGTACCAGGATGAATACATGCAT

GAGCTGGACGAAGTGGTGCGGCTGGCCGGCGGGTTCAACCTGGCGGACCTGTACCCGTCCTC

GCGGCTGGTACGGCGGTTCAGCGCCGCCGCGAGGGACGCGAGGAGGTGCCAGAGGAACATG

TACCGTATCATCCAGAGCATCATCCAGGAGCGTGAAGCCATGCCGACGCCAGAGCGAGACG

AGGAGGACCTCCTCGGCGTCCTCCTCAGGCTGCAGAGAGAAGGTGGCCTGCAGTTTGCTCTC

ACCAATGAGATAGTCAGCACCGTCATTTACGATATTTTTTCTGCTGGTAGTGAAACATCATC

AACTGTTCTAGTATGGGCAATGTCGGAGCTTGTTAAGAATCCACAAGTCATGCGTAAGGCCC

AGTCAGAGGTGAGGGATACCTTCAAAGGAAACAACAAGATAACTGAAAGTGATTTGATCAA

GTTAAGATATCTACAACTGGTGATCAAGGAGACTTTACGGTTGCATGCTCCGGTACCACTCT

TGCTCCCTCGAGAATGCCGTGAGTCATGTCAGATTATGGGTTACGATGTGCTAAAGGGAACC

AAGGTATTTGTGAATGCTTGGGCAATAGCAAGGGACACGGGATTATGGTGTGATGGAGAGG

AATTTAGGCCAGAAAGGTTTGAAAGTAGCAATATTGATTTCAGGGGTAATGACTTTGAGTTC

ACACCGTTTGGGGCAGGCAGGAGAGTATGCCCTGGCATCACACTTGGACTGGCCAACCTAG

AACTAGCGCTTGCTAGCCTTCTTTATCATTTTGATTGGGATCTGCCCAATGGTGCCAGGTTGG

AAGATCTTGATATGGCAGAGGCCTTTGGTATAACGTTAAAAAGGAAGTCCATGCTCTGGCTC

AAGGCCAAACCTTACAATAATTTTATACCAAATTAA

VzCP8201-12, wild type amino acid sequence.

SEQ ID NO: 7

MDFLRIPFLVAFVFLAVLLRLIRSYITSSALRLPPGPWQLPLIGSLHHLLLSRFSDLPHRALREMSG

TYGPLMLLRFGSVPTLVVSSAEAAREVMRTHDLAFCDRHLGVTLDIVTCGGKDIICSPYNAHWR

ELRKLCMVEILSQRRVLSFRSIREEEVASLVRSISDECGGGQQPVNLTEGISRMINDVAARTVVGD

RCKYQDEYMHELDEVVRLAGGFNLADLYPSSRLVRRFSAAARDARRCQRNMYRIIQSIIQEREA

MPTPERDEEDLLGVLLRLQREGGLQFALTNEIVSTVIYDIFSAGSETSSTVLVWAMSELVKNPQV

MRKAQSEVRDTFKGNNKITESDLIKLRYLQLVIKETLRLHAPVPLLLPRECRESCQIMGYDVLKG

TKVFVNAWAIARDTGLWCDGEEFRPERFESSNIDFRGNDFEFTPFGAGRRVCPGITLGLANLELA

LASLLYHFDWDLPNGARLEDLDMAEAFGITLKRKSMLWLKAKPYNNFIPN

VzCP8201-228093, optimized DNA sequence encoding for VzCP8201-12,
including NdeI site at 5′end and polylinker at 3′end.

SEQ ID NO: 8

ATGGCACTGTTGTTGGCTGTTTTTTTGGGTTTGAGCTGTTTGTTGCTGTTGAGCTTGTGGCGTC

TGATCCGCAGCTACATTACTTCCAGCGCGCTGCGCCTGCCGCCGGGTCCGTGGCAGCTGCCT

CTGATTGGCAGCCTGCACCACTTGCTGCTGAGCCGCTTCAGCGACTTGCCGCATCGCGCGCT

GAGAGAGATGAGCGGCACCTACGGTCCGCTGATGCTGCTGCGTTTCGGTAGCGTCCCGACCC

TGGTTGTCTCTAGCGCGGAAGCGGCTCGTGAAGTCATGCGTACCCACGATCTGGCGTTTTGC

GATCGTCACCTGGGTGTGACGCTGGACATCGTAACCTGTGGTGGCAAAGACATCATCTGCAG

CCCATACAACGCTCATTGGCGTGAGCTGCGCAAGCTGTGCATGGTTGAAATCCTGAGCCAGC

GCCGTGTGCTGAGCTTCCGTTCGATTCGTGAAGAAGAGGTCGCGAGCCTGGTGCGTTCCATT

AGCGATGAGTGTGGTGGCGGCCAGCAACCAGTTAACCTGACCGAAGGCATCTCTCGCATGA

TTAATGACGTCGCCGCACGTACCGTGGTCGGTGACCGCTGCAAGTACCAAGACGAGTACATG

CATGAACTGGACGAAGTTGTTCGTCTGGCGGGTGGCTTCAACCTGGCCGATCTGTATCCGAG

CTCACGTCTGGTTCGTCGTTTTTCCGCAGCTGCGCGTGACGCGCGTCGCTGTCAGCGTAACAT

GTACCGCATTATTCAATCTATCATCCAAGAGCGTGAGGCAATGCCGACGCCTGAGCGCGACG

AAGAAGATCTTCTGGGTGTCCTGCTGCGTCTGCAGCGCGAGGGTGGTCTGCAGTTTGCGCTG

ACGAACGAAATTGTTTCGACCGTGATTTACGATATCTTCAGCGCCGGTAGCGAAACCTCCAG

CACGGTGTTGGTGTGGGCAATGTCTGAACTGGTCAAAAATCCGCAAGTGATGCGCAAAGCG

CAAAGCGAAGTTCGTGACACTTTCAAAGGTAACAATAAGATTACCGAGAGCGACCTGATTA

AGCTGCGCTATCTGCAACTGGTTATCAAAGAAACCCTGCGCCTGCACGCACCGGTGCCGCTG

CTGCTGCCGCGTGAGTGCCGTGAATCCTGTCAGATCATGGGCTATGACGTTCTGAAGGGTAC

GAAAGTGTTCGTTAATGCCTGGGCGATTGCACGTGATACGGGTCTGTGGTGCGACGGCGAAG

AGTTCCGTCCGGAGCGTTTCGAGTCCAGCAATATCGATTTTCGTGGTAATGATTTTGAGTTCA

CGCCGTTCGGTGCGGGCCGTCGTGTCTGCCCAGGCATCACCCTGGGCCTGGCCAACTTAGAA

CTGGCCCTCGCGAGCTTGTTATATCACTTTGACTGGGATCTGCCGAACGGCGCGCGCCTGGA

AGATCTGGACATGGCCGAGGCATTTGGTATCACGCTGAAGCGCAAGAGCATGCTGTGGCTG

AAAGCAAAACCGTACAATAATTTTATTCCGAACTAA

VzCP8201-228092, optimized DNA sequence encoding for VzCP8201-12-bov, including NdeI site at 5'end and polylinker at 3'end.

SEQ ID NO: 9

ATGGCACTGTTGTTGGCTGTTTTTTTGGGTTTGAGCTGTTTGTTGCTGTTGAGCTTGTGGCGTC

TGATCCGCAGCTACATTACTTCCAGCGCGCTGCGCCTGCCGCCGGGTCCGTGGCAGCTGCCT

CTGATTGGCAGCCTGCACCACTTGCTGCTGAGCCGCTTCAGCGACTTGCCGCATCGCGCGCT

GAGAGAGATGAGCGGCACCTACGGTCCGCTGATGCTGCTGCGTTTCGGTAGCGTCCCGACCC

TGGTTGTCTCTAGCGCGGAAGCGGCTCGTGAAGTCATGCGTACCCACGATCTGGCGTTTTGC

GATCGTCACCTGGGTGTGACGCTGGACATCGTAACCTGTGGTGGCAAAGACATCATCTGCAG

CCCATACAACGCTCATTGGCGTGAGCTGCGCAAGCTGTGCATGGTTGAAATCCTGAGCCAGC

GCCGTGTGCTGAGCTTCCGTTCGATTCGTGAAGAAGAGGTCGCGAGCCTGGTGCGTTCCATT

-continued

```
AGCGATGAGTGTGGTGGCGGCCAGCAACCAGTTAACCTGACCGAAGGCATCTCTCGCATGA

TTAATGACGTCGCCGCACGTACCGTGGTCGGTGACCGCTGCAAGTACCAAGACGAGTACATG

CATGAACTGGACGAAGTTGTTCGTCTGGCGGGTGGCTTCAACCTGGCCGATCTGTATCCGAG

CTCACGTCTGGTTCGTCGTTTTTCCGCAGCTGCGCGTGACGCGCGTCGCTGTCAGCGTAACAT

GTACCGCATTATTCAATCTATCATCCAAGAGCGTGAGGCAATGCCGACGCCTGAGCGCGACG

AAGAAGATCTTCTGGGTGTCCTGCTGCGTCTGCAGCGCGAGGGTGGTCTGCAGTTTGCGCTG

ACGAACGAAATTGTTTCGACCGTGATTTACGATATCTTCAGCGCCGGTAGCGAAACCTCCAG

CACGGTGTTGGTGTGGGCAATGTCTGAACTGGTCAAAAATCCGCAAGTGATGCGCAAAGCG

CAAAGCGAAGTTCGTGACACTTTCAAAGGTAACAATAAGATTACCGAGAGCGACCTGATTA

AGCTGCGCTATCTGCAACTGGTTATCAAAGAAACCCTGCGCCTGCACGCACCGGTGCCGCTG

CTGCTGCCGCGTGAGTGCCGTGAATCCTGTCAGATCATGGGCTATGACGTTCTGAAGGGTAC

GAAAGTGTTCGTTAATGCCTGGGCGATTGCACGTGATACGGGTCTGTGGTGCGACGGCGAAG

AGTTCCGTCCGGAGCGTTTCGAGTCCAGCAATATCGATTTTCGTGGTAATGATTTTGAGTTCA

CGCCGTTCGGTGCGGGCCGTCGTGTCTGCCCAGGCATCACCCTGGGCCTGGCCAACTTAGAA

CTGGCCCTCGCGAGCTTGTTATATCACTTTGACTGGGATCTGCCGAACGGCGCGCGCCTGGA

AGATCTGGACATGGCCGAGGCATTTGGTATCACGCTGAAGCGCAAGAGCATGCTGTGGCTG

AAAGCAAAACCGTACAA
```

VzCP8201-12-bov, amino acid sequence of N-terminal variant of VzCP8201-12.

SEQ ID NO: 10

```
MALLLAVFLGLSCLLLLSLWRLIRSYITSSALRLPPGPWQLPLIGSLHHLLLSRFSDLPHRALREMS

GTYGPLMLLRFGSVPTLVVSSAEAAREVMRTHDLAFCDRHLGVTLDIVTCGGKDIICSPYNAHW

RELRKLCMVEILSQRRVLSFRSIREEEVASLVRSISDECGGGQQPVNLTEGISRMINDVAARTVVG

DRCKYQDEYMHELDEVVRLAGGFNLADLYPSSRLVRRFSAAARDARRCQRNMYRIIQSIIQERE

AMPTPERDEEDLLGVLLRLQREGGLQFALTNEIVSTVIYDIFSAGSETSSTVLVWAMSELVKNPQ

VMRKAQSEVRDTFKGNNKITESDLIKLRYLQLVIKETLRLHAPVPLLLPRECRESCQIMGYDVLK

GTKVFVNAWAIARDTGLWCDGEEFRPERFESSNIDFRGNDFEFTPFGAGRRVCPGITLGLANLEL

ALASLLYHFDWDLPNGARLEDLDMAEAFGITLKRKSMLWLKAKPYNNFIPN
```

CYP71D4, wild type cDNA sequence, open read frame only.

SEQ ID NO: 11

```
ATGCAATTCTTGAGCTTGGCTTCCATCTTCCTTTTTCTATCTTTTCTGTTTTTGTTAAGGAAAT

GGAAAAACTCGAATAGCCAATCGAAAAAATTGCCTCCAGGTCCATGGAAACTTCCTTTACTA

GGAAGTATGCTTCATATGGCTGGTGGACTTCCACACCATGTCCTTAGAGATTTAGCCAAAAA

ATATGGACCACTTATGCATCTTCAACTTGGTGAAGTCTCTGCAGTTGTAGTAACTTCTCCTGA

TATGGCGAAAGAAGTACTAAAAACTCATGACATCGCTTTCGCCTCTAGGCCTAAACTTTTGG

CCCCGGAAATTGTTGTTACAACAGGTCTGACATTGCCTTTTGCCCCTACGGAGATTACTGGA

GACAAATGCGTAAAATTTGTGTCTTGGAATTGTTGAGTGCCAAGAATGTCCGGTCATATGGC

TCGATTAGGCGCGATGAAGTTGATCGCCTTGTTAATTTTATCCGGTCATCTTCGGGTGAGCCG

GTTAATTTTACTGAAAGGTTGTTTTGTTCACAAGTTCAATGACATGTAGATCAGCGTTCGGG

AAAGTGTTCAAAGAACAGGACAAATTTATACAACTAATCAAAGAAGTGATTGGGTTAGCAG

GAGGATTTGATGTGGCTGATATCTTCCCATCATTGAAGTTTCTCCATGTGCTTAGTGGAATGA

AAGGTAAAATTATGAACGCTCATCATAAGGTAGATGCAATTGTTGAAGATGTCATCAATGAG

CACAAGAAGAAATTTGCAATTGGGAAAACTAATGGTGCATTAGGTGGTGAAGATCTAATTG
```

-continued

ATGTCCTTATAAGACTTATGAATGATGGAGGCCTTCAATTTCCGATCACCAACGACAACATC

AAAGCTATTATTTTCGACATGTTTGCTGCAGGAACAGAGACTTCATCGTCAACACTTGTCTG

GGCAATGGTGCAAATGATGAAAAACCCAAGTGTAATCGCCAAAGCTCAAGCAGAAGTGCGA

GAAGCCTTTAAAGACAAAGAAACGTTCGATGAAAATGATGTAGAGGAGCTGAAATACTTAA

AGTTAGTCATTAAAGAAACTCTAAGACTCCATCCACCAGTTCCACTTTTGGTCCCAAGAGAA

TGTAGGGAAGAGACGGATATAAACGGCTACACTATTCCTGTGAAGACCAAAGTCATGGTTA

ATGTTTGGGCATTGGGAAGAGATCCGAAATATTGGGATGATGCAGAAAGTTTTAAGCCAGA

GAGATTTGAGCAGCGCTCTGTCGACTTTGTTGGTAACAATTTTGAGTATCTTCCCTTTGGCGG

TGGGAGAAGGATTTGTCCCGGGATATCATTTGGCTTAGCTAATGTTTATTTGCCGTTGGCTCA

TTTGTTATATCACTTCGACTGGAAACTCCCTATTGGAATGGAGCCAAAAGACTTGAACTTGA

CTGAATTGGTTGGAGTAACTGCTGCCAGAAAAGATGACCTTATTTTGGTTGCCACTCCTTATG

AACCACCTCGACAATGA

CYP71D4, wild type amino acid sequence.
SEQ ID NO: 12
MQFLSLASIFLFLSFLFLLRKWKNSNSQSKKLPPGPWKLPLLGSMLHMAGGLPHHVLRDLAKKY

GPLMHLQLGEVSAVVVTSPDMAKEVLKTHDIAFASRPKLLAPEIVCYNRSDIAFCPYGDYWRQM

RKICVLELLSAKNVRSYGSIRRDEVDRLVNFIRSSSGEPVNFTERLFLFTSSMTCRSAFGKVFKEQ

DKFIQLIKEVIGLAGGFDVADIFPSLKFLHVLSGMKGKIMNAHHKVDAIVEDVINEHKKKFAIGK

TNGALGGEDLIDVLIRLMNDGGLQFPITNDNIKAIIFDMFAAGTETSSSTLVWAMVQMMKNPSVI

AKAQAEVREAFKDKETFDENDVEELKYLKLVIKETLRLHPPVPLLVPRECREETDINGYTIPVKT

KVMVNVWALGRDPKYWDDAESFKPERFEQRSVDFVGNNFEYLPFGGGRRICPGISFGLANVYLP

LAHLLYHFDWKLPIGMEPKDLNLTELVGVTAARKDDLILVATPYEPPRQ

Codon optimized cDNA encoding for an N-terminal variant of CYP71D4,
including NdeI site at 5'end and SalI-HindIII sites at 3'end.
SEQ ID NO: 13
ATGGCTCTGTTGCTGGCAGTTTTCTGGTCCGCATTGATTATTTTGGTTCTGTCTCGCAAATGG

AAAAATAGCAACAGCCAGAGCAAAAAGCTGCCACCAGGCCCGTGGAAACTGCCGTTGCTGG

GTAGCATGCTGCACATGGCAGGCGGCCTGCCACACCATGTGCTGCGTGATCTGGCGAAGAA

ATACGGTCCGTTGATGCATCTGCAGCTGGGTGAAGTGAGCGCGGTCGTGGTGACGAGCCCG

GATATGGCGAAAGAAGTGCTGAAGACCCATGATATCGCATTCGCAAGCCGTCCAAAGCTGC

TGGCTCCGGAGATTGTCTGCTACAACCGTAGCGACATTGCGTTCTGTCCATACGGCGACTAC

TGGCGTCAAATGCGTAAGATTTGTGTGCTGGAACTGCTGAGCGCGAAAAATGTGCGCAGCTA

CGGCAGCATCCGTCGTGACGAGGTTGATCGTCTGGTGAATTTCATTCGTAGCAGCAGCGGCG

AGCCGGTTAACTTTACGGAGCGTCTGTTTCTGTTTACCTCCAGCATGACCTGCCGTTCCGCGT

TTGGCAAGGTGTTCAAGGAACAGGACAAGTTCATTCAACTGATTAAGGAAGTGATCGGCCT

GGCAGGCGGTTTCGATGTGGCCGACATCTTTCCGAGCCTGAAGTTTCTGCACGTGCTGTCTG

GTATGAAAGGCAAAATTATGAATGCACACCACAAGGTTGATGCGATCGTTGAAGATGTGAT

TAATGAACACAAGAAAAAGTTCGCGATTGGTAAGACGAACGGTGCGCTGGGTGGTGAGGAT

CTGATCGATGTTCTGATTCGCTTGATGAACGACGGTGGTCTGCAGTTTCCGATCACCAATGA

CAATATCAAAGCGATTATCTTCGACATGTTCGCCGCAGGCACGGAGACGTCTAGCAGCACCC

TGGTTTGGGCGATGGTTCAAATGATGAAGAATCCAAGCGTTATTGCAAAAGCCCAAGCGGA

AGTTCGTGAAGCGTTTAAAGATAAAGAGACTTTCGACGAAAACGATGTTGAGGAACTGAAG

TATCTGAAGCTGGTTATCAAGGAGACGCTGCGTCTGCACCCGCCGGTTCCGCTGCTGGTGCC

```
GCGTGAATGCCGTGAGGAGACGGATATTAATGGTTACACGATTCCGGTTAAAACCAAAGTC

ATGGTGAATGTGTGGGCGTTGGGCCGTGATCCGAAGTACTGGGACGATGCGGAGAGCTTTA

AACCGGAACGCTTCGAACAGCGTAGCGTGGATTTTGTTGGCAATAACTTTGAATATCTGCCA

TTCGGTGGTGGTCGCCGCATTTGCCCAGGCATTTCTTTCGGTCTGGCAAACGTTTATCTGCCG

CTGGCGCATTTGCTGTACCACTTCGACTGGAAATTGCCGATTGGCATGGAACCGAAAGACTT

GAACCTGACGGAACTGGTCGGCGTGACGGCGGCTCGTAAGGATGACCTGATTCTGGTCGCA

ACCCCATACGAACCGCCGCGTCAATAA
```

CYP71D4opt, amino acid sequence of an N-terminal variant of CYP7D
                                                    SEQ ID NO: 14
```
MALLLAVFWSALIILVLSRKWKNSNSQSKKLPPGPWKLPLLGSMLHMAGGLPHHVLRDLAKKY

GPLMHLQLGEVSAVVVTSPDMAKEVLKTHDIAFASRPKLLAPEIVCYNRSDIAFCPYGDYWRQM

RKICVLELLSAKNVRSYGSIRRDEVDRLVNFIRSSSGEPVNFTERLFLFTSSMTCRSAFGKVFKEQ

DKFIQLIKEVIGLAGGFDVADIFPSLKFLHVLSGMKGKIMNAHHKVDAIVEDVINEHKKKFAIGK

TNGALGGEDLIDVLIRLMNDGGLQFPITNDNIKAIIFDMFAAGTETSSSTLVWAMVQMMKNPSVI

AKAQAEVREAFKDKETFDENDVEELKYLKLVIKETLRLHPPVPLLVPRECREETDINGYTIPVKT

KVMVNVWALGRDPKYWDDAESFKPERFEQRSVDFVGNNFEYLPFGGGRRICPGISFGLANVYLP

LAHLLYHFDWKLPIGMEPKDLNLTELVGVTAARKDDLILVATPYEPPRQ
```

P450 reductase from *Mentha pperita* (CPRm) amino acid sequence
                                                    SEQ ID NO: 15
```
MEPSSQKLSPLEFVAAILKGDYSSGQVEGGPPPGLAAMLMENKDLVMVLTTSVAVLIGCVVVLA

WRRAAGSGKYKQPELPKLVVPKAAEPEEAEDDKTKISVFFGTQTGTAEGFAKAFVEEAKARYQ

QARFKVIDLDDYAADDDEYEEKLKKENLAFFFLASYGDGEPTDNAARFYKWFTEGKDRGEWLN

NLQYGVFGLGNRQYEHFNKIAIVVDDLIFEQGGKKLVPVGLGDDDQCIEDDFAAWRELVWPEL

DKLLRNEDDATVATPYSAAVLQYRVVFHDHIDGLISENGSPNGHANGNTVYDAQHPCRSNVAV

KKELHTPASDRSCTHLEFNISGTGLMYETGDHVGVYCENLLETVEEAEKLLNLSPQTYFSVHTDN

EDGTPLSGSSLPPPFPPCTLRTALTKYADLTSAPKKSVLVALAEYASDQGEADRLRFLASPSGKEE

YAQYILASQRTLLEVMAEFPSAKPPLGVFFAGVAPRLQPRFYSISSSPKIAPFRIHVTCALVYDKSI

TGRVHKGICSTWMKNAVPLEESNDCSWAPIFVRNSNFKLPTDPKVPIIMIGPGTGLAPFRGFLQEI

LALKESGAELGPAILFFGCRNRKMDFIYEDELNDFVKAGVVSELIVAFSREGPMKEYVQHKMSQ

RASDVWNIISDGGYVYVCGDAKGMARDVHRTLHTIAQEQGSMSSSEAEGMVKNLQTTGRYLR

DVW
```

SEQ ID NO: 16
P450 reductase from *Mentha pperita* (CPRm) DNA sequence
```
ATGGAACCTAGCTCTCAGAAACTGTCTCCGTTGGAATTTGTTGCTGCTATCCTGAAGGGCGA

CTACAGCAGCGGTCAGGTTGAAGGTGGTCCACCGCCAGGTCTGGCAGCTATGTTGATGGAA

AATAAGGATTTGGTGATGGTTCTGACGACGTCCTGGGCAGTCCTGATCGGCTGTGTCGTGGT

CCTGGCATGGCGTCGTGCGGCAGGTAGCGGTAAGTACAAGCAACCTGAACTGCCTAAACTG

GTGGTCCCGAAAGCAGCCGAACCGGAGGAGGCAGAGGATGATAAAACCAAGATCAGCGTG

TTTTTCGGCACCCAAACCGGTACGGCAGAAGGTTTCGCGAAGGCTTTTGTTGAAGAGGCCAA

GGCGCGTTATCAGCAGGCCCGTTTCAAAGTTATCGACCTGGACGACTATGCGGCAGACGATG

ACGAGTACGAAGAGAAACTGAAGAAGGAAAACTTGGCATTCTTCTTCTTGGCGTCCTACGGT

GACGGCGAGCCGACGGACAACGCGGCACGCTTTTACAAATGGTTTACGGAGGGTAAGGACC

GTGGTGAATGGCTGAACAATCTGCAGTACGGCGTTTTTGGTCTGGGTAACCGTCAATATGAG

CATTTCAATAAGATCGCCATTGTCGTCGATGATCTGATCTTCGAGCAAGGTGGCAAGAAGCT
```

```
GGTTCCGGTGGGTCTGGGTGACGATGACCAGTGCATTGAGGATGATTTTGCGGCGTGGCGTG

AACTGGTCTGGCCGGAACTGGATAAACTGCTGCGTAACGAAGACGACGCTACCGTGGCAAC

CCCGTACAGCGCCGCTGTGCTGCAATACCGCGTGGTTTTCCACGATCACATTGACGGCCTGA

TTAGCGAAAACGGTAGCCCGAACGGTCATGCTAATGGCAATACCGTGTACGATGCGCAACA

CCCGTGCCGTAGCAACGTCGCGGTCAAGAAGGAATTGCATACTCCGGCGAGCGATCGCAGC

TGCACCCACCTGGAATTTAACATTAGCGGTACCGGCCTGATGTACGAGACGGGTGACCACGT

CGGTGTGTATTGCGAGAACCTGTTGGAAACCGTGGAGGAGGCCGAGAAGTTGTTGAACCTG

AGCCCGCAGACGTACTTCTCCGTTCACACCGACAACGAGGACGGTACGCCGTTGAGCGGCA

GCAGCCTGCCGCCACCGTTTCCGCCGTGCACCTTGCGCACGGCATTGACCAAATACGCAGAC

TTGACTTCTGCACCGAAAAAGTCGGTGCTGGTGGCGCTGGCCGAGTACGCATCTGACCAGGG

TGAAGCGGATCGTTTGCGTTTCTTGGCGAGCCCGAGCGGCAAAGAGGAATATGCACAGTAC

ATCTTGGCAAGCCAGCGCACGCTGCTGGAGGTCATGGCGGAGTTCCCGTCGGCGAAACCGC

CGCTGGGTGTCTTTTTCGCGGGTGTCGCTCCGCGCCTGCAGCCGCGTTTCTATTCCATTAGCT

CTAGCCCGAAGATCGCACCGTTCCGTATTCACGTGACCTGCGCCCTGGTTTATGACAAATCC

CCTACCGGTCGCGTTCATAAGGGCATCTGTAGCACGTGGATGAAAAATGCGGTCCCGCTGGA

AGAAAGCAACGATTGTTCCTGGGCTCCGATCTTCGTCCGAACAGCAACTTCAAGCTGCCGA

CCGACCCGAAGGTTCCGATTATCATGATTGGTCCGGGTACCGGTCTGGCCCCTTTTCGTGGCT

TTTTGCAAGAGCGCTTGGCGTTGAAAGAGAGCGGTGCTGAATTGGGTCCGGCGATCTTGTTC

TTTGGTTGCCGTAACCGTAAAATGGACTTTATTTACGAGGATGAACTGAATGATTTCGTCAA

AGCGGGCGTTGTCAGCGAGCTGATCGTCGCTTTTAGCCGCGAAGGCCCGATGAAAGAATAC

GTGCAACACAAAATGAGCCAACGTGCCTCCGATGTGTGGAACATCATTAGCGACGGTGGTT

ATGTTTATGTTTGCGGTGACGCGAAGGGTATGGCTCGTGATGTTCACCGTACCCTGCATACC

ATCGCACAGGAGCAAGGTAGCATGTCCAGCTCGGAGGCCGAAGGTATGGTCAAAAACCTGC

AAACCACCGGTCGTTACCTGCGTGATGTGTGGTAA
```

Peptide fragment
                                                        SEQ ID NO: 17
MALLLAVFLGLSCLLLLSLW Peptide fragment
                                                        SEQ ID NO: 18
MALLLAVFWSALIILVLS DNA polylinker
                                                        SEQ ID NO: 19
GTCGACAATTAACCATGGTTAATTAAGCTTATATATGGTACCATATATGAATTCATTAATCTC
GAG 26 bp extension containing a spacer sequence, the SalI recognition
sequence and ribosome binding site (RBS)
                                                        SEQ ID NO: 20
GTCGACAATTAGGTAAAAAATAAACC 5' non-coding sequence comprising a HindIII recognition site
and a RBS sequence
                                                        SEQ ID NO: 21
AAGCTTAAGGAGGTAAAAA 3' non coding sequence comprising the KpnI, EcoRI and XhoI
recognition sites
                                                        SEQ ID NO: 22
GGTACCATATATGAATTCATTAATCTCGAG

The invention claimed is:

1. A method of producing one or more sesquiterpene compounds comprising:
   a. contacting an acyclic farnesyl diphosphate (FPP) with a polypeptide having a terpene synthase activity, wherein said polypeptide comprises an isovalencene synthase activity, a spirovetiva-1(10),7(11)-diene synthase activity and/or a valencene synthase activity, wherein the polypeptide comprises an amino acid sequence having at least 95% sequence identity to the amino acid sequence of SEQ ID NO: 1 or comprises the amino acid sequence of SEQ ID NO: 1, to produce one or more sesquiterpene compounds selected from the group consisting of isovalencene, spirovetiva-1(10),7(11)-diene, and valencene; and
   b. optionally isolating the one or more sesquiterpene compounds selected from the group consisting of isovalencene, spirovetiva-1(10),7(11)-diene and valencene.

2. The method of claim 1, comprising transforming a host cell or non-human organism with a nucleic acid encoding the polypeptide having the terpene synthase activity to recombinantly produce said polypeptide having the terpene synthase activity, wherein said polypeptide comprises an amino acid sequence having at least 95% sequence identity to the amino acid sequence of SEQ ID NO: 1 or comprises the amino acid sequence of SEQ ID NO: 1.

3. The method of claim 1, further comprising culturing a non-human host organism or host cell that produces FPP and has been transformed to express the polypeptide having the terpene synthase activity, wherein the polypeptide comprises an amino acid sequence having at least 95% sequence identity to the amino acid sequence of SEQ ID NO: 1 or comprises the amino acid sequence of SEQ ID NO: 1.

4. The method of claim 3, wherein the host cell or non-human organism is a prokaryotic organism, a plant, a microorganism, a bacterium, a yeast, or a fungus.

5. The method of claim 4, wherein the bacterium is *E. coli* and the yeast is *Saccharomyces cerevisiae*.

6. The method of claim 1, wherein the method produces a mixture of about 66 to 68% of isovalencene, about 25 to 26% of spirovetiva-1(10),7(11)-diene and about 6 to 9% of valencene.

7. A method of producing one or more sesquiterpene compound derivatives, the method comprising,
   producing one or more sesquiterpene compounds selected from the group consisting of isovalencene, spirovetiva-1(10),7(11)-diene and valencene by contacting an acyclic farnesol diphosphate (FPP) with a polypeptide having a terpene synthase activity, wherein said polypeptide comprises an isovalencene synthase activity, a spirovetiva-1(10),7(11)-diene synthase activity and/or a valencene synthase activity, wherein the polypeptide comprises an amino acid sequence having at least 95% sequence identity to the amino acid sequence of SEQ ID NO: 1 or comprises the amino acid sequence of SEQ ID NO: 1, and
   oxidizing the one or more sesquiterpene compounds selected from the group consisting of isovalencene, spirovetiva-1(10),7(11)-diene and valencene-to obtain derivatives of the one or more sesquiterpene compounds selected from the group consisting of isovalencene, spirovetiva-1(10),7(11)-diene and valencene by chemical and/or biochemical synthesis.

8. A method of producing one or more sesquiterpene compound derivatives, the method comprising,
   producing one or more sesquiterpene compounds selected from the group consisting of isovalencene, spirovetiva-1(10),7(11)-diene and valencene by contacting an acyclic farnesyl diphosphate (FPP) with a polypeptide having a terpene synthase activity, wherein said polypeptide comprises an isovalencene synthase activity, a spirovetiva-1(10),7(11)-diene synthase activity and/or a valencene synthase activity, wherein the polypeptide comprises an amino acid sequence having at least 95% sequence identity to the amino acid sequence of SEQ ID NO: 1 or comprises the amino acid sequence of SEQ ID NO:1, and
   contacting the one or more sesquiterpene compounds selected from the group consisting of isovalencene, spirovetiva-1(10),7(11)-diene and valencene with at least one oxidizing enzyme to produce derivatives of the one or more sesquiterpene compounds selected from the group consisting of isovalencene, spirovetiva-1(10),7(11)-diene and valencene,
   wherein the oxidizing enzyme is a cytochrome P450 polypeptide having cytochrome P450 oxidizing activity, wherein said cytochrome P450 polypeptide having cytochrome P450 oxidizing activity comprises an amino acid sequence at least 95% sequence identical to the amino acid sequence of SEQ ID NO: 7, 10, 12, or 14, or comprises the amino acid sequence of SEQ ID NO: 7, 10, 12, or 14.

9. The method of claim 8, wherein the at least one oxidizing enzyme is accompanied by a cytochrome P450 polypeptide having cytochrome P450 reductase activity, wherein said cytochrome P450 polypeptide having cytochrome P450 reductase activity comprises an amino acid sequence at least 95% sequence identical to the amino acid sequence of SEQ ID NO: 15 or comprises the amino acid sequence of SEQ ID NO: 15.

10. The method of claim 8, wherein the at least one oxidizing enzyme is heterologously expressed in a host cell.

11. The method of claim 7, wherein the one or more sesquiterpene compounds selected from the group consisting of isovalencene, spirovetiva-1(10),7(11)-diene and valencene are oxidized using a wild type organism selected from the group consisting of a prokaryotic cell and a eukaryotic cell.

12. The method of claim 9, wherein the at least one oxidizing enzyme, the polypeptide having the terpene synthase activity, and/or the cytochrome P450 polypeptide having cytochrome P450 reductase activity are expressed in the same host cell.

13. The method of claim 7, wherein the oxidation is an allylic oxidation.

14. A method of producing oxygenated sesquiterpene compounds comprising
  oxidizing one or more sesquiterpene compounds to one or more oxygenated sesquiterpene compounds by chemical and/or biochemical synthesis with a cytochrome P450 polypeptide having cytochrome P450 oxidizing activity, wherein the cytochrome P450 polypeptide oxidizes the one or more sesquiterpene compounds accompanied by a cytochrome P450 reductase enzyme for electron transfer to the cytochrome P450 polypeptide,
  wherein the one or more sesquiterpene compounds being oxidized are selected from the group consisting of isovalencene, spirovetiva-1(10),7(11)-diene and valencene, wherein the cytochrome P450 reductase enzyme comprises an amino acid sequence at least 95% sequence identical to the amino acid sequence of SEQ ID NO:15 or comprises the amino acid sequence of SEQ ID NO:15, and
  wherein the cytochrome P450 polypeptide having cytochrome P450 oxidizing activity comprises an amino acid sequence at least 95% sequence identical to the amino acid sequence of SEQ ID NO: 7, 10, 12, or 14, or comprises the amino acid sequence of SEQ ID NO: 7, 10, 12, or 14.

15. The method of claim 14, wherein the one or more oxygenated sesquiterpene compounds are selected from the group consisting of isovalencenol, nootkatol, β-vetivol, isonootkatol, and combinations thereof.

16. The method of claim 14, wherein the one or more oxygenated sesquiterpene compounds are further oxidized to oxygenated sesquiterpene compounds selected from the group consisting nootkatone, α-vetivone, β-vetivone, and combinations thereof.

* * * * *

SEQUENCE LISTING

<160> NUMBER OF SEQ ID NOS: 22

<210> SEQ ID NO 1
<211> LENGTH: 567
<212> TYPE: PRT
<213> ORGANISM: Vetiveria zizanoides

<400> SEQUENCE: 1

```
Met Ala Ala Ser Ile Thr Val Ala Ala His Gly Pro Pro Ala Ala
1               5                   10                  15

Ile Pro Glu Thr Lys Arg Ser Thr Val Asp Val Pro Phe Gln Ser
            20                  25                  30

Ser Val Trp Gly Asp Tyr Phe Val Asn Tyr Thr Pro Pro Ala Ser Gln
        35                  40                  45

Arg Ser Glu Glu Trp Met Arg Glu Val Asp Glu Leu Arg Gly Glu
50                  55                  60

Val Arg Arg Lys Phe Lys Thr Thr Met Ser Met Ala Glu Thr Met Val
65                  70                  75                  80

Leu Val Asp Thr Leu Glu Arg Leu Ala Ile Asp Gly His Phe Arg Lys
                85                  90                  95

Asp Ile Asp Leu Ala Leu Ser Gln Ile His Met Glu Gly Lys Pro Ala
            100                 105                 110

Gly Ile Ser Ser Ser Asn Lys Leu Tyr Ile Val Ala Leu Gly Phe Arg
        115                 120                 125

Leu Leu Arg Gln His Gly Phe Trp Val Ser Ala Asp Val Phe Asp Lys
    130                 135                 140

Phe Arg Asp Ser Thr Gly Lys Leu Ser Lys Gly Leu Ser Gly Asp Val
145                 150                 155                 160

Lys Gly Leu Leu Ser Leu Tyr Asn Ala Ala His Met Ala Val Pro Gly
                165                 170                 175

Glu Lys Ser Leu Asp Glu Ala Ile Asp Phe Thr Arg Arg Cys Leu Glu
            180                 185                 190

Ser Ala Lys Asp Arg Leu Val Ala Pro Met Ser Val Gln Val Ser Arg
        195                 200                 205

Ala Leu Ser Ile Pro Leu Pro Arg Tyr Leu Pro Arg Leu Glu Ala Met
    210                 215                 220

His Tyr Ile Ser Glu Tyr Gly Gln Glu Glu Asp His Asp Ala Lys Ile
225                 230                 235                 240

Leu Glu Leu Ala Arg Leu Asp Tyr Ala Leu Val Gln Ser Leu Tyr Leu
                245                 250                 255

Lys Glu Leu Arg Glu Leu Thr Leu Trp Trp Lys Glu Leu Tyr His Ser
            260                 265                 270

Val Asn Leu Pro Asn Thr Arg Asp Arg Ile Val Glu Met Tyr Phe Phe
        275                 280                 285

Ala Phe Gly Met Leu Gln Thr Glu Glu Tyr Ser Arg Ala Arg Leu Ile
    290                 295                 300

Asp Ser Lys Ile Ile Ala Leu Val Ser Leu Met Asp Asp Ile Tyr Asp
305                 310                 315                 320

Glu His Ala Ser Phe Glu Glu Ala Gln Lys Phe Asn Glu Ala Ile Gln
                325                 330                 335

Arg Trp Asn Glu Ser Ala Val Ser Asp Leu Pro Glu Tyr Met Arg Met
            340                 345                 350

Leu Tyr Thr Gln Ile Leu Ser Thr Phe Ala Lys Phe Glu Glu Val Leu
        355                 360                 365
```

-continued

```
Gly Pro Asn Glu Lys Tyr Arg Val Ser Tyr Ala Lys Glu Ala Tyr Lys
    370                 375                 380

Leu Gln Ser Met Tyr Tyr Phe Leu Glu Asn Lys Trp Cys His Glu Asn
385                 390                 395                 400

His Met Pro Ser Phe Gly Glu His Ile His Leu Ser Ser Met Ser Ala
                405                 410                 415

Gly Leu Gln Val Leu Ile Val Gly Ala Trp Ile Gly Ala His His Ala
            420                 425                 430

Ile Ala Lys Glu Ser Leu Glu Trp Ala Ile Thr Tyr Pro Glu Val Phe
        435                 440                 445

Arg Ala Ala Gly Asp Val Gly Arg Leu Leu Asn Asp Ile Ala Ser Phe
    450                 455                 460

Lys Lys Arg Lys Asn Ser Lys Asp Ala Pro Asn Ala Leu Glu Cys Tyr
465                 470                 475                 480

Val Arg Glu His Gly Val Thr Gly Glu Glu Ala Ala Ala Ala Cys Ala
                485                 490                 495

Ala Ile Val Glu Leu Gly Trp Arg Lys Ile Asn Arg Ala Arg Met Glu
            500                 505                 510

Ile His Pro Met Leu Val Pro Ala Ala Gln Met Asp Ala Lys Ile Asn
        515                 520                 525

Leu Thr Arg Val Cys Glu Ile Leu Tyr Tyr Arg Gly Met Asp Gly Tyr
    530                 535                 540

Thr Phe Gly Ser Asp Leu Arg Asp Val Ile Thr Ser Leu Phe Ile Lys
545                 550                 555                 560

Pro Ala Ala Gly Gly Pro Ala
                565
```

<210> SEQ ID NO 2
<211> LENGTH: 1835
<212> TYPE: DNA
<213> ORGANISM: Vetiveria zizanoides

<400> SEQUENCE: 2

```
actggagttc agacgtgtgc tcttccgatc tatcggagtg aagttgagca gctaacttca      60
cgactcgttt gcaggctagc tcgcaacaga atagagagtg ttactgctgg tatatatata     120
tatatatata tggctgcgag cattactgtc gccgccgcac atgggcctcc tgctgcaatc     180
ccagagacca aacgcagcac tgtagacgac gttcctttcc aatcctctgt gtggggcgac     240
tactttgtaa actacacacc tcctgcatca cagaggtcgg aggaatggat gagggagagg     300
gttgatgaac tcaggggtga agtgcgccgg aagttcaaaa cgacgatgag catggccgag     360
acgatggtgc tggtggacac actggagcgc ctcgccatcg acggccattt ccgcaaggat     420
attgacttgg cgttgagcca aatccacatg gaggggaagc cggccggtat tagcagctcc     480
aacaagcttt acatcgtcgc cctgggattc cgcttgctta ggcaacatgg cttctgggta     540
tccgcagacg tgtttgacaa gtttagggat agcacgggca agcttagcaa gggtctgagc     600
ggcgacgtga agggtctgct gagcctatac aacgcggctc acatggcggt tcccggcgag     660
aaaagcctgg acgaagccat cgacttcaca aggcgctgcc tcgagtctgc caaggacagg     720
ctcgtggcgc cgatgtcggt gcaggtgtcg cgcgccctca gcattcctct cccccgctac     780
ctgccgcggc tagaggccat gcactacatc tcagagtatg ggcaggagga ggaccatgac     840
gccaagatcc tggagcttgc gaggctggac tatgcccttg tccagtctct ctatctcaag     900
gagctcaggg agctcacctt gtggtggaag gagctgtatc acagcgtgaa tctgcccaac     960
```

| | |
|---|---|
| acacgggacc gcatcgtgga gatgtacttc tttgcatttg gtatgctgca gacggaggag | 1020 |
| tactctcggg cgcgcctgat tgatagcaag ataattgcac tggtcagcct gatggatgac | 1080 |
| atttacgacg aacacgctag cttttgaggaa gcccaaaaat tcaatgaagc catacagaga | 1140 |
| tggaatgaaa gtgcggtctc agacctacca gaatacatgc gcatgctata cacccaaata | 1200 |
| ctaagcacct tcgccaaatt tgaggaagtt ttggggccca acgaaaagta ccgcgtgtct | 1260 |
| tacgccaaag aggcgtacaa attgcagtcg atgtattact ttctggagaa caaatggtgt | 1320 |
| cacgagaacc acatgccaag cttcggagag cacatacatc tttcttccat gtcggcaggc | 1380 |
| ttgcaggtgt tgatcgttgg ggcatggata ggcgcccacc acgccattgc caaggagtca | 1440 |
| ctagagtggg caatcaccta ccctgaagtc ttccgggcag caggagatgt tggccgtctc | 1500 |
| ctcaacgata tcgcttcatt taagaagagg aaaaacagca aggacgcgcc caacgcgctg | 1560 |
| gagtgctacg tcagagaaca tggcgtcacg ggggaggaag ctgcggccgc gtgtgcagcc | 1620 |
| attgtagagc tcggtggag gaagatcaac agggcccgta tggagataca tcctatgctg | 1680 |
| gtacccgcgg cacaaatgga tgcgaaaatc aacctgacca gggtgtgcga gattttatac | 1740 |
| taccgtggta tggatggcta cacctttgga agcgacctcc gggatgtcat cacttctctc | 1800 |
| ttcatcaagc cggcggccgg gggccctgca taatt | 1835 |

<210> SEQ ID NO 3
<211> LENGTH: 1704
<212> TYPE: DNA
<213> ORGANISM: Vetiveria zizanoides

<400> SEQUENCE: 3

| | |
|---|---|
| atggctgcga gcattactgt cgccgccgca catgggcctc ctgctgcaat cccagagacc | 60 |
| aaacgcagca ctgtagacga cgttcctttc caatcctctg tgtgggggcga ctactttgta | 120 |
| aactacacac ctcctgcatc acagaggtcg gaggaatgga tgagggagag ggttgatgaa | 180 |
| ctcagggggtg aagtgcgccg gaagttcaaa acgacgatga gcatggccga gacgatggtg | 240 |
| ctggtggaca cactggagcg cctcgccatc gacggccatt tccgcaagga tattgacttg | 300 |
| gcgttgagcc aaatccacat ggaggggaag ccggccggta ttagcagctc caacaagctt | 360 |
| tacatcgtcg ccctgggatt ccgcttgctt aggcaacatg gcttctgggt atccgcagac | 420 |
| gtgtttgaca gtttaggga tagcacgggc aagcttagca aggtctgag cggcgacgtg | 480 |
| aagggtctgc tgagcctata caacgcggct cacatggcgg ttcccggcga gaaaagcctg | 540 |
| gacgaagcca tcgacttcac aaggcgctgc ctcgagtctg ccaaggacag gctcgtggcg | 600 |
| ccgatgtcgg tgcaggtgtc gcgcgccctc agcattcctc tccccgcta cctgccgcgg | 660 |
| ctagaggcca tgcactacat ctcagagtat gggcaggagg aggaccatga cgccaagatc | 720 |
| ctggagcttg cgaggctgga ctatgccctt gtccagtctc tctatctcaa ggagctcagg | 780 |
| gagctcacct tgtggtggaa ggagctgtat cacagcgtga atctgcccaa cacacgggac | 840 |
| cgcatcgtgg agatgtactt ctttgcattt ggtatgctgc agacggagga gtactctcgg | 900 |
| gcgcgcctga ttgatagcaa gataattgca ctggtcagcc tgatggatga catttacgac | 960 |
| gaacacgcta gctttgagga agcccaaaaa ttcaatgaag ccatacagag atggaatgaa | 1020 |
| agtgcggtct cagacctacc agaatacatg cgcatgctat acacccaaat actaagcacc | 1080 |
| ttcgccaaat ttgaggaagt tttggggccc aacgaaaagt accgcgtgtc ttacgccaaa | 1140 |
| gaggcgtaca aattgcagtc gatgtattac tttctggaga caaatggtg tcacgagaac | 1200 |
| cacatgccaa gcttcggaga gcacatacat ctttcttcca tgtcggcagg cttgcaggtg | 1260 |

```
ttgatcgttg gggcatggat aggcgcccac cacgccattg ccaaggagtc actagagtgg    1320
gcaatcacct accctgaagt cttccgggca gcaggagatg ttggccgtct cctcaacgat    1380
atcgcttcat ttaagaagag gaaaaacagc aaggacgcgc ccaacgcgct ggagtgctac    1440
gtcagagaac atggcgtcac gggggaggaa gctgcggccg cgtgtgcagc cattgtagag    1500
ctcgggtgga ggaagatcaa cagggcccgt atggagatac atcctatgct ggtacccgcg    1560
gcacaaatgg atgcgaaaat caacctgacc agggtgtgcg agattttata ctaccgtggt    1620
atggatggct acacctttgg aagcgacctc cgggatgtca tcacttctct cttcatcaag    1680
ccggcggccg ggggccctgc ataa                                          1704
```

<210> SEQ ID NO 4
<211> LENGTH: 1704
<212> TYPE: DNA
<213> ORGANISM: Artificial Sequence
<220> FEATURE:
<223> OTHER INFORMATION: VzTps1718 codon optimized cDNA

<400> SEQUENCE: 4

```
atggcagcaa gcatcacggt cgccgcagca cacggtccgc cagcagcaat cccggaaacc     60
aaacgcagca ccgtggatga cgttccattt caatcctcgg tgtggggcga ctacttcgtc    120 aactatcgc cgccggcgag ccagcgttcc gaagagtgga tgcgtgaacg cgttgacgaa    180
ctgcgtggcg aagtgcgtcg taagttcaag actaccatga gcatggctga aaccatggtt    240
ctggttgata ccctggagcg ccttgcaatc gatggtcatt ttcgtaaaga tattgacctg    300
gcactgagcc agatccacat ggagggtaaa ccggcgggta ttagctcgtc taacaagctg    360
tatatcgttg cgctgggctt tcgtttgttg cgtcagcacg gtttctgggt gagcgccgat    420
gttttcgata aatttcgtga tagcacgggc aaactgtcca agggcctgag cggcgacgtc    480
aagggcctgc tgtcactgta taatgccgca cacatggctg tcccgggtga gaaatctctg    540
gatgaagcga ttgactttac gcgtcgctgc ctggaaagcg ccaaagatcg tttggtggcc    600
ccgatgagcg tccaggttag ccgcgccctg agcatcccgc tgccgcgtta tctgccgcgc    660
ctggaagcga tgcattacat cagcgagtat ggtcaagagg aagatcacga cgctaagatc    720
ctggaattgg cgcgcctgga ctacgcgctg gtccaaagcc tgtacctgaa gaactgcgc    780 gagctgaccc tgtggtggaa agaactgtac cactccgtta atctgccgaa cacccgtgac    840
cgcatcgtcg agatgtattt ctttgcgttt ggtatgttgc agaccgaaga gtactctcgt    900
gctcgcctga tcgatagcaa gattatcgcc tggtgagcc tgatggatga catttatgat    960
gagcatgcca gcttcgagga agctcaaaag tttaacgaag caatccaacg ttggaatgaa   1020
agcgcggtta cgacttgcc ggagtatatg cgcatgctgt acacccaaat cctgagcacc   1080
ttcgcgaagt ttgaagaggt tctgggtccg aacgaaaaat atcgcgtgag ctatgcgaaa   1140
gaggcgtaca gctgcaatc catgtactat ttcctggaga caaatggtg tcatgagaat   1200 cacatgccga gcttcggtga gcacattcac ctgagctcca tgtccgcggg tttgcaagtg   1260
ttgattgtgg gtgcttggat cggcgcacat catgccattg caaaagagag cctggagtgg   1320
gcgattacct accctgaagt ttttcgtgcc gcgggcgatg tgggtcgtct gttgaatgac   1380 attcaagct tcaaaaagcg taagaactct aaagacgccc cgaacgcgct ggagtgttat   1440
gtccgtgaac acggcgtgac tggcgaagaa gcggcagctg cctgcgcagc tattgttgag   1500
ctgggttggc gtaagatcaa ccgtgcgcgc atggaaatcc atccgatgct ggtcccggcg   1560
```

```
gcgcagatgg acgcgaaaat caatttgacc cgtgtgtgcg agatcctgta ctaccgtggc   1620
atggatggtt acaccttcgg tagcgattta cgcgatgtga ttacgagcct cttcattaag   1680
cctgcggctg gcggcccggc gtaa                                          1704
```

<210> SEQ ID NO 5
<211> LENGTH: 1825
<212> TYPE: DNA
<213> ORGANISM: Vetiveria zizanoides

<400> SEQUENCE: 5

```
gatcgtttca cgtgactgga gttcagacgt gtgctcttcc gatctcaaaa aatggacttt     60
ctcagaatcc cgtttcttgt agccttcgtc ttcctcgccg tccttctcag gctcatccgg    120
agctacatca catcctcagc tcttcgcctg ccaccggggc catggcagct gccgctcatc    180
ggcagcctgc accacctcct gctgtcgcgc ttcagcgacc tccctcaccg ggctttgcgc    240
gagatgtccg gcacctacgg gcccctcatg ctgctccgct tcggctccgt gcccacgctg    300
gtggtctcct ccgccgaggc tgcccgggag gtgatgagga cccacgacct cgccttctgc    360
gaccgccacc tcggcgtcac tctcgacatc gtcacctgcg gcggcaagga catcatctgc    420 tcccctaca cgcccactg gcgcgagctc cgtaagctgt gcatggtcga gatcttgagc      480
cagcggcgcg tgctctcgtt ccggagcatc cgggaagagg aggtggcgag cctcgtccgc    540
tccatctccg acgagtgcgg cggtggccag cagcccgtca acctcactga agggataagc    600
cgcatgataa cgacgtcgc cgcgcgcacg gtcgtcggcg accggtgcaa gtaccaggat     660
gaatacatgc atgagctgga cgaagtggtg cggctggccg gcgggttcaa cctggcggac    720
ctgtacccgt cctcgcggct ggtacggcgg ttcagcgccg ccgcgaggga cgcgaggagg    780
tgccagagga acatgtaccg tatcatccag agcatcatcc aggagcgtga agccatgccg    840
acgccagagc gagacgagga ggacctcctc ggcgtcctcc tcaggctgca gagagaaggt    900
ggcctgcagt ttgctctcac caatgagata gtcagcaccg tcatttacga tattttttct    960
gctggtagtg aaacatcatc aactgttcta gtatgggcaa tgtcggagct tgttaagaat   1020
ccacaagtca tgcgtaaggc ccagtcgag gtgagggata ccttcaaagg aaacaacaag    1080
ataactgaaa gtgatttgat caagttaaga tatctacaac tggtgatcaa ggagacttta   1140
cggttgcatg ctccggtacc actcttgctc cctcgagaat gccgtgagtc atgtcagatt   1200
atgggttacg atgtgctaaa gggaaccaag gtatttgtga atgcttgggc aatagcaagg   1260
gacacgggat tatggtgtga tggagaggaa tttaggccag aaaggtttga agtagcaat    1320 attgatttca ggggtaatga ctttgagttc acaccgtttg gggcaggcag agagtatgc    1380 cctggcatca cacttggact ggccaaccta gaactagcgc ttgctagcct tctttatcat   1440
tttgattggg atctgcccaa tggtgccagg ttggaagatc ttgatatggc agaggccttt   1500
ggtataacgt taaaaggaa gtccatgctc tggctcaagg ccaaaccta caataatttt     1560 ataccaaatt aatcaggtga tttgtgatgt gaactatccc ggttgctact tagtttatta   1620
tacccagaaa gagtgtgatg gtaattgtac tatcaatctt tactgcagaa cagtaaatat   1680
atccagagtt ggttctatgc ttctgttata atgtttcatc actctgtatt aagtgtgtag   1740
ttatctgttt gtttacttt tttgtaatga ttaaacgatt atctaatgag agtacaagaa    1800
tcaaatgaga ctggtctaaa aaaaa                                         1825
```

<210> SEQ ID NO 6
<211> LENGTH: 1521

```
<212> TYPE: DNA
<213> ORGANISM: Vetiveria zizanoides

<400> SEQUENCE: 6
atggactttc tcagaatccc gtttcttgta gccttcgtct tcctcgccgt ccttctcagg      60
ctcatccgga gctacatcac atcctcagct cttcgcctgc caccggggcc atggcagctg     120
ccgctcatcg gcagcctgca ccacctcctg ctgtcgcgct tcagcgacct ccctcaccgg     180
gctttgcgcg agatgtccgg cacctacggg cccctcatgc tgctccgctt cggctccgtg     240
cccacgctgg tggtctcctc cgccgaggct gcccgggagg tgatgaggac ccacgacctc     300
gccttctgcg accgccacct cggcgtcact ctcgacatcg tcacctgcgg cggcaaggac     360
atcatctgct cccccctacaa cgcccactgg cgcgagctcc gtaagctgtg catggtcgag     420
atcttgagcc agcggcgcgt gctctcgttc cggagcatcc gggaagagga ggtggcgagc     480
ctcgtccgct ccatctccga cgagtgcggc ggtggccagc agcccgtcaa cctcactgaa     540
gggataagcc gcatgataaa cgacgtcgcc gcgcgcacgg tcgtcggcga ccggtgcaag     600
taccaggatg aatacatgca tgagctggac gaagtggtgc ggctggccgg cggttcaac     660
ctggcggacc tgtacccgtc ctcgcggctg gtacggcggt tcagcgccgc cgcgagggac     720
gcgaggaggt gccagaggaa catgtaccgt atcatccaga gcatcatcca ggagcgtgaa     780
gccatgccga cgccagagcg agacgaggag gacctcctcg cgtcctcct caggctgcag     840
agagaaggtg gcctgcagtt tgctctcacc aatgagatag tcagcaccgt catttacgat     900
atttttctg ctggtagtga aacatcatca actgttctag tatgggcaat gtcggagctt     960
gttaagaatc cacaagtcat gcgtaaggcc cagtcagagg tgagggatac cttcaaagga    1020
aacaacaaga taactgaaag tgatttgatc aagttaagat atctacaact ggtgatcaag    1080
gagactttac ggttgcatgc tccggtacca ctcttgctcc ctcgagaatg ccgtgagtca    1140
tgtcagatta tgggttacga tgtgctaaag ggaaccaagg tatttgtgaa tgcttgggca    1200
atagcaaggg acacgggatt atggtgtgat ggagaggaat ttaggccaga aaggtttgaa    1260
agtagcaata ttgatttcag gggtaatgac tttgagttca caccgtttgg ggcaggcagg    1320
agagtatgcc ctggcatcac acttggactg gccaacctag aactagcgct tgctagcctt    1380
ctttatcatt ttgattggga tctgcccaat ggtgccaggt tggaagatct tgatatggca    1440
gaggcctttg gtataacgtt aaaaaggaag tccatgctct ggctcaaggc caaaccttac    1500
aataatttta taccaaatta a                                              1521

<210> SEQ ID NO 7
<211> LENGTH: 506
<212> TYPE: PRT
<213> ORGANISM: Vetiveria zizanoides

<400> SEQUENCE: 7

Met Asp Phe Leu Arg Ile Pro Phe Leu Val Ala Phe Val Phe Leu Ala
1               5                  10                  15

Val Leu Leu Arg Leu Ile Arg Ser Tyr Ile Thr Ser Ser Ala Leu Arg
            20                  25                  30

Leu Pro Pro Gly Pro Trp Gln Leu Pro Leu Ile Gly Ser Leu His His
        35                  40                  45

Leu Leu Leu Ser Arg Phe Ser Asp Leu Pro His Arg Ala Leu Arg Glu
    50                  55                  60

Met Ser Gly Thr Tyr Gly Pro Leu Met Leu Leu Arg Phe Gly Ser Val
65                  70                  75                  80
```

```
Pro Thr Leu Val Val Ser Ser Ala Glu Ala Ala Arg Glu Val Met Arg
                85                  90                  95

Thr His Asp Leu Ala Phe Cys Asp Arg His Leu Gly Val Thr Leu Asp
            100                 105                 110

Ile Val Thr Cys Gly Gly Lys Asp Ile Ile Cys Ser Pro Tyr Asn Ala
        115                 120                 125

His Trp Arg Glu Leu Arg Lys Leu Cys Met Val Glu Ile Leu Ser Gln
    130                 135                 140

Arg Arg Val Leu Ser Phe Arg Ser Ile Arg Glu Glu Val Ala Ser
145                 150                 155                 160

Leu Val Arg Ser Ile Ser Asp Glu Cys Gly Gly Gln Gln Pro Val
                165                 170                 175

Asn Leu Thr Glu Gly Ile Ser Arg Met Ile Asn Asp Val Ala Ala Arg
            180                 185                 190

Thr Val Val Gly Asp Arg Cys Lys Tyr Gln Asp Glu Tyr Met His Glu
        195                 200                 205

Leu Asp Glu Val Val Arg Leu Ala Gly Gly Phe Asn Leu Ala Asp Leu
    210                 215                 220

Tyr Pro Ser Ser Arg Leu Val Arg Arg Phe Ser Ala Ala Ala Arg Asp
225                 230                 235                 240

Ala Arg Arg Cys Gln Arg Asn Met Tyr Arg Ile Ile Gln Ser Ile Ile
                245                 250                 255

Gln Glu Arg Glu Ala Met Pro Thr Pro Glu Arg Asp Glu Glu Asp Leu
            260                 265                 270

Leu Gly Val Leu Leu Arg Leu Gln Arg Glu Gly Gly Leu Gln Phe Ala
        275                 280                 285

Leu Thr Asn Glu Ile Val Ser Thr Val Ile Tyr Asp Ile Phe Ser Ala
    290                 295                 300

Gly Ser Glu Thr Ser Ser Thr Val Leu Val Trp Ala Met Ser Glu Leu
305                 310                 315                 320

Val Lys Asn Pro Gln Val Met Arg Lys Ala Gln Ser Glu Val Arg Asp
                325                 330                 335

Thr Phe Lys Gly Asn Asn Lys Ile Thr Glu Ser Asp Leu Ile Lys Leu
            340                 345                 350

Arg Tyr Leu Gln Leu Val Ile Lys Glu Thr Leu Arg Leu His Ala Pro
        355                 360                 365

Val Pro Leu Leu Leu Pro Arg Glu Cys Arg Glu Ser Cys Gln Ile Met
    370                 375                 380

Gly Tyr Asp Val Leu Lys Gly Thr Lys Val Phe Val Asn Ala Trp Ala
385                 390                 395                 400

Ile Ala Arg Asp Thr Gly Leu Trp Cys Asp Gly Glu Glu Phe Arg Pro
                405                 410                 415

Glu Arg Phe Glu Ser Ser Asn Ile Asp Phe Arg Gly Asn Asp Phe Glu
            420                 425                 430

Phe Thr Pro Phe Gly Ala Gly Arg Arg Val Cys Pro Gly Ile Thr Leu
        435                 440                 445

Gly Leu Ala Asn Leu Glu Leu Ala Leu Ala Ser Leu Leu Tyr His Phe
    450                 455                 460

Asp Trp Asp Leu Pro Asn Gly Ala Arg Leu Glu Asp Leu Asp Met Ala
465                 470                 475                 480

Glu Ala Phe Gly Ile Thr Leu Lys Arg Lys Ser Met Leu Trp Leu Lys
                485                 490                 495
```

-continued

```
Ala Lys Pro Tyr Asn Asn Phe Ile Pro Asn
            500                 505

<210> SEQ ID NO 8
<211> LENGTH: 1524
<212> TYPE: DNA
<213> ORGANISM: Artificial Sequence
<220> FEATURE:
<223> OTHER INFORMATION: VzCP8201-228093, optimized DNA sequence
      encoding for VzCP8201-12, including NdeI site at 5'end and
      polylinker at 3'end

<400> SEQUENCE: 8
atggcactgt tgttggctgt ttttttgggt ttgagctgtt tgttgctgtt gagcttgtgg     60
cgtctgatcc gcagctacat tacttccagc gcgctgcgcc tgccgccggg tccgtggcag    120
ctgcctctga ttggcagcct gcaccacttg ctgctgagcc gcttcagcga cttgccgcat    180
cgcgcgctga gagagatgag cggcacctac ggtccgctga tgctgctgcg tttcggtagc    240
gtcccgaccc tggttgtctc tagcgcggaa gcggctcgtg aagtcatgcg tacccacgat    300
ctggcgtttt gcgatcgtca cctgggtgtg acgctggaca tcgtaacctg tggtggcaaa    360
gacatcatct gcagcccata caacgctcat tggcgtgagc tgcgcaagct gtgcatggtt    420
gaaatcctga gccagcgccg tgtgctgagc ttccgttcga ttcgtgaaga agaggtcgcg    480
agcctggtgc gttccattag cgatgagtgt ggtggcggcc agcaaccagt taacctgacc    540
gaaggcatct ctcgcatgat taatgacgtc gccgcacgta ccgtggtcgg tgaccgctgc    600
aagtaccaag acgagtacat gcatgaactg gacgaagttg ttcgtctggc gggtggcttc    660
aacctggccg atctgtatcc gagctcacgt ctggttcgtc gtttttccgc agctgcgcgt    720
gacgcgcgtc gctgtcagcg taacatgtac cgcattattc aatctatcat ccaagagcgt    780
gaggcaatgc cgacgcctga gcgcgacgaa gaagatcttc tgggtgtcct gctgcgtctg    840
cagcgcgagg gtggtctgca gtttgcgctg acgaacgaaa ttgtttcgac cgtgatttac    900
gatatcttca gcgccggtag cgaaacctcc agcacggtgt tggtgtgggc aatgtctgaa    960
ctggtcaaaa atccgcaagt gatgcgcaaa gcgcaaagcg aagttcgtga cactttcaaa   1020
ggtaacaata agattaccga gagcgacctg attaagctgc gctatctgca actggttatc   1080
aaagaaaccc tgcgcctgca cgcaccggtg ccgctgctgc tgccgcgtga gtgccgtgaa   1140
tcctgtcaga tcatgggcta tgacgttctg aagggtacga aagtgttcgt taatgcctgg   1200
gcgattgcac gtgatacggg tctgtggtgc gacggcgaag agttccgtcc ggagcgtttc   1260
gagtccagca atatcgattt tcgtggtaat gattttgagt tcacgccgtt cggtgcgggc   1320
cgtcgtgtct gcccaggcat caccctgggc ctggccaact tagaactggc cctcgcgagc   1380
ttgttatatc actttgactg ggatctgccg aacggcgcgc gcctggaaga tctggacatg   1440
gccgaggcat ttggtatcac gctgaagcgc aagagcatgc tgtggctgaa agcaaaaccg   1500
tacaataatt ttattccgaa ctaa                                          1524

<210> SEQ ID NO 9
<211> LENGTH: 1524
<212> TYPE: DNA
<213> ORGANISM: Artificial Sequence
<220> FEATURE:
<223> OTHER INFORMATION: VzCP8201-228092, optimized DNA sequence
      encoding for VzCP8201-12-bov, including NdeI site at 5'end and
      polylinker at 3'end

<400> SEQUENCE: 9
```

| | | |
|---|---|---|
| atggcactgt tgttggctgt ttttttgggt tgagctgtt tgttgctgtt gagcttgtgg | 60 |
| cgtctgatcc gcagctacat tacttccagc gcgctgcgcc tgccgccggg tccgtggcag | 120 |
| ctgcctctga ttggcagcct gcaccacttg ctgctgagcc gcttcagcga cttgccgcat | 180 |
| cgcgcgctga gagagatgag cggcacctac ggtccgctga tgctgctgcg tttcggtagc | 240 |
| gtcccgaccc tggttgtctc tagcgcggaa gcggctcgtg aagtcatgcg tacccacgat | 300 |
| ctggcgtttt gcgatcgtca cctgggtgtg acgctggaca tcgtaacctg tggtggcaaa | 360 |
| gacatcatct gcagcccata caacgctcat tggcgtgagc tgcgcaagct gtgcatggtt | 420 |
| gaaatcctga ccagcgccg tgtgctgagc ttccgttcga ttcgtgaaga agaggtcgcg | 480 |
| agcctggtgc gttccattag cgatgagtgt ggtggcggcc agcaaccagt taacctgacc | 540 |
| gaaggcatct ctcgcatgat taatgacgtc gccgcacgta ccgtggtcgg tgaccgctgc | 600 |
| aagtaccaag acgagtacat gcatgaactg gacgaagttg ttcgtctggc gggtggcttc | 660 |
| aacctggccg atctgtatcc gagctcacgt ctggttcgtc gttttttccgc agctgcgcgt | 720 |
| gacgcgcgtc gctgtcagcg taacatgtac cgcattattc aatctatcat ccaagagcgt | 780 |
| gaggcaatgc cgacgcctga gcgcgacgaa gaagatcttc tgggtgtcct gctgcgtctg | 840 |
| cagcgcgagg tggtctgca gttttgcgctg acgaacgaaa ttgtttcgac cgtgatttac | 900 |
| gatatcttca cgccggtag cgaaacctcc agcacggtgt tggtgtgggc aatgtctgaa | 960 |
| ctggtcaaaa atccgcaagt gatgcgcaaa gcgcaaagcg aagttcgtga cacttttcaaa | 1020 |
| ggtaacaata agattaccga gagcgacctg attaagctgc gctatctgca actggttatc | 1080 |
| aaagaaaccc tgcgcctgca cgcaccggtg ccgctgctgc tgccgcgtga gtgccgtgaa | 1140 |
| tcctgtcaga tcatgggcta tgacgttctg aagggtacga aagtgttcgt taatgcctgg | 1200 |
| gcgattgcac gtgatacggg tctgtggtgc gacggcgaag agttccgtcc ggagcgtttc | 1260 |
| gagtccagca atatcgattt tcgtggtaat gatttttgagt tcacgccgtt cggtgcgggc | 1320 |
| cgtcgtgtct gcccaggcat caccctgggc ctggccaact agaactggc cctcgcgagc | 1380 |
| ttgttatatc actttgactg ggatctgccg aacggcgcgc gcctggaaga tctggacatg | 1440 |
| gccgaggcat ttggtatcac gctgaagcgc aagagcatgc tgtggctgaa agcaaaaccg | 1500 |
| tacaataatt ttattccgaa ctaa | 1524 |

<210> SEQ ID NO 10
<211> LENGTH: 507
<212> TYPE: PRT
<213> ORGANISM: Artificial Sequence
<220> FEATURE:
<223> OTHER INFORMATION: VzCP8201-12-bov, amino acid sequence of
    N-terminal variant of VzCP8201-12

<400> SEQUENCE: 10

Met Ala Leu Leu Leu Ala Val Phe Leu Gly Leu Ser Cys Leu Leu Leu
1               5                   10                  15

Leu Ser Leu Trp Arg Leu Ile Arg Ser Tyr Ile Thr Ser Ser Ala Leu
            20                  25                  30

Arg Leu Pro Pro Gly Pro Trp Gln Leu Pro Leu Ile Gly Ser Leu His
        35                  40                  45

His Leu Leu Leu Ser Arg Phe Ser Asp Leu Pro His Arg Ala Leu Arg
    50                  55                  60

Glu Met Ser Gly Thr Tyr Gly Pro Leu Met Leu Leu Arg Phe Gly Ser
65                  70                  75                  80

Val Pro Thr Leu Val Val Ser Ser Ala Glu Ala Ala Arg Glu Val Met

```
                    85                  90                  95
Arg Thr His Asp Leu Ala Phe Cys Asp Arg His Leu Gly Val Thr Leu
                100                 105                 110

Asp Ile Val Thr Cys Gly Gly Lys Asp Ile Ile Cys Ser Pro Tyr Asn
                115                 120                 125

Ala His Trp Arg Glu Leu Arg Lys Leu Cys Met Val Glu Ile Leu Ser
                130                 135             140

Gln Arg Arg Val Leu Ser Phe Arg Ser Ile Arg Glu Glu Val Ala
145                 150                 155                 160

Ser Leu Val Arg Ser Ile Ser Asp Glu Cys Gly Gly Gln Gln Pro
                165                 170                 175

Val Asn Leu Thr Glu Gly Ile Ser Arg Met Ile Asn Asp Val Ala Ala
                180                 185                 190

Arg Thr Val Val Gly Asp Arg Cys Lys Tyr Gln Asp Glu Tyr Met His
                195                 200                 205

Glu Leu Asp Glu Val Val Arg Leu Ala Gly Gly Phe Asn Leu Ala Asp
                210                 215                 220

Leu Tyr Pro Ser Ser Arg Leu Val Arg Arg Phe Ser Ala Ala Ala Arg
225                 230                 235                 240

Asp Ala Arg Arg Cys Gln Arg Asn Met Tyr Arg Ile Ile Gln Ser Ile
                245                 250                 255

Ile Gln Glu Arg Glu Ala Met Pro Thr Pro Glu Arg Asp Glu Glu Asp
                260                 265                 270

Leu Leu Gly Val Leu Leu Arg Leu Gln Arg Glu Gly Gly Leu Gln Phe
                275                 280                 285

Ala Leu Thr Asn Glu Ile Val Ser Thr Val Ile Tyr Asp Ile Phe Ser
290                 295                 300

Ala Gly Ser Glu Thr Ser Ser Thr Val Leu Val Trp Ala Met Ser Glu
305                 310                 315                 320

Leu Val Lys Asn Pro Gln Val Met Arg Lys Ala Gln Ser Glu Val Arg
                325                 330                 335

Asp Thr Phe Lys Gly Asn Asn Lys Ile Thr Glu Ser Asp Leu Ile Lys
                340                 345                 350

Leu Arg Tyr Leu Gln Leu Val Ile Lys Glu Thr Leu Arg Leu His Ala
                355                 360                 365

Pro Val Pro Leu Leu Pro Arg Glu Cys Arg Glu Ser Cys Gln Ile
                370                 375                 380

Met Gly Tyr Asp Val Leu Lys Gly Thr Lys Val Phe Val Asn Ala Trp
385                 390                 395                 400

Ala Ile Ala Arg Asp Thr Gly Leu Trp Cys Asp Gly Glu Glu Phe Arg
                405                 410                 415

Pro Glu Arg Phe Glu Ser Ser Asn Ile Asp Phe Arg Gly Asn Asp Phe
                420                 425                 430

Glu Phe Thr Pro Phe Gly Ala Gly Arg Arg Val Cys Pro Gly Ile Thr
                435                 440                 445

Leu Gly Leu Ala Asn Leu Glu Leu Ala Leu Ala Ser Leu Leu Tyr His
                450                 455                 460

Phe Asp Trp Asp Leu Pro Asn Gly Ala Arg Leu Glu Asp Leu Asp Met
465                 470                 475                 480

Ala Glu Ala Phe Gly Ile Thr Leu Lys Arg Lys Ser Met Leu Trp Leu
                485                 490                 495

Lys Ala Lys Pro Tyr Asn Asn Phe Ile Pro Asn
                500                 505
```

<210> SEQ ID NO 11
<211> LENGTH: 1509
<212> TYPE: DNA
<213> ORGANISM: Solanum tuberosum

<400> SEQUENCE: 11

```
atgcaattct tgagcttggc ttccatcttc cttttctat cttttctgtt tttgttaagg      60
aaatggaaaa actcgaatag ccaatcgaaa aaattgcctc aggtccatg gaaacttcct     120
ttactaggaa gtatgcttca tatggctggt ggacttccac accatgtcct tagagattta    180
gccaaaaaat atggaccact tatgcatctt caacttggtg aagtctctgc agttgtagta    240
acttctcctg atatggcgaa agaagtacta aaaactcatg catcgctttt cgcctctagg    300
cctaaacttt tggccccgga aattgtttgt tacaacaggt ctgacattgc cttttgcccc    360
tacggagatt actggagaca aatgcgtaaa atttgtgtct tggaattgtt gagtgccaag    420
aatgtccggt catatggctc gattaggcgc gatgaagttg atcgccttgt taattttatc    480
cggtcatctt cgggtgagcc ggttaatttt actgaaaggt tgttttttgtt cacaagttca    540
atgacatgta gatcagcgtt cgggaaagtg ttcaaagaac aggacaaatt tatacaacta    600
atcaaagaag tgattgggtt agcaggagga tttgatgtgg ctgatatctt cccatcattg    660
aagtttctcc atgtgcttag tggaatgaaa ggtaaaatta tgaacgctca tcataaggta    720
gatgcaattg ttgaagatgt catcaatgag cacaagaaga aatttgcaat tgggaaaact    780
aatggtgcat taggtggtga agatctaatt gatgtcccta taagacttat gaatgatgga    840
ggccttcaat ttccgatcac caacgacaac atcaaagcta ttattttcga catgtttgct    900
gcaggaacag agacttcatc gtcaacactt gtctgggcaa tggtgcaaat gatgaaaaac    960
ccaagtgtaa tcgccaaagc tcaagcagaa gtgcgagaag cctttaaaga caagaaacg    1020
ttcgatgaaa atgatgtaga ggagctgaaa tacttaaagt tagtcattaa agaaactcta   1080
agactccatc caccagttcc acttttggtc caagagaat gtagggaaga gacggatata    1140
aacggctaca ctattcctgt gaagaccaaa gtcatggtta atgtttgggc attgggaaga   1200
gatccgaaat attgggatga tgcagaaagt tttaagccag agagatttga gcagcgctct   1260
gtcgactttg ttggtaacaa ttttgagtat cttcccttg gcggtgggag aaggatttgt    1320
cccgggatat catttggctt agctaatgtt tatttgccgt tggctcatt gttatatcac   1380
ttcgactgga aactccctat tggaatggag ccaaagact tgaacttgac tgaattggtt   1440
ggagtaactg ctgccagaaa agatgacctt attttggttg ccactcctta tgaaccacct   1500
cgacaatga                                                           1509
```

<210> SEQ ID NO 12
<211> LENGTH: 502
<212> TYPE: PRT
<213> ORGANISM: Solanum tuberosum

<400> SEQUENCE: 12

```
Met Gln Phe Leu Ser Leu Ala Ser Ile Phe Leu Phe Leu Ser Phe Leu
1               5                   10                  15

Phe Leu Leu Arg Lys Trp Lys Asn Ser Asn Ser Gln Ser Lys Lys Leu
            20                  25                  30

Pro Pro Gly Pro Trp Lys Leu Pro Leu Leu Gly Ser Met Leu His Met
        35                  40                  45

Ala Gly Gly Leu Pro His His Val Leu Arg Asp Leu Ala Lys Lys Tyr
```

```
            50                  55                  60
Gly Pro Leu Met His Leu Gln Leu Gly Glu Val Ser Ala Val Val
 65                  70                  75                  80

Thr Ser Pro Asp Met Ala Lys Glu Val Leu Lys Thr His Asp Ile Ala
                 85                  90                  95

Phe Ala Ser Arg Pro Lys Leu Leu Ala Pro Glu Ile Val Cys Tyr Asn
                100                 105                 110

Arg Ser Asp Ile Ala Phe Cys Pro Tyr Gly Asp Tyr Trp Arg Gln Met
                115                 120                 125

Arg Lys Ile Cys Val Leu Glu Leu Leu Ser Ala Lys Asn Val Arg Ser
                130                 135                 140

Tyr Gly Ser Ile Arg Arg Asp Glu Val Asp Arg Leu Val Asn Phe Ile
145                 150                 155                 160

Arg Ser Ser Ser Gly Glu Pro Val Asn Phe Thr Glu Arg Leu Phe Leu
                165                 170                 175

Phe Thr Ser Ser Met Thr Cys Arg Ser Ala Phe Gly Lys Val Phe Lys
                180                 185                 190

Glu Gln Asp Lys Phe Ile Gln Leu Ile Lys Glu Val Ile Gly Leu Ala
                195                 200                 205

Gly Gly Phe Asp Val Ala Asp Ile Phe Pro Ser Leu Lys Phe Leu His
210                 215                 220

Val Leu Ser Gly Met Lys Gly Lys Ile Met Asn Ala His His Lys Val
225                 230                 235                 240

Asp Ala Ile Val Glu Asp Val Ile Asn Glu His Lys Lys Lys Phe Ala
                245                 250                 255

Ile Gly Lys Thr Asn Gly Ala Leu Gly Gly Glu Asp Leu Ile Asp Val
                260                 265                 270

Leu Ile Arg Leu Met Asn Asp Gly Gly Leu Gln Phe Pro Ile Thr Asn
                275                 280                 285

Asp Asn Ile Lys Ala Ile Ile Phe Asp Met Phe Ala Ala Gly Thr Glu
                290                 295                 300

Thr Ser Ser Ser Thr Leu Val Trp Ala Met Val Gln Met Met Lys Asn
305                 310                 315                 320

Pro Ser Val Ile Ala Lys Ala Gln Ala Glu Val Arg Glu Ala Phe Lys
                325                 330                 335

Asp Lys Glu Thr Phe Asp Glu Asn Asp Val Glu Glu Leu Lys Tyr Leu
                340                 345                 350

Lys Leu Val Ile Lys Glu Thr Leu Arg Leu His Pro Pro Val Pro Leu
                355                 360                 365

Leu Val Pro Arg Glu Cys Arg Glu Glu Thr Asp Ile Asn Gly Tyr Thr
                370                 375                 380

Ile Pro Val Lys Thr Lys Val Met Val Asn Val Trp Ala Leu Gly Arg
385                 390                 395                 400

Asp Pro Lys Tyr Trp Asp Asp Ala Glu Ser Phe Lys Pro Glu Arg Phe
                405                 410                 415

Glu Gln Arg Ser Val Asp Phe Val Gly Asn Asn Phe Glu Tyr Leu Pro
                420                 425                 430

Phe Gly Gly Gly Arg Arg Ile Cys Pro Gly Ile Ser Phe Gly Leu Ala
                435                 440                 445

Asn Val Tyr Leu Pro Leu Ala His Leu Leu Tyr His Phe Asp Trp Lys
                450                 455                 460

Leu Pro Ile Gly Met Glu Pro Lys Asp Leu Asn Leu Thr Glu Leu Val
465                 470                 475                 480
```

Gly Val Thr Ala Ala Arg Lys Asp Asp Leu Ile Leu Val Ala Thr Pro
                485                 490                 495

Tyr Glu Pro Pro Arg Gln
            500

<210> SEQ ID NO 13
<211> LENGTH: 1506
<212> TYPE: DNA
<213> ORGANISM: Artificial Sequence
<220> FEATURE:
<223> OTHER INFORMATION: Codon optimized cDNA encoding for an N-terminal
      variant of CYP71D4, including NdeI site at 5'end and SalI-HindIII
      sites at 3'end

<400> SEQUENCE: 13

```
atggctctgt tgctggcagt tttctggtcc gcattgatta ttttggttct gtctcgcaaa      60
tggaaaaata gcaacagcca gagcaaaaag ctgccaccag gcccgtggaa actgccgttg     120
ctgggtagca tgctgcacat ggcaggcggc ctgccacacc atgtgctgcg tgatctggcg     180
aagaaatacg gtccgttgat gcatctgcag ctgggtgaag tgagcgcggt cgtggtgacg     240
agcccggata tggcgaaaga gtgctgaaga cccatgata tcgcattcgc aagccgtcca     300
aagctgctgg ctccggagat tgtctgctac aaccgtagcg acattgcgtt ctgtccatac     360
ggcgactact ggcgtcaaat gcgtaagatt tgtgtgctgg aactgctgag cgcgaaaaat     420
gtgcgcagct acggcagcat ccgtcgtgac gaggttgatc gtctggtgaa tttcattcgt     480
agcagcagcg gcgagccggt taactttacg gagcgtctgt ttctgtttac ctccagcatg     540
acctgccgtt ccgcgtttgg caaggtgttc aaggaacagg acaagttcat tcaactgatt     600
aaggaagtga tcggcctggc aggcggtttc gatgtggccg acatctttcc gagcctgaag     660
tttctgcacg tgctgtctgg tatgaaaggc aaaattatga atgcacacca caaggttgat     720
gcgatcgttg aagatgtgat taatgaacac aagaaaaagt tcgcgattgg taagacgaac     780
ggtgcgctgg tggtgagga tctgatcgat gttctgattc gcttgatgaa cgacggtggt     840
ctgcagtttc cgatcaccaa tgacaatatc aaagcgatta tcttcgacat gttcgccgca     900
ggcacggaga cgtctagcag caccctggtt tgggcgatgg ttcaaatgat gaagaatcca     960
agcgttattg caaaagccca agcggaagtt cgtgaagcgt ttaaagataa agagactttc    1020
gacgaaaacg atgttgagga actgaagtat ctgaagctgg ttatcaagga gacgctgcgt    1080
ctgcacccgc cggttccgct gctggtgccg cgtgaatgcc gtgaggagac ggatattaat    1140
ggttacacga ttccggttaa aaccaaagtc atggtgaatg tgtgggcgtt gggccgtgat    1200
ccgaagtact gggacgatgc ggagagcttt aaaccggaac gcttcgaaca gcgtagcgtg    1260
gattttgttg gcaataactt tgaatatctg ccattcggtg gtggtcgccg catttgccca    1320
ggcatttctt tcggtctggc aaacgtttat ctgccgctgg cgcatttgct gtaccacttc    1380
gactggaaat tgccgattgg catggaaccg aaagacttga acctgacgga actggtcggc    1440
gtgacggcgg ctcgtaagga tgacctgatt ctggtcgcaa ccccatacga accgccgcgt    1500
caataa                                                                1506
```

<210> SEQ ID NO 14
<211> LENGTH: 501
<212> TYPE: PRT
<213> ORGANISM: Artificial Sequence
<220> FEATURE:
<223> OTHER INFORMATION: CYP71D4opt, amino acid sequence of an
      N-terminal variant of CYP7D

<400> SEQUENCE: 14

| | | | | | | | | | | | | | | |
|---|---|---|---|---|---|---|---|---|---|---|---|---|---|---|
|Met|Ala|Leu|Leu|Leu|Ala|Val|Phe|Trp|Ser|Ala|Leu|Ile|Ile|Leu|Val|
|1| | | |5| | | | |10| | | | |15| |

Leu Ser Arg Lys Trp Lys Asn Ser Asn Ser Gln Ser Lys Lys Leu Pro
          20                25                30

Pro Gly Pro Trp Lys Leu Pro Leu Gly Ser Met Leu His Met Ala
     35                   40                  45

Gly Gly Leu Pro His His Val Leu Arg Asp Leu Ala Lys Lys Tyr Gly
50                      55                60

Pro Leu Met His Leu Gln Leu Gly Glu Val Ser Ala Val Val Val Thr
65                    70                75              80

Ser Pro Asp Met Ala Lys Glu Val Leu Lys Thr His Asp Ile Ala Phe
              85                90              95

Ala Ser Arg Pro Lys Leu Leu Ala Pro Glu Ile Val Cys Tyr Asn Arg
          100                105              110

Ser Asp Ile Ala Phe Cys Pro Tyr Gly Asp Tyr Trp Arg Gln Met Arg
          115                120              125

Lys Ile Cys Val Leu Glu Leu Leu Ser Ala Lys Asn Val Arg Ser Tyr
     130                  135              140

Gly Ser Ile Arg Arg Asp Glu Val Asp Arg Leu Val Asn Phe Ile Arg
145                   150                155             160

Ser Ser Ser Gly Glu Pro Val Asn Phe Thr Glu Arg Leu Phe Leu Phe
              165              170              175

Thr Ser Ser Met Thr Cys Arg Ser Ala Phe Gly Lys Val Phe Lys Glu
          180                185              190

Gln Asp Lys Phe Ile Gln Leu Ile Lys Glu Val Ile Gly Leu Ala Gly
            195              200            205

Gly Phe Asp Val Ala Asp Ile Phe Pro Ser Leu Lys Phe Leu His Val
     210                  215              220

Leu Ser Gly Met Lys Gly Lys Ile Met Asn Ala His His Lys Val Asp
225                   230                235             240

Ala Ile Val Glu Asp Val Ile Asn Glu His Lys Lys Lys Phe Ala Ile
              245                250              255

Gly Lys Thr Asn Gly Ala Leu Gly Gly Glu Asp Leu Ile Asp Val Leu
          260                265              270

Ile Arg Leu Met Asn Asp Gly Gly Leu Gln Phe Pro Ile Thr Asn Asp
            275              280            285

Asn Ile Lys Ala Ile Ile Phe Asp Met Phe Ala Ala Gly Thr Glu Thr
     290                  295              300

Ser Ser Ser Thr Leu Val Trp Ala Met Val Gln Met Met Lys Asn Pro
305                   310                315             320

Ser Val Ile Ala Lys Ala Gln Ala Glu Val Arg Glu Ala Phe Lys Asp
              325                330              335

Lys Glu Thr Phe Asp Glu Asn Asp Val Glu Glu Leu Lys Tyr Leu Lys
          340                345              350

Leu Val Ile Lys Glu Thr Leu Arg Leu His Pro Pro Val Pro Leu Leu
            355              360              365

Val Pro Arg Glu Cys Arg Glu Glu Thr Asp Ile Asn Gly Tyr Thr Ile
     370                  375              380

Pro Val Lys Thr Lys Val Met Val Asn Val Trp Ala Leu Gly Arg Asp
385                   390                395             400

Pro Lys Tyr Trp Asp Asp Ala Glu Ser Phe Lys Pro Glu Arg Phe Glu

-continued

```
                405                 410                 415
Gln Arg Ser Val Asp Phe Val Gly Asn Asn Phe Glu Tyr Leu Pro Phe
            420                 425                 430

Gly Gly Gly Arg Arg Ile Cys Pro Gly Ile Ser Phe Gly Leu Ala Asn
            435                 440                 445

Val Tyr Leu Pro Leu Ala His Leu Leu Tyr His Phe Asp Trp Lys Leu
            450                 455                 460

Pro Ile Gly Met Glu Pro Lys Asp Leu Asn Leu Thr Glu Leu Val Gly
465                 470                 475                 480

Val Thr Ala Ala Arg Lys Asp Asp Leu Ile Leu Val Ala Thr Pro Tyr
                485                 490                 495

Glu Pro Pro Arg Gln
            500

<210> SEQ ID NO 15
<211> LENGTH: 709
<212> TYPE: PRT
<213> ORGANISM: Mentha piperita

<400> SEQUENCE: 15

Met Glu Pro Ser Ser Gln Lys Leu Ser Pro Leu Glu Phe Val Ala Ala
1               5                   10                  15

Ile Leu Lys Gly Asp Tyr Ser Ser Gly Gln Val Glu Gly Gly Pro Pro
            20                  25                  30

Pro Gly Leu Ala Ala Met Leu Met Glu Asn Lys Asp Leu Val Met Val
        35                  40                  45

Leu Thr Thr Ser Val Ala Val Leu Ile Gly Cys Val Val Leu Ala
    50                  55                  60

Trp Arg Arg Ala Ala Gly Ser Gly Lys Tyr Lys Gln Pro Glu Leu Pro
65                  70                  75                  80

Lys Leu Val Val Pro Lys Ala Ala Glu Pro Glu Glu Ala Glu Asp Asp
                85                  90                  95

Lys Thr Lys Ile Ser Val Phe Phe Gly Thr Gln Thr Gly Thr Ala Glu
            100                 105                 110

Gly Phe Ala Lys Ala Phe Val Glu Glu Ala Lys Ala Arg Tyr Gln Gln
        115                 120                 125

Ala Arg Phe Lys Val Ile Asp Leu Asp Asp Tyr Ala Ala Asp Asp Asp
    130                 135                 140

Glu Tyr Glu Glu Lys Leu Lys Lys Glu Asn Leu Ala Phe Phe Phe Leu
145                 150                 155                 160

Ala Ser Tyr Gly Asp Gly Glu Pro Thr Asp Asn Ala Ala Arg Phe Tyr
                165                 170                 175

Lys Trp Phe Thr Glu Gly Lys Asp Arg Gly Glu Trp Leu Asn Asn Leu
            180                 185                 190

Gln Tyr Gly Val Phe Gly Leu Gly Asn Arg Gln Tyr Glu His Phe Asn
        195                 200                 205

Lys Ile Ala Ile Val Val Asp Asp Leu Ile Phe Glu Gln Gly Gly Lys
    210                 215                 220

Lys Leu Val Pro Val Gly Leu Gly Asp Asp Gln Cys Ile Glu Asp
225                 230                 235                 240

Asp Phe Ala Ala Trp Arg Glu Leu Val Trp Pro Glu Leu Asp Lys Leu
                245                 250                 255

Leu Arg Asn Glu Asp Asp Ala Thr Val Ala Thr Pro Tyr Ser Ala Ala
            260                 265                 270
```

```
Val Leu Gln Tyr Arg Val Val Phe His Asp His Ile Asp Gly Leu Ile
            275                 280                 285

Ser Glu Asn Gly Ser Pro Asn Gly His Ala Asn Gly Asn Thr Val Tyr
            290                 295                 300

Asp Ala Gln His Pro Cys Arg Ser Asn Val Ala Val Lys Lys Glu Leu
305                 310                 315                 320

His Thr Pro Ala Ser Asp Arg Ser Cys Thr His Leu Glu Phe Asn Ile
            325                 330                 335

Ser Gly Thr Gly Leu Met Tyr Glu Thr Gly Asp His Val Gly Val Tyr
            340                 345                 350

Cys Glu Asn Leu Leu Glu Thr Val Glu Glu Ala Glu Lys Leu Leu Asn
            355                 360                 365

Leu Ser Pro Gln Thr Tyr Phe Ser Val His Thr Asp Asn Glu Asp Gly
            370                 375                 380

Thr Pro Leu Ser Gly Ser Ser Leu Pro Pro Pro Phe Pro Pro Cys Thr
385                 390                 395                 400

Leu Arg Thr Ala Leu Thr Lys Tyr Ala Asp Leu Thr Ser Ala Pro Lys
            405                 410                 415

Lys Ser Val Leu Val Ala Leu Ala Glu Tyr Ala Ser Asp Gln Gly Glu
            420                 425                 430

Ala Asp Arg Leu Arg Phe Leu Ala Ser Pro Ser Gly Lys Glu Glu Tyr
            435                 440                 445

Ala Gln Tyr Ile Leu Ala Ser Gln Arg Thr Leu Leu Glu Val Met Ala
            450                 455                 460

Glu Phe Pro Ser Ala Lys Pro Pro Leu Gly Val Phe Phe Ala Gly Val
465                 470                 475                 480

Ala Pro Arg Leu Gln Pro Arg Phe Tyr Ser Ile Ser Ser Ser Pro Lys
            485                 490                 495

Ile Ala Pro Phe Arg Ile His Val Thr Cys Ala Leu Val Tyr Asp Lys
            500                 505                 510

Ser Pro Thr Gly Arg Val His Lys Gly Ile Cys Ser Thr Trp Met Lys
            515                 520                 525

Asn Ala Val Pro Leu Glu Glu Ser Asn Asp Cys Ser Trp Ala Pro Ile
530                 535                 540

Phe Val Arg Asn Ser Asn Phe Lys Leu Pro Thr Asp Pro Lys Val Pro
545                 550                 555                 560

Ile Ile Met Ile Gly Pro Gly Thr Gly Leu Ala Pro Phe Arg Gly Phe
            565                 570                 575

Leu Gln Glu Arg Leu Ala Leu Lys Glu Ser Gly Ala Glu Leu Gly Pro
            580                 585                 590

Ala Ile Leu Phe Phe Gly Cys Arg Asn Arg Lys Met Asp Phe Ile Tyr
            595                 600                 605

Glu Asp Glu Leu Asn Asp Phe Val Lys Ala Gly Val Val Ser Glu Leu
610                 615                 620

Ile Val Ala Phe Ser Arg Glu Gly Pro Met Lys Glu Tyr Val Gln His
625                 630                 635                 640

Lys Met Ser Gln Arg Ala Ser Asp Val Trp Asn Ile Ile Ser Asp Gly
            645                 650                 655

Gly Tyr Val Tyr Val Cys Gly Asp Ala Lys Gly Met Ala Arg Asp Val
            660                 665                 670

His Arg Thr Leu His Thr Ile Ala Gln Glu Gln Gly Ser Met Ser Ser
            675                 680                 685

Ser Glu Ala Glu Gly Met Val Lys Asn Leu Gln Thr Thr Gly Arg Tyr
```

Leu Arg Asp Val Trp
705

<210> SEQ ID NO 16
<211> LENGTH: 2130
<212> TYPE: DNA
<213> ORGANISM: Mentha piperita

<400> SEQUENCE: 16

```
atggaaccta gctctcagaa actgtctccg ttggaatttg ttgctgctat cctgaagggc      60
gactacagca gcggtcaggt tgaaggtggt ccaccgccag gtctggcagc tatgttgatg     120
gaaaataagg atttggtgat ggttctgacg acgtccgtgg cagtcctgat cggctgtgtc     180
gtggtcctgg catggcgtcg tgcggcaggt agcggtaagt acaagcaacc tgaactgcct     240
aaactggtgg tcccgaaagc agccgaaccg gaggaggcag aggatgataa aaccaagatc     300
agcgtgtttt tcggcaccca aaccggtacg gcagaaggtt tcgcgaaggc ttttgttgaa     360
gaggccaagg cgcgttatca gcaggcccgt ttcaaagtta tcgacctgga cgactatgcg     420
gcagacgatg acgagtacga agagaaactg aagaaggaaa acttggcatt cttcttcttg     480
gcgtcctacg gtgacggcga gccgacggac aacgcggcac gcttttacaa atggtttacg     540
gagggtaagg accgtggtga atggctgaac aatctgcagt acggcgtttt tggtctgggt     600
aaccgtcaat atgagcattt caataagatc gccattgtcg tcgatgatct gatcttcgag     660
caaggtggca agaagctggt tccggtgggt ctgggtgacg atgaccagtg cattgaggat     720
gattttgcgg cgtggcgtga actggtctgg ccggaactgg ataaactgct gcgtaacgaa     780
gacgacgcta ccgtggcaac cccgtacagc gccgctgtgc tgcaataccg cgtggttttc     840
cacgatcaca ttgacggcct gattagcgaa acggtagcc cgaacggtca tgctaatggc     900
aataccgtgt acgatgcgca cacccgtgc cgtagcaacg tcgcggtcaa gaaggaattg     960
catactccgg cgagcgatcg cagctgcacc cacctggaat ttaacattag cggtaccggc    1020
ctgatgtacg agacgggtga ccacgtcggt gtgtattgcg agaacctgtt ggaaaccgtg    1080
gaggaggccg agaagttgtt gaacctgagc ccgcagacgt acttctccgt tcacaccgac    1140
aacgaggacg gtacgccgtt gagcggcagc agcctgccgc caccgtttcc gccgtgcacc    1200
ttgcgcacgg cattgaccaa atacgcagac ttgacttctg caccgaaaaa gtcggtgctg    1260
gtggcgctgg ccgagtacgc atctgaccag ggtgaagcgg atcgtttgcg tttcttggcg    1320
agcccgagcg gcaaagagga atatgcacag tacatcttgg caagccagcg cacgctgctg    1380
gaggtcatgg cggagttccc gtcggcgaaa ccgccgctgg gtgtcttttt cgcgggtgtc    1440
gctccgcgcc tgcagccgcg tttctattcc attagctcta gcccgaagat cgcaccgttc    1500
cgtattcacg tgacctgcgc cctggtttat gacaaatccc ctaccggtcg cgttcataag    1560
ggcatctgta gcacgtggat gaaaaatgcg gtcccgctgg aagaaagcaa cgattgttcc    1620
tgggctccga tcttcgtccg caacagcaac ttcaagctgc cgaccgaccc gaaggttccg    1680
attatcatga ttggtccggg taccggtctg gccccttttc gtggcttttt gcaagagcgc    1740
ttggcgttga agagagcgg tgctgaattg ggtccggcga tcttgttctt ggttgccgt    1800
aaccgtaaaa tggactttat ttacgaggat gaactgaatg atttcgtcaa agcgggcgtt    1860
gtcagcgagc tgatcgtcgc ttttagccgc gaaggcccga tgaaagaata cgtgcaacac    1920
aaaatgagcc aacgtgcctc cgatgtgtgg aacatcatta gcgacggtgg ttatgtttat    1980
```

```
gtttgcggtg acgcgaaggg tatggctcgt gatgttcacc gtaccctgca taccatcgca    2040
caggagcaag gtagcatgtc cagctcggag gccgaaggta tggtcaaaaa cctgcaaacc    2100
accggtcgtt acctgcgtga tgtgtggtaa                                     2130
```

<210> SEQ ID NO 17
<211> LENGTH: 20
<212> TYPE: PRT
<213> ORGANISM: Artificial Sequence
<220> FEATURE:
<223> OTHER INFORMATION: Polypeptide fragment

<400> SEQUENCE: 17

```
Met Ala Leu Leu Leu Ala Val Phe Leu Gly Leu Ser Cys Leu Leu Leu
1               5                   10                  15
Leu Ser Leu Trp
            20
```

<210> SEQ ID NO 18
<211> LENGTH: 18
<212> TYPE: PRT
<213> ORGANISM: Artificial Sequence
<220> FEATURE:
<223> OTHER INFORMATION: Polypeptide fragment

<400> SEQUENCE: 18

```
Met Ala Leu Leu Leu Ala Val Phe Trp Ser Ala Leu Ile Ile Leu Val
1               5                   10                  15
Leu Ser
```

<210> SEQ ID NO 19
<211> LENGTH: 66
<212> TYPE: DNA
<213> ORGANISM: Artificial Sequence
<220> FEATURE:
<223> OTHER INFORMATION: DNA polylinker

<400> SEQUENCE: 19

```
gtcgacaatt aaccatggtt aattaagctt atatatggta ccatatatga attcattaat    60
ctcgag                                                               66
```

<210> SEQ ID NO 20
<211> LENGTH: 26
<212> TYPE: DNA
<213> ORGANISM: Artificial Sequence
<220> FEATURE:
<223> OTHER INFORMATION: extension containing a spacer sequence, the
      SalI recognition sequence and ribosome binding site

<400> SEQUENCE: 20

```
gtcgacaatt aggtaaaaaa taaacc                                         26
```

<210> SEQ ID NO 21
<211> LENGTH: 19
<212> TYPE: DNA
<213> ORGANISM: Artificial Sequence
<220> FEATURE:
<223> OTHER INFORMATION: 5' non-coding sequence comprising a HindIII
      recognition site and a RBS sequence

<400> SEQUENCE: 21

```
aagcttaagg aggtaaaaa                                                 19
```

<210> SEQ ID NO 22

```
<211> LENGTH: 30
<212> TYPE: DNA
<213> ORGANISM: Artificial Sequence
<220> FEATURE:
<223> OTHER INFORMATION: 3' non coding sequence comprising the KpnI,
      EcoRI and XhoI recognition sites

<400> SEQUENCE: 22
ggtaccatat atgaattcat taatctcgag                                           30
```